(12) United States Patent
Hiramatsu et al.

(10) Patent No.: US 7,659,112 B2
(45) Date of Patent: Feb. 9, 2010

(54) PROCESS FOR PRODUCING PHYSIOLOGICALLY ACTIVE PROTEIN USING GENETICALLY MODIFIED SILKWORM

(75) Inventors: Shingo Hiramatsu, Nagoya (JP); Takashi Tanaka, Nagoya (JP); Katsushige Yamada, Aichi (JP); Toshiki Tamura, Ushiku (JP)

(73) Assignee: Toray Industries, Inc., Tokyo (JP)

( * ) Notice: Subject to any disclaimer, the term of this patent is extended or adjusted under 35 U.S.C. 154(b) by 14 days.

(21) Appl. No.: 10/506,327

(22) PCT Filed: Mar. 6, 2003

(86) PCT No.: PCT/JP03/02675

§ 371 (c)(1),
(2), (4) Date: Sep. 2, 2004

(87) PCT Pub. No.: WO03/074699

PCT Pub. Date: Sep. 12, 2003

(65) Prior Publication Data

US 2005/0177877 A1 Aug. 11, 2005

(30) Foreign Application Priority Data

Mar. 6, 2002 (JP) .............................. 2002-060374
Sep. 13, 2002 (JP) .............................. 2002-268726

(51) Int. Cl.
*C12N 15/00* (2006.01)
*C12P 21/00* (2006.01)

(52) U.S. Cl. ............................ 435/320.1; 800/21; 800/4

(58) Field of Classification Search ........................ None
See application file for complete search history.

(56) References Cited

U.S. PATENT DOCUMENTS

2002/0137211 A1* 9/2002 Liu et al. .................... 435/455

FOREIGN PATENT DOCUMENTS

| EP | 1 391 509 A1 | 2/2004 |
| JP | 2001-161214 A | 6/2001 |
| JP | 2002306167 | 10/2002 |
| WO | WO-02/086119 A1 | 10/2002 |

OTHER PUBLICATIONS

Yamao et al., "Gene targeting in the silkworm by use of a baculovirus," Genes Dev. 13: 511-516, 1999.*
Yun et al., "Altering fibrin heavy chain gene of silkworm *Bombyx mori* by homologous recombination," Shengwu Huaxe yu Shengwu Wuli Xuebao 33(1): 112-116, 2001 (abstract only) (.*
GenBank Acc. No. AF226688, Zhou et al., "*Bombyx mori* fibroin heavy chain Fib-H (fib-H) gene, complete cds.," US Natl. Library of Medicine, Bethesda, MD, USA, Jun. 19, 2000, accessed by PTO on Oct. 19, 2006.*
Zhao et al., "Altering fibroin heavy chain gene of silkworm *Bombyx mori* by homologous recombination," Acta Biochimica et Biophysica Sinica 33(1): 112-116, Jan. 2001, original with attached English translation.*
Zhang et al., "Flourescent transgenic silkworm," Acta Biochimica et Biophysica Sinica 31(2): 119-123, 1999.*
Zhou, CZ et al, "Fine Organization of *Bombyx mori* Fibroin Heavy Chain Gene", Nucleic Acids Res., 2000, vol. 28. No. 12, pp. 2413 to 2419.
Tomita, M. et al., "Transgenic Silkworms Produce Recombinant Human Type III Procollagen in Cocoons", Nat. Biotechnol., Jan. 2003, vol. 21, No. 1, pp. 52 to 56.
Yoshizato, Katsutoshi, "A Proposal for Application of Recombinant Insects (Kumikaetai Konchu Riyo Eno Teigen)", Sanshi Konchuken Shiryo, No. 28, pp. 93 to 95 (with English language translation).
Toshiki et al., "Germline transformation of the silkworm *Bombyx mori* L. using a piggyBac transposon-derived vector," Nature Biotechnology, vol. 16, pp. 81-85 (Jan. 2000).
Okano et al., "Production of Canine IFN-γ in Silkworm by Recombinant Baculovirus and Characterization of the Product," Journal of Interferon and Cytokine Research, vol. 20, pp. 1015-1022 (2000).
Xiao-Hui et al., "Effects of rhM-CSF expressed in silkworm on cytokine productions and membrane molecule expressions of human monocytes," Acta Pharmacol. Sin., vol. 21, No. 9, pp. 797-801 (Sep. 2000).
Ishihara et al., "Preparation of recombinant rat interleukin-5 by baculovirus expression system and analysis of its biological activities," Biochimica et Biophysica Acta 1451, pp. 48-58 (1999).
T. Tamura, "Construction and utilization of transgenic silkworm using transposon", Fiber Preprints, Japan, vol. 56, No. 2, 2001, p. 38-41.
A. Yanai et al., "Development of mass production system for feline interferon using silkworm", Research Journal of Food and Agriculture, vol. 25, No. 2, 2002, p. 30-33.
T. Tamura et al., "Generation of transgenic silkworm", Agriculture and Horticulture, vol. 75, No. 8, 2000, p. 17-24.
Yoshizato, Katsutoshi, "A Proposal for Application of Recombinant Insects (Kumikaetai Konchu Riyo Eno Teigen)", Sanshi Konchuken Shiryo, No. 28, pp. 93 to 95 (with English language translation), 2001.

* cited by examiner

*Primary Examiner*—Fereydoun G Sajjadi
(74) *Attorney, Agent, or Firm*—Birch, Stewart, Kolasch & Birch, LLP

(57) ABSTRACT

The present invention provides a genetic engineering material for insects that enables a target protein to be purified easily, without requiring the use of recombinant baculovirus, while simultaneously providing a process for producing exogenous protein using that genetic engineering material. A gene recombinant silkworm is obtained by inserting an exogenous protein gene such as a cytokine gene coupled to a promoter that functions in silk glands into a silkworm chromosome. An exogenous protein such as a cytokine is then extracted and purified from the silk glands or cocoon of that silkworm or its offspring. A large amount of exogenous protein can be produced within silk gland cells, outside silk gland cells or in silk thread or a cocoon by inserting an expression gene cassette, in which the DNA sequence of the 3' terminal portion and the DNA sequence of the 5' terminal portion of fibroin H chain gene are fused to the exogenous protein gene, into silk gland cells and so forth.

20 Claims, 19 Drawing Sheets

SerP: SERICIN-1 GENE PROMOTER
IFN: FELINE INTERFERON-ω GENE
BGHpA: BOVINE GROWTH HORMONE POLY A
A3P: A3 PROMOTER
GFP: GREEN FLUORESCENCE PROTEIN
SV40pA: SV40 POLY A
ITR: INVERTED TERMINAL SEQUENCE

FibHP: FIBROIN H CHAIN GENE PROMOTER
IFN: FELINE INTERFERON-ω GENE
BGHpA: BOVINE GROWTH HORMONE POLY A
A3P: A3 PROMOTER
GFP: GREEN FLUORESCENCE PROTEIN
SV40pA: SV40 POLY A
ITR: INVERTED TERMINAL SEQUENCE

M: MOLECULAR WEIGHT MARKER

FROM FIG. 13

PROCESS FOR PRODUCING PHYSIOLOGICALLY ACTIVE PROTEIN USING GENETICALLY MODIFIED SILKWORM

TECHNICAL FIELD

The present invention relates to a process for producing a recombinant cytokine using a silkworm incorporating a cytokine gene in its chromosomes. In addition, the present invention relates to a gene recombinant silkworm having the property of producing a recombinant cytokine in a silk gland or cocoon and silk thread, and a vector for inserting an exogenous gene into silkworm chromosomes for producing the recombinant silkworm. In addition, the present invention also relates to a process for producing exogenous protein using insect cells, insect tissue or insects to which a gene has been inserted using the aforementioned vector. Moreover, the present invention relates to silk thread containing an exogenous protein produced by a recombinant silkworm obtained in the present invention.

BACKGROUND ART

The production of exogenous proteins using gene recombination technology is used in various industries. The hosts used for their production consist mainly of *E. coli*, yeast, animal cells, plant cells and insect cells. However, a host has yet to be developed that is capable of efficiently producing all kinds of exogenous proteins and, as it is necessary to construct a production system for each target protein, a technical breakthrough is being sought in technology for producing exogenous proteins in individual hosts.

Systems using bacteria like *E. coli* or yeast have problems with posttranslational modification, and in some cases these systems are unable to synthesize proteins in a form that allows them to function adequately. In addition, although animal cells allow proteins to be synthesized in a functional form, it is typically difficult to grow these cells and the production volume is low thereby making this uneconomical.

On the other hand, in the production of gene recombinant proteins using insects or insect cells, useful proteins having enzymatic or physiological activity can be produced comparatively inexpensively and modifications can be obtained, following protein translation, that resemble those in animals. More specifically, a method in which a baculovirus incorporated a recombinant exogenous gene is infected into insects or insect cells allows the exogenous protein to be produced comparatively inexpensively, and physiologically active proteins are known that have been commercialized as pharmaceuticals (Japanese Unexamined Patent Publication Nos. 61-9288 and 61-9297).

In the case of the production of cytokines, which are physiologically active substances having immunoregulatory functions and which are attracting attention in pharmaceutical applications, methods are disclosed in Japanese Unexamined Patent Publication Nos. 3-139276 and 9-234085 in which silkworms are inoculated with BmNPV containing a feline interferon-ω gene and a canine interferon-γ gene, respectively. In addition, a process for producing human collagen using insect cells infected with baculovirus is known as an example of the production of a protein other than interferon using insects (Japanese Unexamined Patent Publication No. 8-23979).

However, as technologies for producing recombinant proteins using insects or insect cells of the prior art use a recombinant virus to incorporate an exogenous gene, there is the problem of the need for deactivation or containment of recombinant virus from the viewpoint of safety. In addition, in methods in which a recombinant virus is inoculated into a silkworm, as the inoculation of the recombinant virus is troublesome task and the target exogenous protein is produced in silkworm hemolymph, it is necessary to purify the target recombinant protein from the large amount of contaminating proteins originating in the body fluids of the silkworm. Consequently, there was the problem of it being difficult to obtain a highly pure recombinant protein.

On the other hand, attempts have been made in recent years to recombine exogenous genes into insect chromosomes, and a method has been developed that uses homologous recombination to introduce and express in silkworm chromosomes a fused gene in which jellyfish green fluorescence-protein gene was coupled to silkworm fibroin L chain gene using DNA of *Autographa californica* nuclear polyhedrosis virus (AcNPV), which is a type of nuclear polyhedrosis virus (Genes Dev., 13, 511-516, 1999), and a silkworm containing human collagen gene and a production process have been disclosed that utilize this technology (Japanese Unexamined Patent Publication No. 2001-161214). Recently, research has been conducted on a method for expressing a protein encoded by an exogenous gene by stably introducing that exogenous gene into silkworm chromosomes using piggyBac, which is a transposon originating in a lepidopteron, using the jellyfish green fluorescence protein as a model, and the gene has been confirmed to be stably propagated to offspring by mating (Nature Biotechnology, 18, 81-84, 2000).

However, in the aforementioned method for inserting an exogenous protein gene into insect chromosomes using AcNPV, as a recombinant baculovirus (AcNPV) is used, there is still the problem of having to deactivate and contain the recombinant virus. In the example that used the piggyBac transposon, as the amount of green fluorescence protein produced is inadequate and as it is also produced throughout the silkworm, sophisticated purification technology is required to recover the expressed recombinant green fluorescence protein in a highly pure form, thereby resulting in the method being uneconomical. In addition, the amount of recombinant protein produced is inadequate and extremely low.

Namely, in this technology for producing an exogenous protein using insect cells as a host, there are several problems such as the need to deactivate and contain the recombinant baculovirus, the difficulty in purifying the target protein from body fluid in which a large amount of contaminating proteins are present, as in the case of using silkworms, and the expressed amount of the target protein being low.

There are no known examples, thus far, of expressing a target protein by inserting a gene that encodes a physiologically active protein such as a cytokine gene into silkworm chromosomes. In addition, there are also no examples of having recovered a recombinant cytokine from a site, other than silkworm body fluid, such as a silk gland or silk thread secreted by silkworms, and confirming the physiological activity of the resulting cytokine. In addition, there are also no precedents regarding a silkworm capable of inheriting such properties. In addition, there are no examples of having produced a large amount of recombinant protein in silk thread using a recombinant silkworm produced using a transposon.

DISCLOSURE OF THE INVENTION

Although extensive research has been conducted on technologies for producing recombinant proteins using insects, there are problems such as the need to deactivate and contain the recombinant baculovirus in which the exogenous protein gene has been incorporated, or the need to take a lot of time and labor associated with inoculating the recombinant virus. In addition, the production of exogenous protein in silkworms using recombinant baculovirus had the problem of it being difficult to extract and purify the target protein from body fluid containing large amounts of contaminating proteins.

Although studies have been conducted on technologies, for producing recombinant proteins, in which an exogenous protein gene has been inserted into silkworm chromosomes, these have problems consisting of the small amount of target exogenous protein produced and the difficulty in purifying the target protein from silkworm body fluid.

In consideration of these circumstances, the object of the present invention is to provide a genetic engineering material for insects that does not require the use of recombinant baculovirus and enables a target protein having physiological activity to be purified easily, while simultaneously providing a process for producing exogenous protein using that genetic engineering material.

As a result of extensive studies, the inventors of the present invention found that, by inserting a DNA sequence having a structure in which a gene that encodes a target protein is coupled downstream from a promoter specifically expressed in silkworm silk glands into silkworm chromosomes using DNA originating in a transposon, the target protein is produced in the silk glands, or the cocoon and the silk thread, in a form that retains physiological activity, thereby leading to completion of the present invention. In the present invention, as the recombinant protein can be recovered from the silk glands or silk and cocoon thread without containing a large amount of contaminants, it offers the advantage of allowing the target protein to be purified easily. Moreover, as a virus like baculovirus is not used, virus deactivation is not necessary thereby allowing the recombinant protein to be produced both easily and safely.

In addition, as a result of conducting extensive studies focusing on the fact that the silkworm silk glands, and particularly the posterior silk gland, produces a large amount of fibroin that accounts for 70 to 80% of silk protein, and that the fibroin is secreted by the silk gland cells, the inventors of the present invention found that the amount of exogenous protein produced is increased considerably by inserting into silk gland cells a gene cassette in which the 5' terminal of an exogenous protein gene is coupled to the 3' terminal of a fibroin H chain gene 5' terminal portion containing a first intron of fibroin H chain gene downstream from a promoter expressed in the silk glands so that the amino acid frames are continuous. In addition, it was also found that a large amount of exogenous protein is secreted and produced by silk gland cells when a fused gene in which the 3' terminal portion of fibroin H chain gene is coupled to the 3' side of an exogenous protein gene, so that the amino acid frames are continuous, is expressed under the control of a promoter expressed in silk glands. In addition, it was also found that a recombinant silkworm produces a large amount of a target protein in its silk threads when a gene cassette was produced in which a DNA sequence of the 5' terminal portion containing a first intron of fibroin H chain gene on the 5' side of an exogenous protein gene, and a DNA sequence of the 3' terminal portion of fibroin H chain gene on the 3' side, were respectively designed so that their amino acid frames were continuous, followed by producing a recombinant silkworm in which that gene cassette was inserted into its chromosomes.

The inventors of the present invention succeeded in producing a large amount of exogenous protein in silk gland cells, outside silk gland cells and in silk thread by inserting into silk gland cells and so forth an expression gene cassette in which the DNA sequence of the 5' terminal portion and the DNA sequence of the 3' portion of fibroin H chain gene were fused to an exogenous protein gene, and were able to establish an exogenous protein production technology that facilitates purification by producing an exogenous protein using silk glands instead of using a recombinant baculovirus.

Namely, the present invention relates to a process for producing a recombinant cytokine comprising producing a gene recombinant silkworm that incorporates a cytokine gene in its chromosomes, and recovering the cytokine from the silk glands or cocoon and silk thread. Moreover, the present invention also relates to a gene recombinant silkworm in which a cytokine gene is incorporated, and a gene recombinant vector used to insert the cytokine gene into the silkworm.

Moreover, the present invention relates to a genetic engineering material, such as the gene cassette or vector described below, capable of being used for exogenous protein production in insects, a transformant, a process for producing exogenous protein using that transformant, and silk thread containing exogenous protein.

Thus, the present invention provides 1) a gene cassette for expressing an exogenous protein comprising (1) a promoter expressed in silk glands, and (2) a gene coupled downstream from (1) in which the 5' terminal portion of fibroin H chain gene is fused to the 5' side of an exogenous protein-structural gene.

Moreover, the present invention provides 2) a gene cassette for expressing an exogenous protein comprising (1) a promoter expressed in silk glands, and (2) a gene coupled downstream from (1) in which the 3' terminal portion of fibroin H chain gene is fused to the 3' side of an exogenous protein structural gene not containing a stop codon. Alternatively, the present invention provides a gene cassette for expressing an exogenous protein comprising (1) a promoter expressed in silk glands, and (2) a gene coupled downstream from (1) in which an exogenous protein structural gene is fused to the 3' side of the 3' terminal portion of fibroin H chain gene.

Moreover, the present invention provides 3) a gene cassette for expressing an exogenous protein comprising (1) a promoter expressed in silk glands, and (2) a gene coupled downstream from (1) in which the 5' terminal portion of fibroin H chain gene is fused to the 5' side of an exogenous protein structural gene not containing a stop codon, and the 3' terminal portion of fibroin H chain gene is fused to the 3' side of the structural gene.

In addition, the present invention provides 4) an expression vector for insect cells containing a gene cassette for expressing an exogenous protein according to any of the aforementioned 1) through 3).

Moreover, the present invention provides 5) a process for producing exogenous protein comprising inserting an expression vector for insect cells according to the aforementioned 4) into insect cells.

Moreover, the present invention provides 6) a process for producing exogenous protein comprising producing a recombinant silkworm in which a gene cassette for expressing an exogenous protein according to any of the aforementioned 1) through 3) is incorporated in its chromosomes, and after producing the exogenous protein in the silk glands or silk thread of the resulting recombinant silkworm, recovering the exogenous protein from the silk glands or silk thread.

In addition, the present invention provides 7) a recombinant silkworm in which a gene cassette for expressing an exogenous protein according to any of the aforementioned 1) through 3) is incorporated in its chromosomes, and has the ability to produce exogenous protein in its silk glands or silk thread.

Moreover, the present invention provides 8) a silk thread containing an exogenous protein produced by the silkworm according to the aforementioned 7).

BEST MODE FOR CARRYING OUT THE INVENTION

Figure 1:
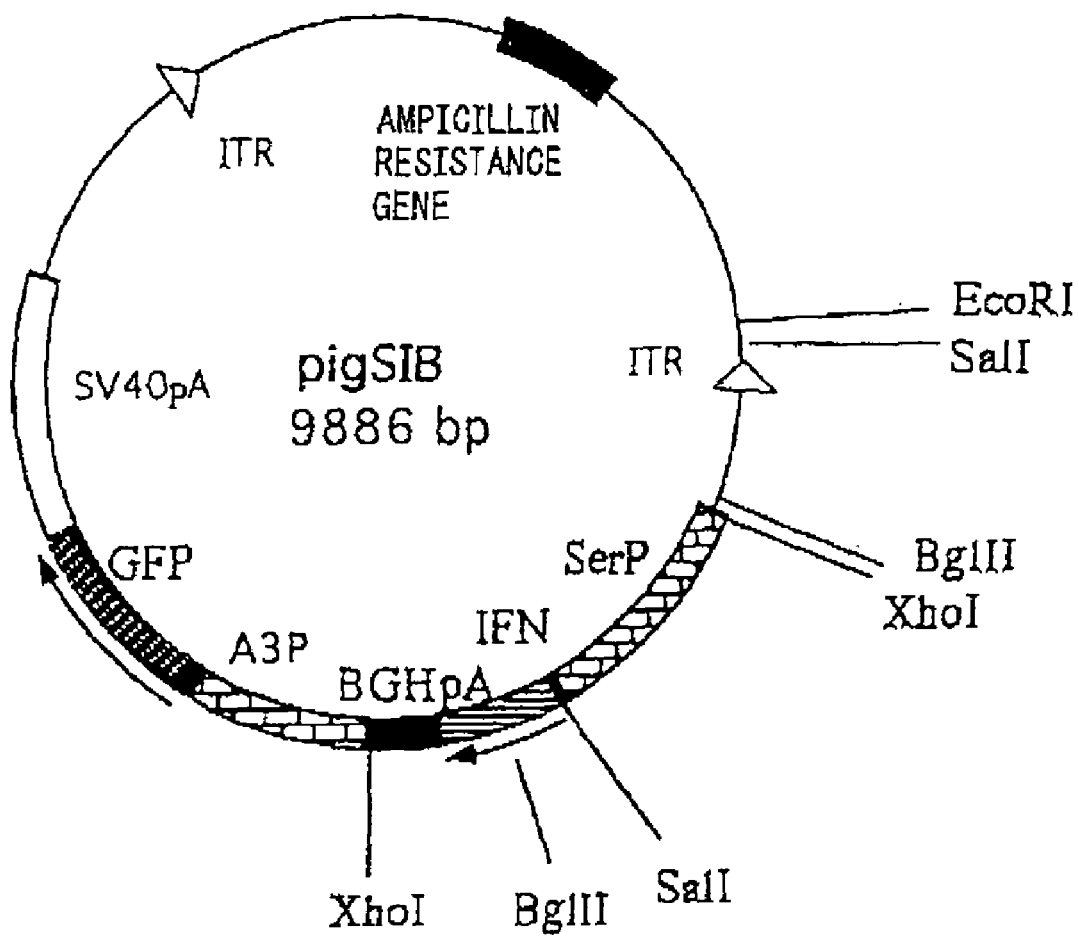
FIG. 1 is a drawing showing a restriction map of gene insertion vector pigSIB.

Cytokines are proteins produced by various cells that have immunoregulatory activity, antiviral activity and blood cell growth activity on hematopoietic cells and immunocytes. Their activity is demonstrated as a result of forming a precise higher order structure and bonding to specific receptors on the cell membrane. They have previously been applied clinically to humans and animals based on the characteristics of their activity.

Although there are no particular limitations on the cytokines of the present invention, they should be cytokines for which their physiological activity is maintained when expressed in silkworms, examples of which include physiologically active substances having immunoregulatory activity, antiviral activity or blood cell growth activity and so forth such as human interferon-α, β and γ (J. Interferon Res. 5, 521-526, 1985; Nucleic Acids Res. 10, 2487-2501, 1982), human interleukin-12 (J. Immunol. 146, 3074-3081, 1991), human granulocyte colony stimulating factor (Nature, 319, 415-418, 1986), human erythropoietin (Nature, 313, 806-810, 1985), human thrombopoietin (Cell, 77, 1177-1124, 1994), feline interferon-ω, (Biosci. Biotech. Biochem., 56, 211-214, 1992, GenBank database registration no. E04599), feline erythropoietin (GenBank database registration no. FDU00685), feline granulocyte colony stimulating factor (Gene, 274, 263-269, 2001), canine interferon-γ (GenBank database registration no. S41201), canine interleukin-12 (Japanese Unexamined Patent Publication No. 10-36397) and canine granulocyte colony stimulating factor (U.S. Pat. No. 5,606,024). Preferable examples of cytokines include interferons and colony stimulating factors, and these preferably include interferon-α, β, γ, ω and τ along with colony stimulating factor, erythropoietin and thrombopoietin. More preferable examples of cytokines include feline interferon-ω, feline granulocyte colony stimulating factor and human interferon-β.

Feline interferon-ω gene is obtained by cutting out from a plasmid extracted from, for example, E. coli (pFeIFN1) (Patent Microorganism Depository No. 1633). In addition, this gene can also be obtained from rBNV100 produced by co-transfecting into established silkworm cells with a recombinant plasmid produced by ligating feline interferon-ω gene to a silkworm cloning vector (T. Horiuchi, et al., Agric. Biol. Chem., 51, 1573-1580, 1987), and silkworm nuclear polyhedrosis virus.

Feline granulocyte colony stimulating factor can be obtained by stimulating CRFK cells, which are cultured cells originating in feline kidney, with LPS followed by recovering mRNA from the cells and then carrying out PCR using the cDNA obtained by reverse transcription as a template and using primers established with reference to GenBank database registration no. AB042552.

Human interferon-β gene can be acquired by cutting out from plasmid ORF-hIFN-β (Invitrogen) that encodes its cDNA.

The method for inserting a gene into silkworm chromosomes used in the present invention should enable the gene to be stably incorporated and expressed in the chromosomes, and be stably propagated to offspring, as well, by mating. Although a method using micro-injection into silkworm eggs or a method using a gene gun can be used, a method that is used preferably consists of the micro-injection into silkworm eggs with a target gene containing vector for insertion of an exogenous gene into silkworm chromosomes and helper plasmid containing a transposon gene (Nature Biotechnology 18, 81-84, 2000) simultaneously.

The target gene is inserted into reproductive cells in a recombinant silkworm that has been hatched and grown from the micro-injected silkworm eggs. Offspring of a recombinant silkworm obtained in this manner are able to stably retain the target gene in their chromosomes. The gene recombinant silkworm obtained in the present invention can be maintained in the same manner as ordinary silkworms. Namely, up to fifth instar silkworms can be raised by incubating the eggs under normal conditions, collecting the hatched larva to artificial feed and then raising under the same conditions as ordinary silkworms.

Gene recombinant silkworms obtained in the present invention are able to pupate and produce a cocoon in the same manner as ordinary silkworms. Males and females are distinguished in the pupa stage, and after having transformed into moths, males and females mate and eggs are gathered on the following day. The eggs can be stored in the same manner as ordinary silkworm eggs. The gene recombinant silkworms of the present invention can be maintained on subsequent generations by repeating the breeding as described above, and can be increased to large numbers.

The exogenous gene insertion vector used for the purpose of inserting a cytokine gene used in the present invention into silkworm chromosomes is not subject to any particular limitations provided it is designed so as to precisely control cytokine expression. Normally, it has a structure in which the cytokine gene is coupled to downstream from a promoter specifically expressed in the silk glands and upstream from an arbitrary poly A sequence, and has a pair of DNA sequences originating in a transposon outside these gene sequences. Moreover, a signal sequence originating in an arbitrary gene may be coupled between the cytokine gene and the promoter, and an arbitrary gene sequence may also be coupled between the cytokine gene and poly A. In addition, an artificially designed and synthesized gene sequence can also be coupled. In addition, a sequence for replication within a bacterial host, antibiotic resistance gene, fluorescence protein gene or LacZ gene and so forth can also be coupled as necessary. For example, the gene of green fluorescence protein GFP coupled downstream from a suitable promoter can be inserted at a suitable location between a pair of transposon DNA sequences. As a result, this facilitates screening for gene recombinant silkworms. In addition, this vector may also contain all or a portion of pUC9, pUC19 or other plasmids originating in *E. coli*.

Moreover, although there are no particular limitations on the promoter used here, and any promoter originating in any organism can be used provided its acts effectively within silkworm cells, a promoter that has been designed to specifically induce protein in silkworm silk glands is preferable. Examples of silkworm silk gland protein promoters include fibroin H chain promoter, fibroin L chain promoter, p25 promoter and sericin promoter.

Examples of other gene sequences used in addition to the promoter include signal sequences, poly A sequences and other sequences that control gene expression. These are not limited to specific gene sequences, but rather those which are suitable for expression of the target gene can be selected. Examples include sequences originating in the target protein such as signal sequences of cytokines such as feline interferon-o and poly A sequences, and signal sequences and poly A sequences of insect protein contained in the silkworm serving as the host. Alternatively, other examples include sequences that have been proven to be generally effective for expressing proteins such as SV40 poly A and bovine growth hormone poly A. By changing the gene sequence of the aforementioned promoters and the other sequences coupled with the cytokine genes, the locations where they are expressed and the amounts expressed can be controlled.

In the present invention, a "gene cassette for expressing an exogenous protein" refers to a set of DNA required for a synthesis of protein encoded by the exogenous protein structural gene in the case of being inserted into insect cells. This gene cassette for expressing an exogenous protein contains an exogenous protein structural gene and a promoter that promotes expression of that gene. Normally, it also contains a terminator and poly A addition region, and preferably contains a promoter, exogenous protein structural gene, terminator and poly A addition region. Moreover, it may also contain a secretion signal gene coupled between the promoter and the exogenous protein structural gene. An arbitrary gene sequence may also be coupled between the poly A addition sequence and the exogenous protein structural gene. In addition, an artificially designed and synthesized gene sequence can also be coupled.

In addition, a "gene cassette for inserting a gene" refers to a gene cassette for expressing an exogenous gene having an inverted repetitive sequence of a pair of piggyBac transposons on both sides, and consisting of a set of DNA inserted into insect cell chromosomes through the action of the piggyBac transposons.

There are no particular limitations on the method used to acquire DNA used in the present invention. Examples of such methods include a method in which a required gene region is amplified and acquired using a polymerase chain reaction (PCR) based on known genetic information, and a method in which a genome library or cDNA library is screened using homology as an indicator based on known genetic information. In the present invention, these genes include variants resulting from genetic polymorphism and artificial mutation treatment using mutagens and so forth. Genetic polymorphism refers to that in which a portion of the base sequence of a gene is altered by a sudden spontaneous mutation in the gene.

Although there are no particular limitations on the promoter in the gene cassette for expressing an exogenous protein, that having a high level of activity that promotes expression of an exogenous protein gene is preferable. Although examples include the promoter of *drosophila* heat shock protein gene described in Japanese unexamined Patent Publication No. 6-261770 and the promoter of silkworm actin gene (Nature Biotechnology 18, 81-84, 2000), promoters having a high level of promoting activity in silkworm silk gland cells are preferable, examples of which include the promoters of fibroin H chain gene (base numbers 255-574 of GenBank registration no. V00094), fibroin L chain gene (Gene, 100, 151-158; GenBank registration no. M76430) and sericin gene (base numbers 599-1656 of GenBank registration no. AB007831).

"Exogenous protein structural gene" refers to a gene not possessed by host cells in which a gene is to be expressed, and which encodes a protein not inherently produced by the host cells. Although there are no particular limitations thereon, in consideration of industrial value, examples include genes of proteins that are produced by humans or mammals such as genes of growth hormones, cytokines, growth factors and cell structural proteins. In addition, genes of enzymes and various proteins produced by microbes, plants or insects are also included in the scope of the present invention.

In the gene cassette for expressing an exogenous protein in the present invention, the 5' terminal portion of fibroin H chain gene is a DNA sequence having action that enhances expression of exogenous protein gene by a promoter, and contains a first exon of fibroin H chain gene, all or a portion of a first intron, and a portion of a second exon. By fusing the 5' side of an exogenous protein structural gene to the 3' side of this second exon so that the amino acid reading frame is contiguous, the amount of exogenous protein produced can be improved. However, since surplus amino acid residues are added to the N terminal side of the target exogenous protein if the second axon portion is too long, there are cases in which the structure or activity of the target exogenous protein is lost. Consequently, it is necessary that the second exon portion have a suitable length according to the purpose. In many cases, favorable results can be obtained by making the second exon portion to extend to immediately after or up to several amino acid residues from the secretion signal gene of fibroin H chain gene. In addition, as the region upstream from the 5' side of fibroin H chain gene promoter, namely a roughly 5.5 kbp upstream region, is considered to be the region that enhances promoter activity, adding this region can be expected to increase the amount of target protein expressed.

In the case of producing an exogenous protein in silkworm silk glands, the 3' terminal portion of fibroin H chain gene is a DNA sequence having the effect of causing secretion of a large amount of exogenous protein outside the silk gland cells. A recombinant silkworm in which a gene cassette for expressing an exogenous protein, in which the 3' terminal portion of fibroin H chain gene serving as the signal for secreting into silk thread is fused to the 3' side, is inserted into its chromosomes is able to produce exogenous protein in its silk thread. In addition, the 3' terminal portion of fibroin H chain gene may be present upstream or downstream from the exogenous protein gene or within the exogenous protein gene.

In the case at least one cysteine residue is present in this portion and the 3' terminal of fibroin H chain gene is used as is, the cysteine residue is located at the 20th residue from the carboxyl terminal of the fibroin H chain gene. This cysteine fulfills the role of bonding to fibroin L chain by a disulfide bond. There are no particular limitations on the length of the DNA sequence of the 3' terminal portion of fibroin H chain gene provided it does not inhibit formation of the disulfide bond with fibroin L chain. As a repetitive DNA sequence continues from about 100 or more bases upstream from the 3' terminal of fibroin H chain, cleaving the DNA sequence of this upstream portion to an arbitrary length is difficult with a restriction endonuclease. Thus, in consideration of the ease of genetic engineering techniques, roughly 100 base pairs on the 3' portion where the repetitive DNA sequence of fibroin H chain gene ends can be preferably used for the 3' terminal portion of fibroin H chain. In addition, as a large number of amino acids originating in the carboxyl terminal of fibroin H chain protein bond to the carboxyl terminal or amino terminal of the exogenous protein if the 3' terminal portion of fibroin H chain gene is excessively long, there are cases in which the structure or activity of the target exogenous protein is lost. Thus, there are cases in which it is necessary to make the DNA sequence of the 3' terminal portion of fibroin H chain gene as short as possible depending on the target protein.

Although there are no particular limitations on the poly A region, a poly A region of a protein gene expressed in large amounts in silk glands, such as fibroin H chain, fibroin L chain or sericin, can be used preferably.

A vector in the present invention refers to that having a cyclic or linear DNA structure. A vector capable of replicating in *E. Coli* and having a cyclic DNA structure is particularly preferable. This vector can also incorporate a marker gene such as an antibiotic resistance gene or jellyfish green fluorescence protein gene for the purpose of facilitating selection of transformants.

Although there are no particular limitations on the insect cells used in the present invention, they are preferably lepidopteron cells, more preferably *Bombyx mori* cells, and even more preferably silkworm silk gland cells or cells contained in *Bombyx mori* eggs. In the case of silk gland cells, posterior silk gland cells of fifth instar silkworm larva are preferable because there is active synthesis of fibroin protein and they are easily handled.

There are no particular limitations on the method used to incorporate a gene cassette for expression of exogenous protein and a vector into the insect cells. Although the calcium phosphate method, methods using electroporation, methods using liposomes, methods using a gene gun and methods using micro-injection can be used for incorporation into cultured insect cells, in the case of incorporating into silkworm silk gland cells, for example, a gene can be easily incorporated into posterior silk gland tissue removed from the body of a fifth instar silkworm larvae using a gene gun.

Gene incorporation into the posterior silk gland using a gene gun can be carried out by, for example, bombarding gold particles coated with a vector containing a gene cassette for expressing exogenous protein into a posterior silk gland immobilized on an agar plate and so forth using a particle gun (Bio-Rad, Model No. PDS-1000/He) at an He gas pressure of 1,100 to 1,800 psi.

In the case of incorporating a gene into cells contained in eggs of *Bombyx mori*, a method using micro-injection is preferable. Here, in the case of performing micro-injection into eggs, it is not necessary to micro-inject into the cells of the eggs directly, but rather a gene can be incorporated by simply micro-injecting into the eggs.

A recombinant silkworm containing the "gene cassette for expressing an exogenous protein" of the present invention in its chromosomes can be acquired by micro-injecting a vector having a "gene cassette for inserting a gene" into the eggs of *Bombyx mori*. For example, a first generation (G1) silkworm is obtained by simultaneously micro-injecting a vector having a "gene cassette for inserting a gene" and a plasmid in which a piggyBac transposase gene is arranged under the control of silkworm actin promoter into *Bombyx mori* eggs according to the method of Tamara, et al. (Nature Biotechnology 18, 81-84, 2000), followed by breeding the hatched larva and crossing the resulting adult insects (G0) within the same group. Recombinant silkworms normally appear at a frequency of 1 to 2% among this G1 generation.

Selection of recombinant silkworms can be carried by PCR using primers designed based on the exogenous protein gene sequence after isolating DNA from the G1 generation silkworm tissue. Alternatively, recombinant silkworms can be easily selected by inserting a gene encoding green fluorescence protein coupled downstream from a promoter capable of being expressed in silkworm cells into a "gene cassette for inserting a gene" in advance, and then selecting those individuals that emit green fluorescence under ultraviolet light among G1 generation silkworms at first instar stage.

In addition, in the case of the micro-injection of a vector having a "gene cassette for inserting a gene" into *Bombyx mori* eggs for the purpose of acquiring recombinant silkworms containing a "gene cassette for expressing an exogenous protein" in their chromosomes, recombinant silkworms can be acquired in the same manner as described above by simultaneously micro-injecting a piggyBac transposase protein.

A piggyBac transposon refers to a transfer factor of DNA having an inverted sequences of 13 base pairs on both ends and an ORF inside of about 2.1 k base pairs. Although there are no particular limitations on the piggyBac transposon used in the present invention, examples of those that can be used include those originating in *Trichoplusia ni* cell line TN-368, *Autographa californica* NPV (AcNPV) and *Galleria mellonea* NPV (GmMNPV). A piggyBac transposon having gene and DNA transfer activity can be preferably prepared using plasmids pHA3PIG and pPIGA3GFP having a portion of a piggyBac originating in *Trichoplusia ni* cell line TN-368 (Nature Biotechnology 18, 81-84, 2000).

The structure of the DNA sequence originating in a piggyBac is required to have a pair of inverted terminal sequences containing a TTAA sequence, and has an exogenous gene such as a cytokine gene inserted between those DNA sequences. It is more preferable to use a transposase in order to insert an exogenous gene into silkworm chromosomes using a DNA sequence originating in a transposon. For example, the frequency at which a gene is inserted into silkworm chromosomes can be improved considerably by simultaneously inserting DNA capable of expressing a piggyBac transposase to enable the transposase transcribed and translated in the silkworm cells to recognize the two pairs of inverted terminal sequences, cut out the gene fragment between them, and transfer it to silkworm chromosomes.

The gene recombinant silkworm used in the present invention refers to a silkworm which has had inserted into its chromosomes an exogenous protein gene, and after treating the silkworm chromosomal DNA with restriction endonuclease in accordance with ordinary methods, yields a positive signal when subjected to Southern blotting using the exogenous protein gene labeled in accordance with ordinary methods as a probe. There are no particular limitations on the gene locus on the chromosome into which a cytokine gene has been inserted provided it is a site that does not inhibit silkworm development, differentiation and growth. The recombinant silkworm has the ability to produce exogenous protein in its silk gland cells, silk gland lumen and silk thread. In addition, the recombinant silkworm is able to develop and mate normally, stably retain the inserted exogenous protein gene, and transmit that gene to its offspring. Thus, the amount of exogenous protein produced can easily be increased by increasing the number of recombinant silkworms through crossing. Crossing between transgenic silkworm strain and non-transgenic strain can increase the amount of the produced exogenous protein. In this case, it is necessary to cross the silkworms while suitably selecting those silkworms into which the target exogenous protein gene has been inserted. In this case, offspring that have inherited the gene of the recombinant silkworm can be easily evaluated by analyzing a marker gene used to select the recombinant silkworms or the presence or structure of the exogenous protein gene by PCR or Southern blotting and so forth using cell DNA obtained from an arbitrary tissue.

Insect cells and silkworm silk glands containing the gene cassette for expression of an exogenous protein of the present invention can produce exogenous protein in culture supernatant or their cells by respectively culturing in culture liquid suitable for their culturing. For example, BmN cells, which are silkworm ovary cells that have been inserted with the expression gene cassette of the present invention, produce a target exogenous protein after 3 or 4 days of culturing by culturing at 27° C. in TC-100 medium (PharMingen). In addition, silkworm posterior silk gland produces exogenous protein by culturing at 25° C. in Grace's insect medium after being excised aseptically from, for example, fifth-instar larva. In the case of producing protein in silk glands, it is preferable to maintain a high dissolved oxygen concentration in the medium, and culture while removing low molecular weight factors that inhibit protein synthesis that accumulate in the medium by, for example, an ultrafiltration membrane since this allows protein synthesis to proceed for a long period of time.

A silk gland inserted with an exogenous protein gene fused to the 3' terminal of fibroin H chain gene of the present invention is capable of producing a large amount of a target exogenous protein in culture supernatant. Since nearly all contaminating proteins in the silk gland culture supernatant are fibroin, the target protein can be easily purified from the silk gland culture supernatant, and as a result, a highly pure target protein can be obtained.

The recombinant silkworm obtained in the present invention can be raised in the same manner as ordinary silkworms, and is able to produce exogenous protein by raising under ordinary conditions. The amount of exogenous protein produced can be improved by optimizing the temperature, humidity and feeding conditions, etc. during the fifth instar period in particular corresponding to the target exogenous protein.

A recombinant silkworm inserted with an exogenous protein gene fused to the 3' terminal of fibroin H chain gene of the present invention is able to produce a large amount of a target exogenous protein in its cocoon. The target exogenous protein can also be easily purified and recovered from the resulting cocoon. In addition, depending on the function of the exogenous protein produced, silk thread containing the resulting exogenous protein can be used directly or in a partially processed form in various industrial applications.

Exogenous protein can be obtained from the silk gland or cocoon and silk thread of a recombinant silkworm obtained in the present invention by a suitable extraction procedure. Although there are no particular limitations on the solvent used to extract exogenous protein from silk glands or cocoon and silk thread, an aqueous solvent system is preferable in many cases. An aqueous solution used for extraction may contain a suitable solute for promoting extraction of the exogenous protein, examples of which include inorganic acids such as phosphoric acid, organic acids such as acetic acid, citric acid and malic acid, salts such as sodium, chloride, urea, guanidine hydrochloride and calcium chloride, and polar organic solvents such as ethanol, methanol, acetonitrile and acetone. In addition, there are also no particular limitations on the pH of the extraction solution, and any arbitrary pH can be used provided it does not deactivate the function of the target exogenous protein.

There are no particular limitations on the method for isolating and purifying the extracted exogenous protein, and ordinary protein purification methods can be used. For example, a target useful protein can be purified and isolated by combining chromatography using a silica gel carrier, ion exchange carrier, gel permeation carrier, chelating carrier or pigment-loaded carrier and so forth, ultrafiltration, gel permeation, dialysis, de-salting by salting out or concentration and so forth using an inherently possessed function as an indicator. For example, feline interferon-ω can be recovered in the soluble fraction obtained by homogenizing silk glands or cocoon and silk thread of a silkworm into which has been inserted a feline interferon-ω gene with 20 mM phosphate buffer (pH 7.0). Moreover, the purity of the feline interferon-ω can be increased by adsorbing the resulting extract liquid onto, for example, a Blue Sepharose carrier and eluting the resulting buffer solution containing the extract liquid after washing.

Cytokines produced in this manner can be used in pharmaceutical applications as well as various measurement and diagnostic applications in the same manner as cytokines produced with other conventional production processes. In this case, they may also be used as a mixture to which various additives have been added. In addition, the tissue or cocoon and silk thread of a silkworm in which cytokines have been expressed can also be used directly or after processing as fibers For medical or clothing use. In addition, the tissue or silk thread of a recombinant silkworm in which enzymes have been expressed can be used directly in enzyme reactions.

EXAMPLES

Although the following provides a more detailed explanation of the present invention by indicating its examples, the present invention is not limited to the descriptions of these examples.

Reference Example

Method for Measuring Antiviral Activity

The physiological activity of interferon was measured according to the following method as antiviral activity.

Antiviral activity was measured by the CPE method using vesicular stomatitis virus (VSV) for the virus, and using feline Fc9 cells (J. K. Yamamoto, et al.: vet. Immunol. and Immunopathol., 11, 1-19, 1986) for the susceptive cells in the case of feline interferon-ω, or human FL cells in the case of human interferon-β. Namely, a sample diluent was added to the uppermost row of 96-well microtiter plate in which susceptive cells cultured at 37° C. to confluency, and then serially diluting in two-fold increments moving towards the lower end of the plate.

After culturing for 20 to 24 hours at 37° C., VSV was added followed by additionally culturing for 16 to 20 hours at 37° C. Viable susceptive cells adhered to the microtiter plate were then stained with crystal-violet stain containing 20% formalin, and as a result of measuring the optical absorbance at 570 nm for the amount of crystal-violet remaining on the microplate, antiviral activity was determined by comparison with a standard. Intercat (Toray) adjusted to 1000 units/ml with cell culturing medium was used for the standard for feline interferon-ω, while Feron (Toray) prepared to 1000 units/ml with cell culturing medium was used for the standard for human interferon-β. In addition, samples were used for the measurement of antiviral activity after diluting 15-fold with cell culturing medium.

Example 1

Preparation of *Bombyx mori* Genomic DNA

Fifth instar third day silkworms were dissected to remove posterior silk gland tissue. After washing with 1×SSC, 200 µl of DNA extraction buffer (50 mM Tris-HCl (pH 8.0), 1 mM EDTA (pH 8.0), 100 mM NaCl) were added. After adding Proteinase K (final concentration: 20 µg/ml) and adequately grinding up the tissue with a grinder, 350 µl of DNA extraction buffer and 60 µl of 10% SDS were added followed by incubating for 2 hours at 50° C. After adding 500 µl of Tris-HCl-saturated phenol (pH 8.0) and mixing for 10 minutes, the supernatant was recovered by centrifuging for 5 minutes at 4° C. and 10,000 rpm. After adding an equal volume of phenol/chloroform/isoamyl alcohol (25:24:1) to the supernatant and mixing, the resulting mixture was centrifuged. Phenol/chloroform/isoamyl alcohol was again added followed by centrifuging and recovery of the supernatant. After adding an equal volume of chloroform/isoamyl alcohol (24:1) and mixing, the mixture was centrifuged. Chloroform/isoamyl alcohol was again added to the resulting supernatant followed by centrifuging and recovery of the supernatant. $\frac{1}{10}$ volume 3 M sodium acetate (pH 5.2) was then added to the resulting supernatant and mixed and, after additionally adding 2.5 volumes of cold ethanol and allowing it to stand undisturbed for 30 minutes at -80° C., the mixture was centrifuged for 10 minutes at 4° C. and 15,000 rpm to precipitate genomic DNA. After washing the DNA precipitate with 70% ethanol, the precipitate was air-dried. The precipitate was then dissolved in sterile water containing RNase to 100 µg/ml to prepare a diluted genomic DNA solution.

Example 2

Gene Preparation

The genes used were acquired by PCR by producing primers for the sequences on both ends using known sequences and using suitable DNA sources for the templates. Restriction sites were added to the ends of the primers for the subsequent gene construction procedure.

Feline interferon-ω gene (base numbers 9-593 of GenBank registration no. S62636) was acquired by PCR using two types of primers consisting of primer 3 (SEQ. ID No. 3) and primer 4 (SEQ. ID No. 4) and using baculovirus rBNV100 encoding feline interferon-ω gene for the template. rBNV100 can be produced by, for example, cutting out FeIFN gene from a plasmid extracted from *E. coli*(pFeIFN1) (Patent Microorganism Depository No. 1633), coupling to a silkworm cloning vector (T. Horiuchi, et al., Agric. Biol. Chem., 51, 1573-1580, 1987), and co-transfecting silkworm established cells with the recombinant plasmid produced and silkworm nuclear polyhedrosis virus DNA.

Sericin-1 gene promoter (base numbers 599-1656 of GenBank registration no. AB007831) was acquired by PCR using two types of primers consisting of primer 5 (SEQ. ID No. 5) and primer 6 (SEQ. ID No. 6) and using silkworm chromosomal DNA for the template. Fibroin H chain gene promoter (base numbers 255-574 of GenBank registration no. V00094) was acquired by PCR using two types of primers consisting of primer 7 (SEQ. ID No. 7) and primer 8 (SEQ. ID No. 8) and using silkworm chromosomal DNA for the template. Bovine growth hormone gene poly A (pcDNA3.1(+) sequence numbers 1011-1253) was acquired by PCR using two types of primers consisting of primer 9 (SEQ. ID No. 9) and primer 10 (SEQ. ID No. 10) and using plasmid pcDNA3.1(+) vector (Invitrogen) for the template.

PCR was carried out in accordance with the accompanying protocol using KODplus (Toyobo). Namely, after adding 10 ng of each template in the case of a plasmid or 100 ng in the case of chromosomal DNA, 30 pmol of each primer and 10 μl of the 10×PCR buffer provided, each reagent was added to a concentration of 1 mM MgCl$_2$, 0.2 mM dNTPs and 2 units of KODplus followed by bringing up to a final volume of 100 μl. The PCR components were then reacted for 30 cycles using a Perkin-Elmer DNA thermal cycler under DNA denaturation conditions of 94° C. for 15 seconds, primer annealing conditions of 55° C. for 30 seconds, and elongation conditions of 68° C. for 30 to 60 seconds.

These reaction solutions were electrophoresed with 1 to 1.5% agarose gel, and DNA fragments consisting of a roughly 580 bp fragment in the case of feline interferon-ω gene, a roughly 1 kbp fragment in the case of sericin-1 promoter, a roughly 320 bp fragment in the case of fibroin H chain promoter, and a roughly 230 bp fragment in the case of bovine growth hormone poly A were extracted and purified in accordance with ordinary methods. After phosphorylating these DNA fragments with polynucleotide kinase (Takara Shuzo), they were ligated to pUC19 vector subjected to dephosphorylation treatment after being cleaved with HincII by reacting overnight at 16° C. using DNA Ligation Kit Ver. 2 (Takara Shuzo). These were then used to transform E. coli in accordance with ordinary methods and the resulting transformants were confirmed to contain the PCR fragments by performing PCR on the resulting colonies under the same conditions as previously described to prepare plasmids in which the PCR fragments were inserted according to ordinary methods. These plasmids were sequenced to confirm that the resulting fragments consisted of the base sequences of each gene.

Example 3

Production of Plasmids for Gene Insertion pigA3GFP (Nature Biotechnology 18, 81-84, 2000) was used for the plasmid for gene insertion. Namely, vector pigA3GFP is a vector in which after removing a region encoding transposase from plasmid p3E1.2 disclosed in U.S. Pat. No. 6,218,185, an A3 promoter (base numbers 1764-2595 of GenBank registration no. U49854), GFP originating in pEGFP-N1 vector (Clontech) and poly A addition sequence originating in SV40 (base numbers 659-2578 of GenBank registration no. U55762) are inserted into that portion (Nature Biotechnology 18, 81-84, 2000). The expression unit of feline interferon-ω gene was inserted at the XhoI site upstream from the A3 promoter. The expression units of the inserted genes consisted of a sericin-1 gene promoter-feline interferon-ω-bovine growth hormone poly A addition sequence (SEQ. ID No. 1), or a fibroin H chain gene promoter-feline interferon-ω-bovine growth hormone poly A addition sequence (SEQ. ID No. 2). The following provides a detailed description of the method.

Genes were cleaved from the plasmids prepared in Example 2 using the restrictase sites preset in the primers. Namely, insert fragments were cleaved using EcoRI and SalI in the case of sericin-1 gene promoter and fibroin H chain gene promoter, SalI and XbaI in the case of feline interferon-ω, and XbaI and BamHI in the case of bovine growth hormone poly A, followed by electrophoresing with 1 to 1.5% agarose gel and extracting and purifying the fragments in accordance with ordinary methods.

200 ng of sericin-1 gene fragment, 100 ng of feline interferon-ω gene fragment, and 50 ng of bovine growth hormone poly A were mixed and reacted overnight at 16° C. by adding an equal volume of DNA Ligation Kit Version 2 (Takara Shuzo). 0.5 μl of the reaction solution was subjected to PCR using primer 11 (SEQ. ID No. 11) and primer 12 (SEQ. ID No. 12) for 2 minutes of elongation under the same conditions as Example 2. These reaction solutions were electrophoresed with 1% agarose gel, and the amplified, roughly 1.9 kb, DNA fragment (SIB fragment) was extracted and purified in accordance with ordinary methods.

Similarly, 70 ng of fibroin H chain gene promoter fragment, 100 ng of feline interferon-ω gene fragment and 50 ng of bovine growth hormone poly A were mixed and reacted overnight at 16° C. by adding an equal volume of DNA Ligation Kit Version 2 (Takara Shuzo). 0.5 μl of the reaction solution was subjected to PCR using primer 13 (SEQ. ID No. 13) and primer 12 (SEQ. ID No. 12) for 2 minutes of elongation under the same conditions as Example 1. These reaction solutions were electrophoresed with 1% agarose gel, and the amplified roughly 1.5 kb DNA fragment (FIB fragment) was extracted and purified in accordance with ordinary methods.

Figure 2:
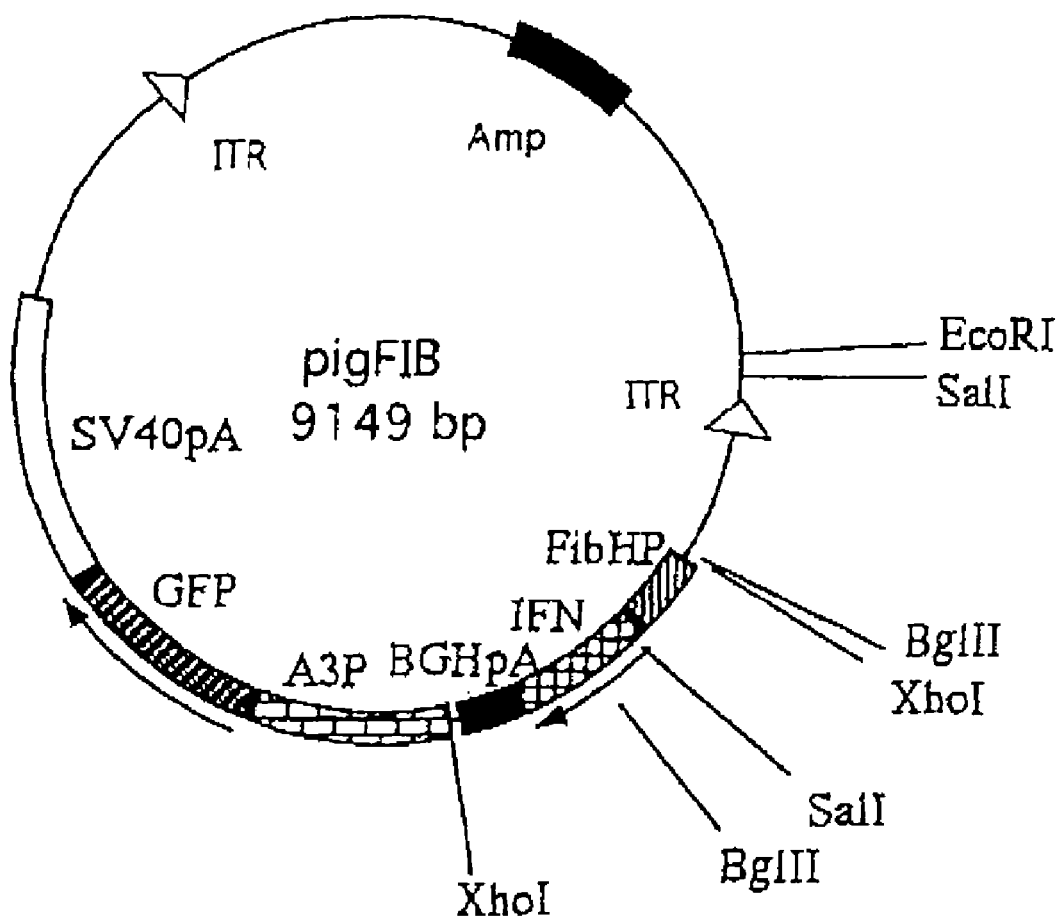
FIG. 2 is a drawing showing a restriction map of gene insertion vector pigFIB.

After digesting these fragments with XhoI, they were ligated to pigA3GFP and subjected to XhoI treatment and dephosphorylation treatment by reacting overnight at 16° C. using DNA Ligation Kit Ver. 2 (Takara Shuzo). The plasmid containing the SIB fragment was designated as pigSIB (FIG. 1), and the plasmid containing the FIB fragment was designated as pigFIB (FIG. 2), and these were purified by centrifuging twice using the cesium chloride method and then used in a gene insertion experiment.

Example 4

Production of Gene Recombinant Silkworms
(Fibroin H Chain Gene Promoter)

Figure 3:
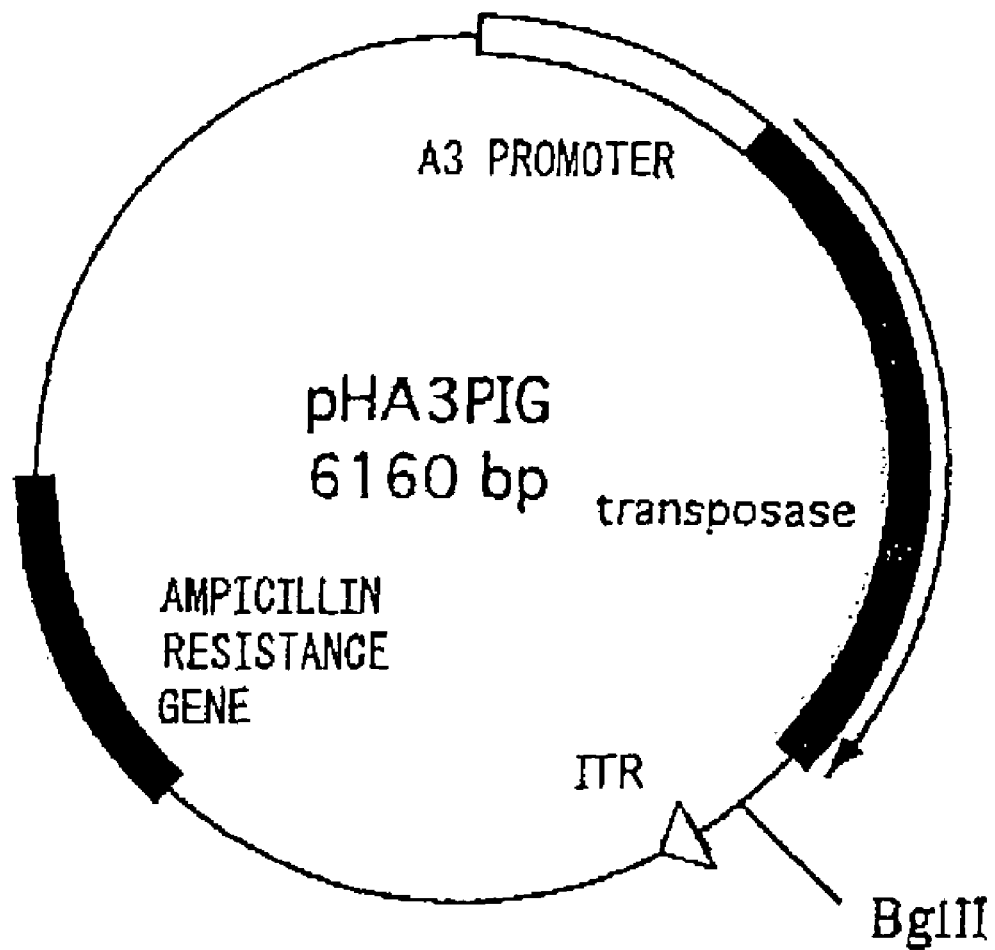
FIG. 3 is a drawing showing a restriction map of plasmid pHA3PIG having a transposase.

The aforementioned pigFIB and helper plasmid pHA3PIG (FIG. 3, Nature Biotechnology 18, 81-84, 2000) were adjusted to a concentration of 200 ng/ml each in 0.5 mM phosphate buffer (pH 7.0) and 5 mM KCl, after which 15 to 20 nl were micro-injected into silkworm eggs within 4 hours after being laid.

The larva that hatched from those silkworm eggs were raised, and the resulting adults (G0) were crossed within the same group. By observing the resulting first generation (G1) individuals with fluorescence of green fluorescence protein that had been simultaneously inserted with feline interferon-ω gene, those silkworms that contained the feline interferon-ω gene in their chromosomes were screened. The ratios of the moth groups in which silkworms containing the inserted gene were obtained are shown in Table 1. The silkworm eggs were injected twice, and gene recombinant silkworms were obtained from one moth group by the second injection.

TABLE 1

Acquisition Status of Gene Recombinant Silkworms
(Fibroin Heavy Chain Promoter)

| Experiment Group | No. of eggs injected | No. of eggs hatched | No. of adults | No. of sibling mated moths | No. of moth groups positive for feline interferon-ω gene |
|---|---|---|---|---|---|
| 1 | 1215 | 292 | 220 | 100 | 0 |
| 2 | 1326 | 374 | 250 | 123 | 1 |

Figure 4:
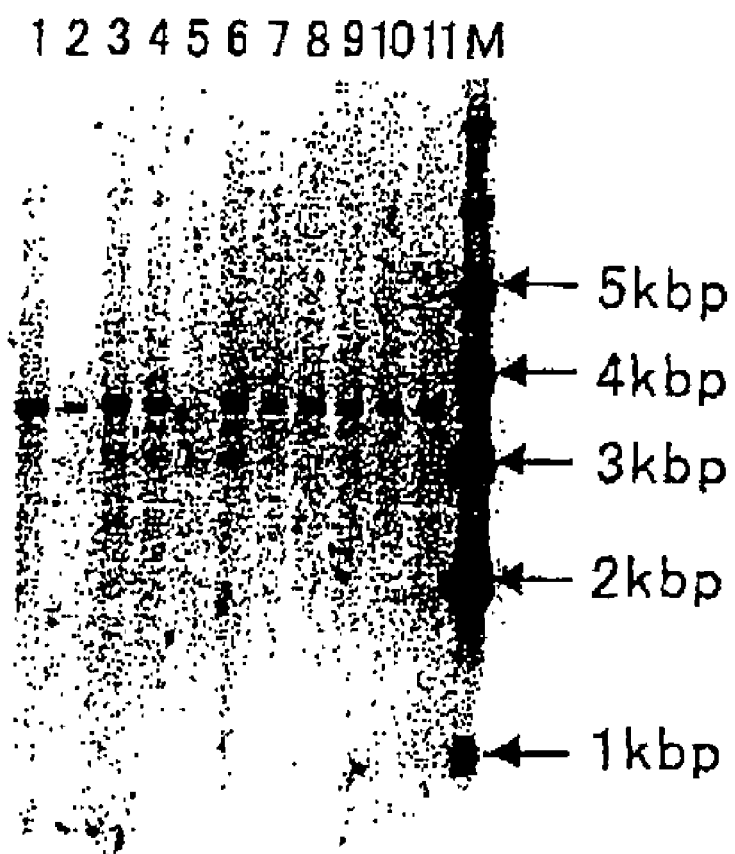
FIG. 4 is a drawing showing the results of treating the genomic DNA of 11 silkworms (G1) obtained from the positive moth groups of Table 1 with EcoRV and XmnI, followed by performing Southern blotting analysis using a feline interferon-ω gene as a probe.

The results of Southern blotting on the gene recombinant silkworms obtained from that moth group are shown in FIG. 4. The method employed for Southern blotting consisted of extracting chromosomal DNA from the G1 generation moths, electrophoresing restrictase-treated samples, and detecting a membrane to which the DNA was transferred by chemiluminescence using the AlkPhos Direct Labeling and Detection System (Amersham-Pharmacia) using a nucleic acid probe specific for feline interferon-ω.

When 11 G1 moths were investigated, feline interferon-ω gene was confirmed to have been inserted into 10 of the silkworms.

Example 5

Confirmation of Feline Interferon Production (Fibroin H Chain Promoter)

Figure 5:
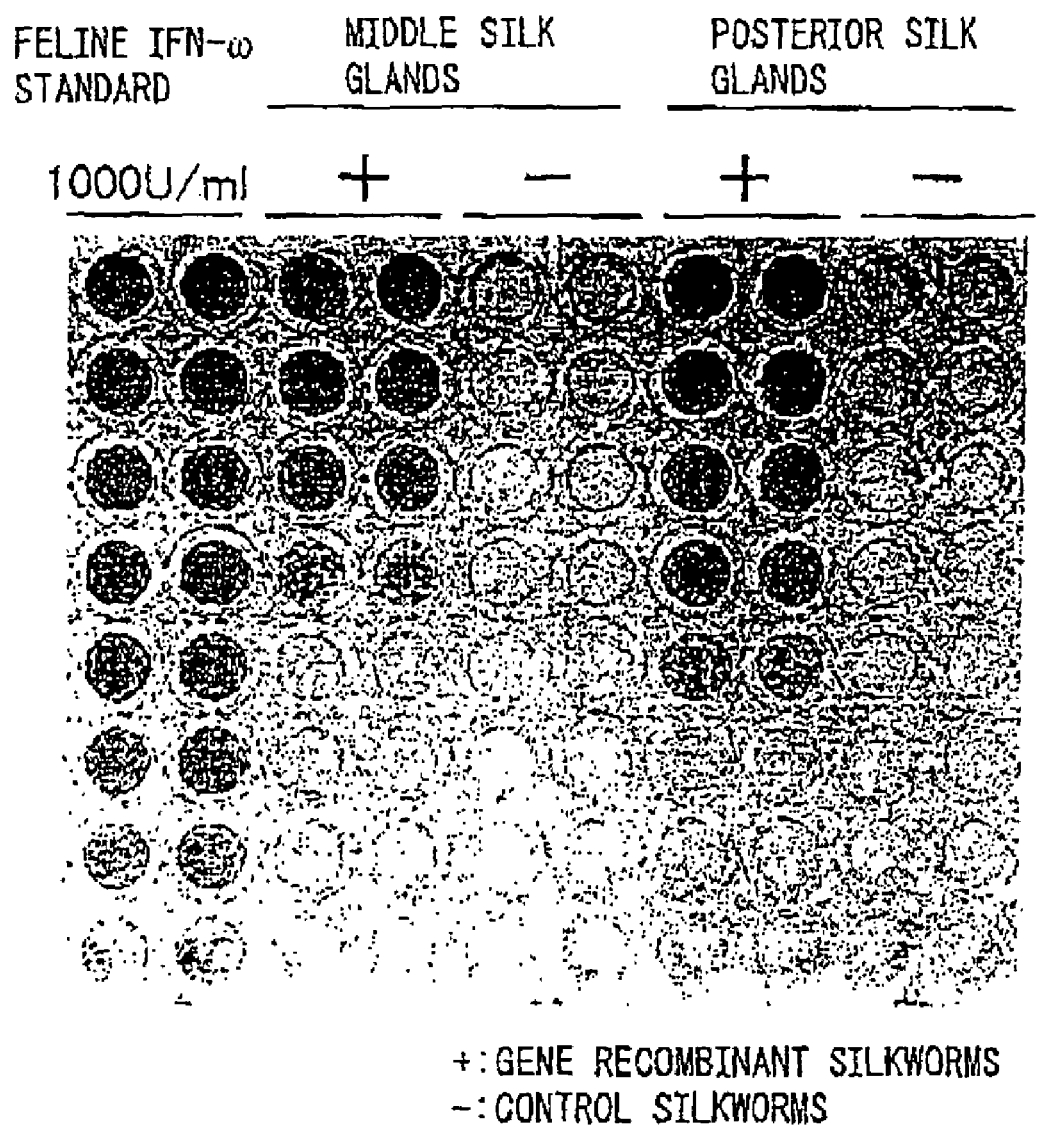
FIG. 5 is a drawing showing the antiviral activity of a silk thread extract of a recombinant silkworm into which was inserted feline interferon-ω gene coupled to fibroin H chain promoter. The sample in the dyed lane is shown to have activity.

Since feline interferon-ω has antiviral activity, the presence of feline interferon-ω can be determined according to its activity. Silkworms (G1) of the positive moth group obtained in Example 4 were mated with wild silkworms, and the middle and posterior silk glands excised from fifth instar larva of the resulting generation (G2) were confirmed to be inserted with feline interferon-ω gene. These were then homogenized using 20 mM sodium phosphate buffer (pH 7.0), and the resulting extract was measured using an antiviral activity measuring system that used feline cells. As a result, although antiviral activity was detected for both middle silk glands and posterior silk glands from the silk gland extracts of gene-containing silkworms, activity was not detected from the silk gland extracts of wild silkworms used as the control. Those results are shown in FIG. 5.

Feline interferon-ω is thought to mainly be expressed in posterior silk glands under the control of fibroin H chain promoter. It is believed to subsequently migrate into the middle and anterior silk glands in the same manner as fibroin, and the distribution of physiological activity is considered to coincide with this. On the other hand, there was no antiviral activity detected from silkworms into which the gene was not inserted. This clearly demonstrates that feline interferon-ω protein is expressed while retaining its physiological activity in silkworms into which feline interferon-ω gene has been inserted.

Example 6

Purification of Feline Interferon

Feline interferon was purified from the extract of posterior silk glands excised from G2 generation, fifth instar silkworms obtained in Example 5. 1 ml of extract was passed through a HiTrap Blue Sepharose column (Amersham-Pharmacia) followed by washing the column with 10 ml of 20 mM sodium phosphate buffer (pH 7.0). Continuing, the column was eluted with 10 ml of 20 mM sodium phosphate buffer (pH 8.0)-0.5 M NaCl and then with 10 ml of 20 m sodium phosphate buffer (pH 8.0)-1 M NaCl.

The washing fraction, 0.5 M elution fraction and 1 M elution fraction were collected, desalted and concentrated to about 1 ml. The results of determining the antiviral activity and amount of protein of the extract and each purified fraction are shown in Table 2.

TABLE 2

Purification of Feline Interferon-ω by Blue Sepharose Chromatography

|  | Antiviral activity (U/ml) | Amt. of protein (mg/ml) | Specific activity (U/mg) |
|---|---|---|---|
| Extracted sample | 523 | 0.37 | 1401 |
| Blank, washing fraction | 23 | 2.91 | 8 |
| 0.5 M NaCl elution fraction | 1494 | 0.85 | 1758 |
| 1 M NaCl elution fraction | >6270 | 0.41 | >15293 |

As a result of the purification procedure, antiviral activity, namely feline interferon-ω, could be recovered in the 1 M elution fraction, and its specific activity was roughly 10 times that of the extract.

Example 7

Production of Recombinant Gene Silkworms (Sericin-1 Promoter)

The aforementioned pigSIB and a helper plasmid were adjusted to a concentration of 200 ng/ml each in 0.5 mM phosphate buffer (pH 7.0) and 5 mM KCl, after which 15 to 20 nl were micro-injected into silkworm eggs within 4 hours after being laid. The larva that hatched from those silkworm eggs were raised, and the resulting adults (G0) were crossed within the same group. Insertion of feline interferon-ω gene into the chromosomes was investigated by observing the fluorescence of green fluorescence protein from the resulting first-generation (G1) individuals. In two experiments, a gene recombinant vector containing feline interferon-ω gene coupled to sericin promoter was micro-injected into 1218 and 1375 eggs, respectively, and 12 positive moth groups each were able to be obtained (Table 3).

TABLE 3

Acquisition Status of Gene Recombinant Silkworms (Sericin Promoter)

| Experiment Group | No. of eggs injected | No. of eggs hatched | No. of adults | No. of sibling mated moths | No. of moth groups positive for feline interferon-ω gene |
|---|---|---|---|---|---|
| 1 | 1218 | 500 | 320 | 158 | 12 |
| 2 | 1375 | 540 | 500 | 225 | 12 |

Figure 6:
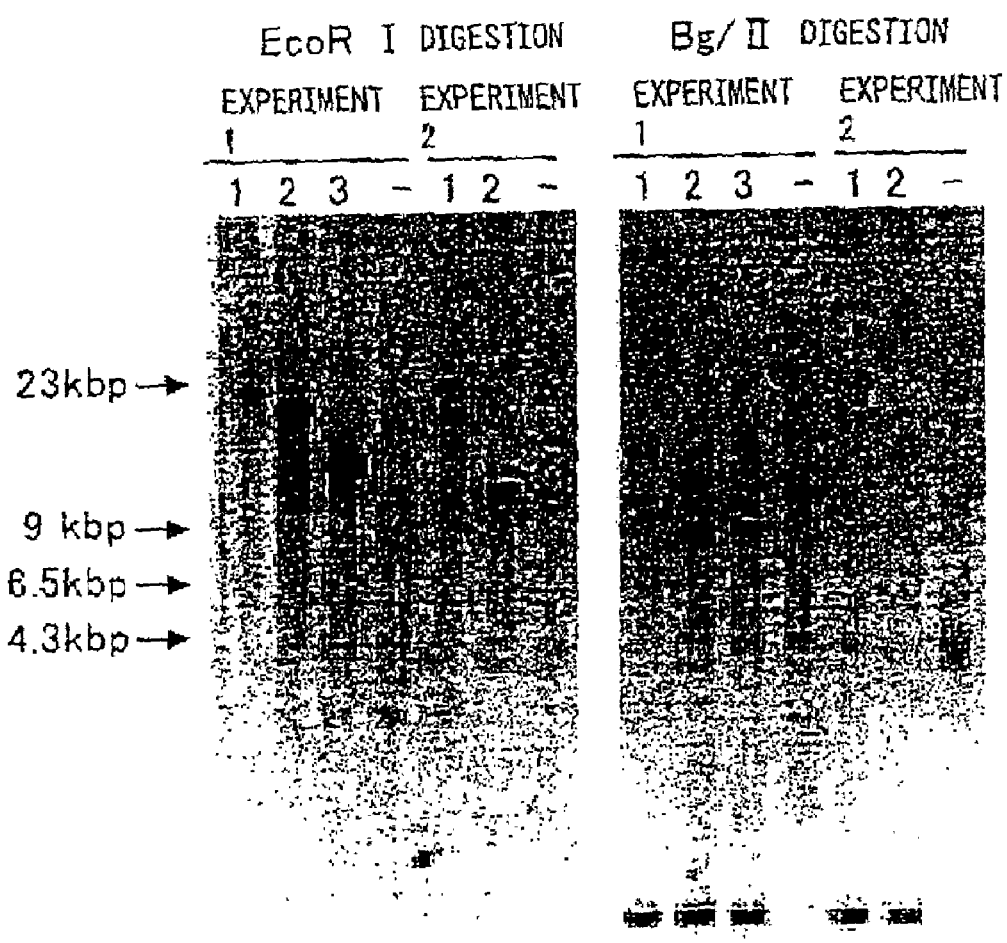
FIG. 6 is a drawing showing the results of treating silkworm silk gland genomic DNA obtained from the positive moth groups of Table 3 (3 moth groups from Experiment 1 and 2 moth groups from Experiment 2) with EcoRI or BglII followed by performing Southern blotting analysis using feline interferon-ω gene as a probe.

One silkworm (G1) each that was confirmed to contain the gene was selected from 3 moths groups in the first experiment and 2 moth groups in the second experiment among the resulting positive moth groups, and genomic DNA was extracted from their silk glands. After treating with EcoRI or BglII, Southern blotting analysis was performed on the DNA using feline interferon-ω gene as a probe. Those results are shown in FIG. 6. As a result, feline interferon-ω gene was confirmed to be inserted in the genomes of all silkworms. In addition, the site at which the gene was inserted into the genome was determined to be different depending on the moth group due to differences in the detected signal size.

Figure 7:
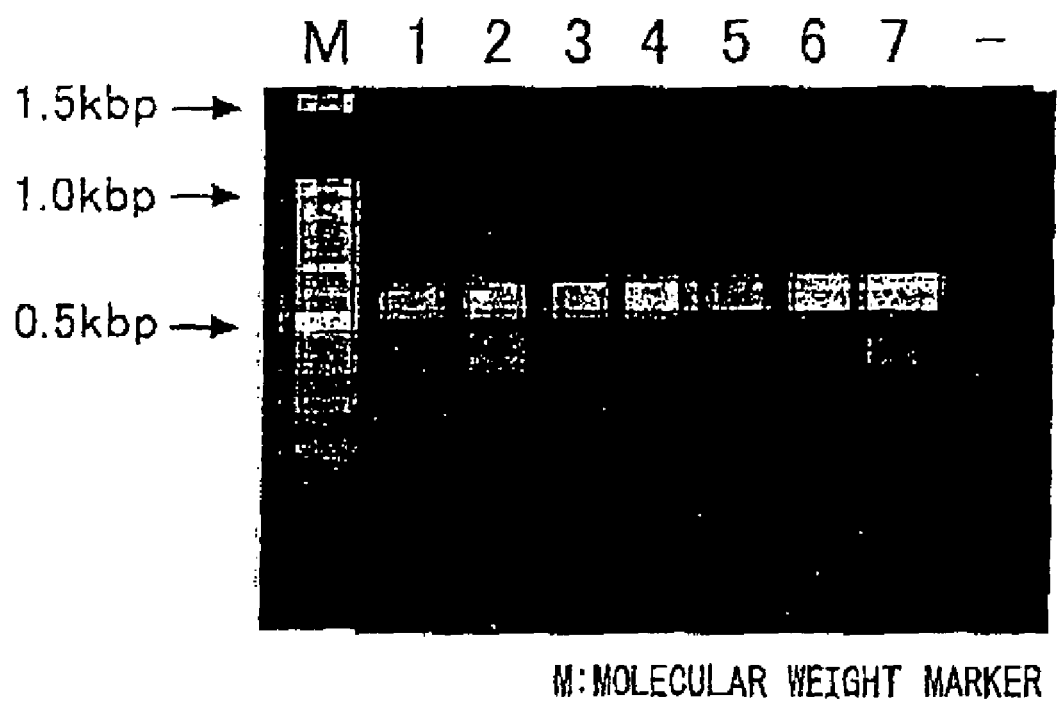
FIG. 7 is a drawing of the detection of expression of feline interferon mRNA in a middle silk thread of a gene recombinant silkworm by RT-PCR.

Next, mRNA expression of feline interferon-ω gene was investigated. Seven G1 silkworms confirmed to contain feline interferon-ω gene by Southern blotting were randomly selected, their mRNA was extracted and the expression of feline interferon-ω gene mRNA was investigated by RT-PCR. Isogen (Nippon Gene) and Oligodex dT-30 (Roche Diagnostics) were used for mRNA extraction and purification, the Ready-To-Go T-Primed First-Strand Kit (Amersham-Pharmacia) was used for cDNA synthesis, and the procedure was carried out according to the protocol provided with the kit. As a result of carrying out PCR under the same conditions as during the acquisition of feline interferon-ω gene of Example 2, expression of feline interferon-ω gene mRNA was confirmed for all of the silkworms (FIG. 7).

Example 8

Figure 8:
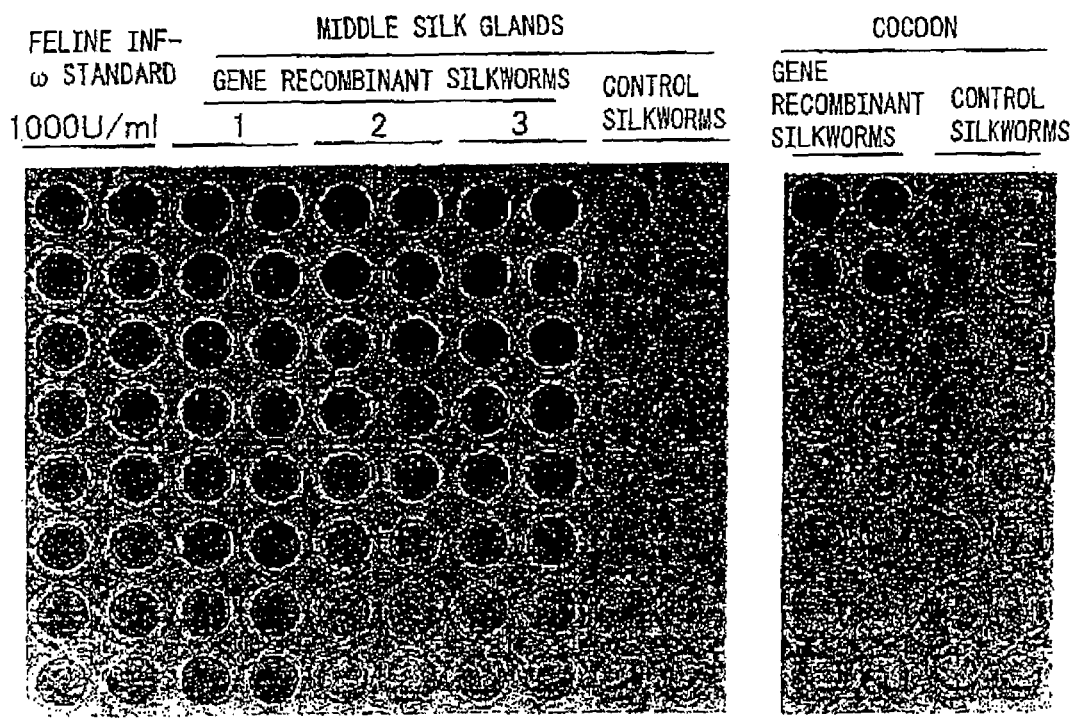
FIG. 8 is a drawing showing the antiviral activity of a middle silk gland extract and a cocoon and silk thread extract of a recombinant silkworm into which was inserted feline interferon-ω gene coupled to a sericin promoter. The sample in the dyed lane is shown to have activity.

Confirmation of Feline Interferon Production in Middle Silk Glands and Cocoon and Silk Thread The middle silk glands were excised from three gene recombinant silkworms obtained in Example 7 and one wild silkworm followed by homogenizing using 20 mM sodium phosphate buffer (pH 7.0) and centrifuging to prepare extracts. In addition, one cocoon each from the gene recombinant silkworms and wild silkworm were extracted in the same manner. When these extracts were measured for their antiviral activity, antiviral activity was detected in the middle silk glands of all of the gene recombinant silkworms, but was not detected in the silk glands of the wild silkworm. Moreover, antiviral activity was also detected in the cocoons of the gene recombinant silkworms (FIG. 8).

On the basis of these findings, feline interferon-ω was determined to be expressed in gene recombinant silkworms while retaining its physiological activity, and that activity was determined to remain in the silk thread.

Example 9

Production of Plasmids for Insertion of Human Interferon-β Gene

Production of plasmids for insertion of human interferon-β gene was carried out according to the same method as the case of feline interferon-ω gene indicated in Examples 2 through 4.

Namely, PCR was carried out using primer 14 (SEQ. ID No. 14) and primer 15 (SEQ. ID No. 15) and using plasmid pORF-hIFN-β encoding human interferon-β gene as a template to obtain a human interferon-β gene fragment. After treating this fragment with restriction endonucleases SalI and XbaI, a plasmid was constructed that contained a gene expression sequence in which fibroin H chain gene promoter was coupled to the 5' terminal or poly A signal originating in bovine growth hormone gene was coupled to the 3' terminal (fibroin H chain promoter-human interferon-β gene-bovine growth hormone gene poly A signal (FhIB): SEQ. ID No. 16, sericin gene promoter-human interferon-β-bovine growth hormone gene poly A signal (ShIB); SEQ. ID No. 17).

The aforementioned FhIB and ShIB sequences for gene expression were then respectively cleaved from these plasmids by treating with XhoI, and coupled to pigA3GFP that had been subjected to dephosphorylation treatment after being cleaved with XhoI. The plasmid containing the FhIB fragment was designated as pigFhIB, while the plasmid that contained the ShIB fragment was designated as pigShIB. These fragments were purified by centrifuging twice according to the cesium chloride method and then used in a gene insertion experiment.

Example 10

Production of Human Interferon-β Gene Recombinant Silkworms

Production of human interferon-β gene recombinant silkworms was carried out according to the same method used to produce feline interferon-ω gene recombinant silkworms indicated in Example 4 by using the gene insertion plasmids produced in Example 9.

Namely, pigFhIB and pigShIB were respectively microinjected into silkworm eggs together with helper plasmid pHA3PIG, and the resulting adults were crossed followed by screening of the next generation. When each plasmid was injected into 600 eggs, silkworms positive for green fluorescence were obtained in 7 moth groups for silkworms containing pigFhIB and in 5 moth groups for silkworms containing pigShIB, and insertion of the genes into their chromosomes was confirmed by PCR. The silk glands and silk thread were harvested from these silkworms and their extracts were used to measure the physiological activity of human interferon-β in the form of their antiviral activity. The values are shown in the table after having been corrected for total protein concentrations in the samples.

TABLE 4

Antiviral Activity in Tissue Extracts of Human Interferon-β Gene Recombinant Silkworms

| Promoter | Moth group no. - Individual no. | Antiviral activity (units/g protein) | | |
|---|---|---|---|---|
| | | Posterior silk glands | Middle silk glands | Silk thread |
| Fibroin H chain | 3-1 | 599723 | 82591 | Not tested |
| | 3-2 | 656110 | 41545 | |
| | 11-1 | 502750 | 19859 | |
| | 11-2 | 115560 | 39130 | |
| Sericin | 1-1 | Not tested | 53884 | 42187 |
| | 1-2 | | 648953 | 101713 |
| | 5-1 | | 437291 | 133288 |
| | 5-2 | | 541106 | 92749 |
| Normal silkworms | | Not detected | Not detected | Not detected |

Detection limit. Approx. 1000 units/g protein.

As a result, since antiviral activity was detected from the posterior and middle silk glands of the silkworms inserted with pigFhIB and antiviral activity was detected from the middle silk glands and silk thread of the silkworms inserted with pigShIB, interferon-β was confirmed to be produced in the silk gland tissue of these silkworms.

Example 11

Production of Plasmids for Insertion of Feline Granulocyte Colony Stimulating Factor Gene Production of plasmids for insertion of feline granulocyte colony stimulating factor gene was carried out according to the same method as the case of feline interferon-ω gene indicated in Examples 2 through 4.

Feline granulocyte colony stimulating factor gene was obtained in the form of a feline granulocyte colony stimulating factor gene fragment by carrying out PCR using primer 18 (SEQ. ID No. 18) and primer 19 (SEQ. ID No. 19) from cDNA obtained from CRFK cells stimulated for 24 hours with LPS at 10 μg/ml according to the report of Yamamoto, et al. (Gene, 274, 263-269, 2001). After treating this fragment with SalI and XbaI, plasmids were constructed that contained a sequence for gene expression in which fibroin H chain gene promoter or sericin gene promoter was coupled to the 5' terminal or poly A signal originating in bovine growth hormone gene was coupled to the 3' terminal (fibroin H chain promoter-feline granulocyte colony stimulating factor gene-bovine growth hormone gene poly A signal (FGB): SEQ. ID No. 20, sericin gene promoter-feline granulocyte colony stimulating factor gene-bovine growth hormone gene poly A signal (SGB): SEQ. ID No. 21).

The aforementioned FGB and SGB sequences for gene expression were then respectively cleaved from these plasmids by treating with XhoI, and coupled to pigA3GFP that had been subjected to dephosphorylation treatment after being cleaved with XhoI. The plasmid containing the FGB fragment was designated as pigFGB, while the plasmid that contained the SGB fragment was designated as pigSGB. These fragments were purified by centrifuging twice according to the cesium chloride method and then used in a gene insertion experiment.

Example 12

Production of Feline Granulocyte Colony Stimulating Factor Gene Recombinant Silkworms Production of feline granulocyte colony stimulating factor gene recombinant silkworms was carried out according to the same method used to produce feline interferon-ω gene recombinant silkworms indicated in Example 4 by using the gene insertion plasmids produced in Example 11.

Namely, pigFhIB and pigShIB were respectively microinjected into silkworm eggs together with helper plasmid pHA3PIG, and the resulting adults were crossed followed by screening of the next generation. When each plasmid was injected into 600 eggs, silkworms positive for green fluorescence were obtained in 3 moth groups for silkworms containing pigFGB and in 7 moth groups for silkworms containing pigSGB, and insertion of the genes into their chromosomes was confirmed by PCR. The silk glands and silk thread were harvested from these silkworms and their extracts were used to measure the physiological activity of feline granulocyte colony stimulating factor in the form of growth promoting activity of NFS-60 cells (ATCC).

Measurement of growth promoting activity was carried out in the manner described below. First, NFS-60 cells were seeded in a 96-well plate in the absence of M-CSF at 2×10⁴ cells/well followed 30 minutes later by the addition of 10 μl of sample. After culturing for an additional 24 hours, cell growth activity was measured using the Cell Counting Kit-8 (Dojindo). The amount of sample that yielded 50% of the maximum growth promoting effect (ED50) was defined as 1 unit/ml, and the physiological activity in the sample was calculated by multiplying by the dilution factor. The values are shown in the table after having been corrected for total protein concentrations in the samples.

TABLE 5

Growth Promoting Activity in Tissue Extracts of Feline Granulocyte Colony Stimulating Factor Gene Recombinant Silkworms

| Promoter | Moth group no. - Individual no. | Growth promoting activity (units/g protein) | | |
|---|---|---|---|---|
| | | Posterior silk glands | Middle silk glands | Silk thread |
| Fibroin H chain | 9-1 | 36 | Not detected | Not tested |
| | 9-2 | 412 | | |
| | 16-1 | 326 | 113 | |
| | 16-2 | 4039 | 226 | |
| | | | 53 | |
| Sericin | 3-1 | Not tested | 4330 | 590 |
| | 3-2 | | 2277 | 524 |
| | 8-1 | | 3966 | 846 |
| | 8-2 | | 2137 | 211 |
| Normal Silkworms | | Not detected | Not detected | Not detected |

Detection limit; Approx. 20 units/g protein.

As a result, as growth promoting activity was detected from the posterior and middle silk glands of the silkworms inserted with pigFGB and growth promoting activity was detected from the middle silk glands and silk thread of the silkworms inserted with pigSGB, feline granulocyte colony stimulating factor was confirmed to be produced in the silk gland tissue of these silkworms.

Example 13

Gene Preparation

A study was conducted on improving production amounts in silk gland tissue and silk thread using feline interferon-ω as a model of a physiologically active protein.

The genes used were acquired by PCR by producing primers for the sequences on both ends using known sequences and using suitable DNA sources for the templates. Restrictase sites were added to the ends of the primers for subsequent gene manipulation.

Fibroin H chain promoter (base numbers 62118-62437 of GenBank registration no. AF226688: to be referred to as the P region) was acquired by PCR using two types of primers consisting of primer 25 (SEQ. ID No. 25) and primer 26 (SEQ. ID No. 26) and using Bombyx mori genomic DNA for the template.

Fibroin H chain promoter-fibroin H chain gene first exon-first intron-second exon region (base numbers 62118-63513 of GenBank registration no. AF226688: to be referred to as the HP region) was acquired by using two types of primers consisting of primer 25 (SEQ. ID No. 25) and primer 31 (SEQ. ID No. 31) and using Bombyx mori genomic DNA for the template.

Fibroin H chain upstream promoter-fibroin H chain gene first exon-first intron region (base numbers 57444-62927 of GenBank registration no. AF226688: to be referred to as the HUP region) was acquired by PCR using two types of primers consisting of primer 33 (SEQ. ID No. 33) and primer 34 (SEQ. ID No. 34) and using Bombyx mori genomic DNA for the template.

Feline interferon-ω gene (base numbers 9-593 of GenBank registration no. S62636: to be referred to as the IC region) was acquired by PCR using two types of primers consisting of primer 27 (SEQ. ID No. 27) and primer 28 (SEQ. ID No. 28) and using baculovirus rBNV100, which encodes feline interferon-ω gene, for the template. rBNV100 can be produced by, for example, cutting out feline interferon-ω gene from a plasmid extracted from *E. coli* (pFeIFN1) (Patent Microorganism Depository No. 1633), coupling to a silkworm cloning vector (T. Horiuchi, et al., Agric. Biol. Chem., 51, 1573-1580, 1987), and co-transfecting silkworm established cells with the recombinant plasmid produced and silkworm nuclear polyhedrosis virus DNA.

Fibroin H chain poly A signal region (base numbers 79201-79995 of GenBank registration no. AF226688: to be referred to as the A region) was acquired by PCR using two types of primers consisting of primer 29 (SEQ. ID No. 29) and primer 30 (SEQ. ID No. 30) and using *Bombyx mori* genomic DNA for the template.

Fibroin H chain C terminal region gene-fibroin H chain poly A signal region (base numbers 79099-79995 of GenBank registration no. AF226688: to be referred to as the HA region) was acquired by PCR using two types of primers consisting of primer 32 (SEQ. ID No. 32) and primer 30 (SEQ. ID No. 30) and using *Bombyx mori* genomic DNA for the template.

β-galactosidase (β-gal) gene was acquired by PCR using two types of primers consisting of primer 37 (SEQ. ID No. 37) and primer 38 (SEQ. ID No. 38) and using pβgal-Basic vector (Clontech) for the template.

PCR was carried out in accordance with the accompanying protocol using KODplus (Toyobo). Namely, after adding 100 ng of each template in the case of *Bombyx mori* genomic DNA or 10 ng in the case of *Bombyx mori* posterior silk gland cDNA and pβgal-Basic vector, 50 pmol of each primer and 10 μl of the 10×PCR buffer provided, each reagent was added to a concentration of 1 mM $MgCl_2$, 0.2 mM dNTPs and 2 units of KODplus followed by bringing to a final volume of 100 μl. The PCR components were then reacted for 30 cycles using a Perkin-Elmer DNA thermal cycler under DNA denaturation conditions of 94° C. for 15 seconds, primer annealing conditions of 55° C. for 30 seconds, and elongation conditions of 68° C. for 60 to 300 seconds.

These reaction solutions were electrophoresed with 1 to 1.5% agarose gel, and a DNA fragment of roughly 0.3 kbp in the P region, roughly 1.4 kbp in the HP region, roughly 5.5 kbp in the HUP region, roughly 580 bp in the IC region, roughly 0.8 bp in the A region, roughly 0.9 bp in the HA region and roughly 3.2 kbp in the β-gal gene were extracted and prepared in accordance with ordinary methods. After phosphorylating these DNA fragments with polynucleotide kinase (Takara Shuzo), they were ligated to pUC19 vector subjected to dephosphorylation treatment after being cleaved with HincII by reacting overnight at 16° C. using DNA Ligation Kit ver. 2 (Takara Shuzo). These were then used to transform *E. coli* in accordance with ordinary methods and the resulting transformants were confirmed to be inserted with PCR fragments by performing PCR on the resulting colonies under the same conditions as previously described to prepare plasmids in which the PCR fragments were inserted according to ordinary methods. These plasmids were sequenced to confirm that the resulting fragments consisted of the base sequences of each gene.

Example 14

Production of Plasmids for Expression of β-Galactosidase

The plasmid retaining β-gal gene prepared in Example 13 was cleaved with SalI and HindIII followed by insertion therein of a roughly 0.3 kbp fragment (P region) cleaved by SalI and HindIII from a plasmid retaining fibroin H chain promoter. Moreover, this was then cleaved with BamHI followed by insertion therein of a roughly 0.8 kbp region (A region) cleaved with BamHI from a plasmid having a fibroin H chain poly A signal region, and purifying the resulting plasmid retaining the β-gal gene using the Qiagen Plasmid Maxi Kit in accordance with the protocol provided. The resulting plasmid was named pPga1A, and it was confirmed to be the target plasmid by PCR and sequencing.

Similarly, the plasmid retaining the β-gal gene prepared in Example 13 was cleaved with SalI and HindIII followed by insertion therein of a roughly 1.4 kbp fragment (HP region) cleaved with SalI and HindIII from a plasmid retaining the fibroin H chain promoter-fibroin H chain gene first exon-first intron-second exon region. Moreover, this was then cleaved with BamHI followed by insertion therein of a roughly 0.9 kbp fragment (HA region) cleaved with BamHI from a plasmid retaining a fibroin H chain C terminal region-fibroin H chain poly A signal region, and purifying the resulting plasmid retaining the β-gal gene using the Qiagen Plasmid Maxi Kit in accordance with the protocol provided. The resulting plasmid was named pHPgalHA, and it was confirmed to be the target plasmid by PCR and sequencing.

Example 15

Production of Plasmids for Gene Insertion pigA3GFP (Nature Biotechnology 18, 81-84, 2000) was used for the plasmid for gene insertion. Namely, vector pigA3GFP is a vector in which after removing a region encoding transposase from plasmid p3E1.2 disclosed in U.S. Pat. No. 6,218,185, an A3 promoter (base numbers 1764-2595 of GenBank registration no, U49854), GFP originating in pEGFP-N1 vector (Clontech) and poly A addition sequence originating in SV40 (base numbers 659-2578 of GenBank registration no. U55762) are inserted into that portion. The XhoI site located upstream from the A3 promoter was blunt ended followed by insertion of an expression cassette of feline interferon-ω gene. The constitution of the gene expression cassette used in the present example consisted of fibroin H chain promoter-feline interferon-O-fibroin H chain C terminal region-fibroin H chain poly A signal region (HP-IC-HA), or fibroin H chain upstream promoter-fibroin H chain gene first exon-first intron-second exon region-feline interferon-ω-fibroin H chain C terminal region-fibroin H chain poly A signal region (HUP-IC-HA), or fibroin H chain promoter-fibroin H chain gene first exon-first intron-second exon region-feline interferon-ω-fibroin H chain poly A signal region (HP-IC-A).

The following indicates the specific method employed.

Figure 9:
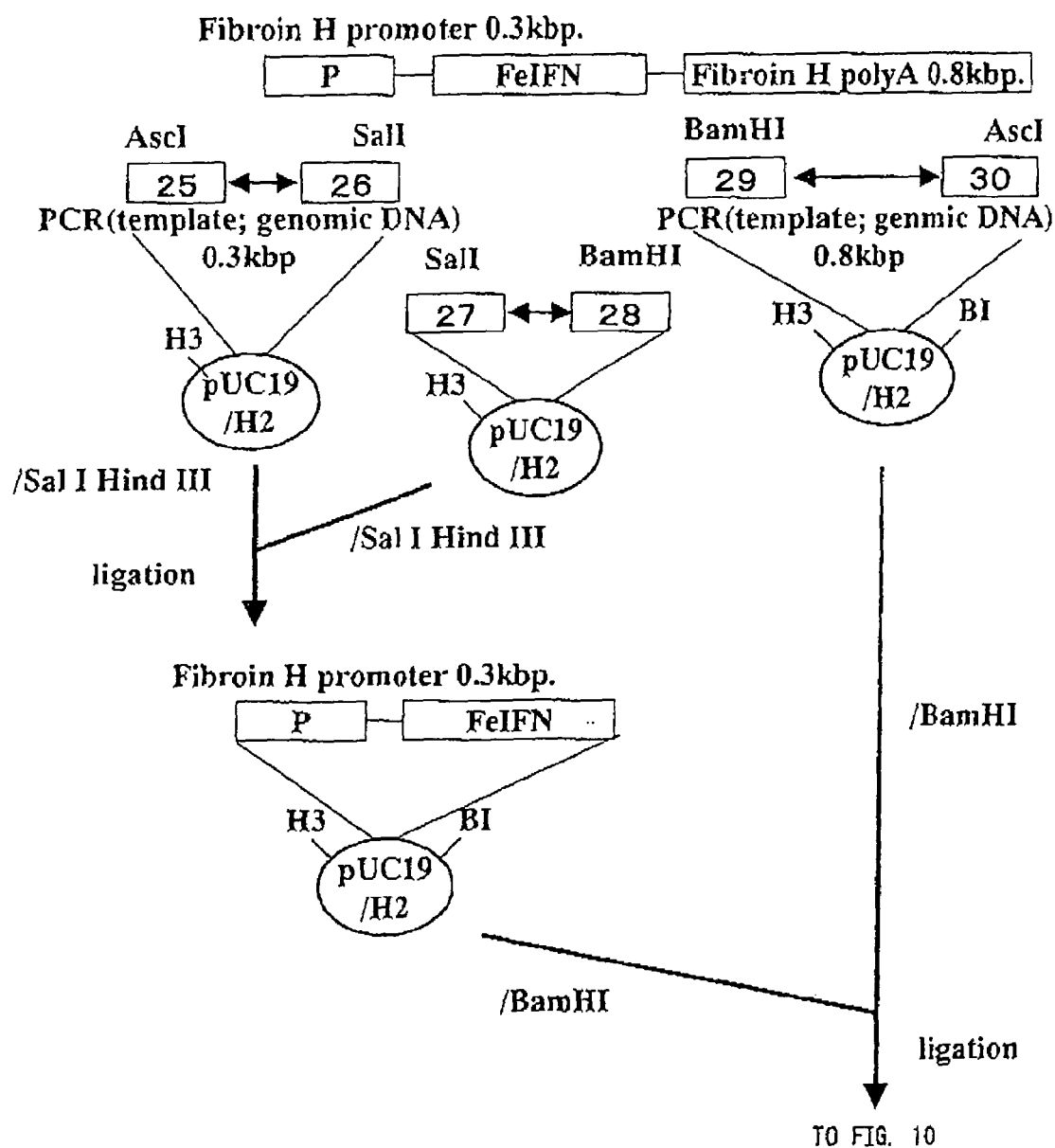
FIG. 9 is a drawing showing the procedure for producing a construct for gene insertion containing a P-IC-A gene cassette (first half).
Figure 10:
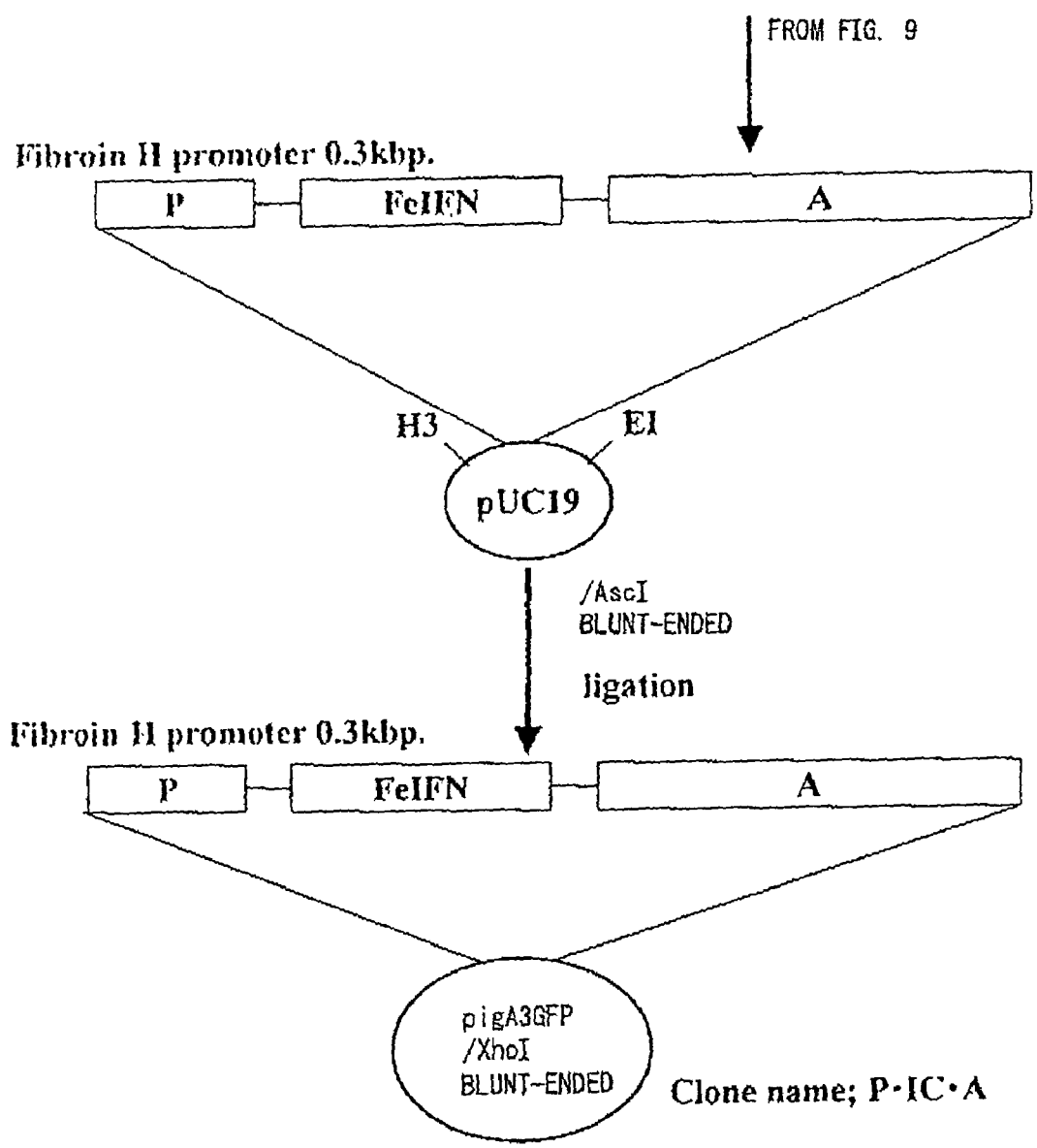
FIG. 10 is a drawing showing the procedure for producing a construct for gene insertion containing a P-IC-A gene cassette (second half).

The P-IC-A construct was produced according to the following procedure. The plasmid retaining feline interferon-ω (IC region) prepared in Example 13 was cleaved with SalI and HindIII followed by insertion therein of a roughly 0.3 kbp fragment (P region) cleaved with SalI and HindIII from a plasmid retaining fibroin H chain promoter. Moreover, this was cleaved with BamHI followed by insertion therein of a roughly 0.8 kbp fragment (region A) cleaved with BamHI from a plasmid retaining fibroin H chain poly A signal region. This plasmid retaining P, IC and A was cleaved with AscI and the cleaved roughly 1.7 kbp fragment was blunt ended with T4 DNA Polymerase (Takara Shuzo) and coupled to blunt ended and dephosphorylated pigA3GFP XhoI site to produce a construct for gene insertion containing the P-IC-A gene cassette. The procedure is shown in FIGS. 9 and 10.

Figure 11:
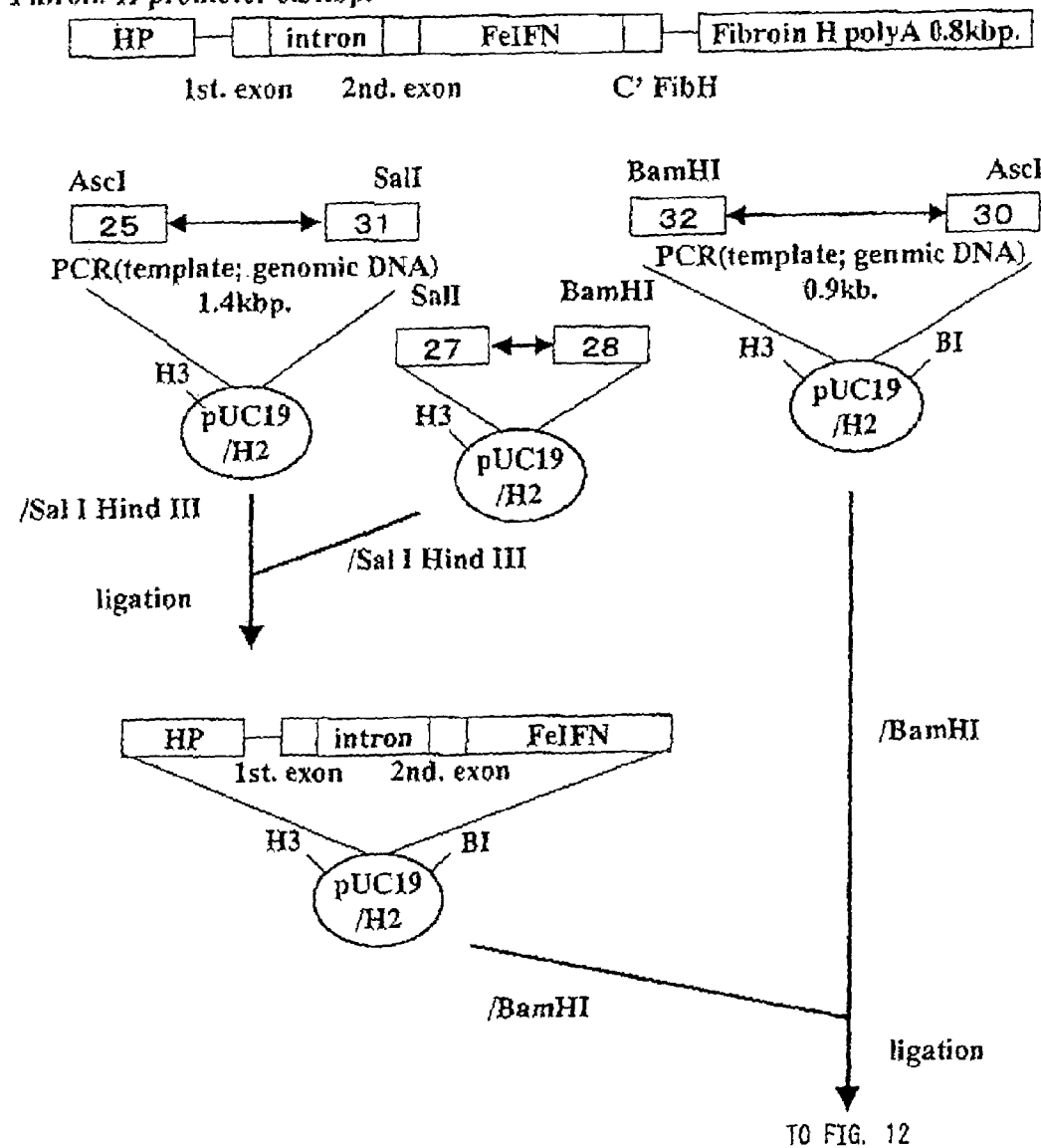
FIG. 11 is a drawing showing the procedure for producing a construct for gene insertion containing an HP-IC-HA gene cassette (first half).
Figure 12:
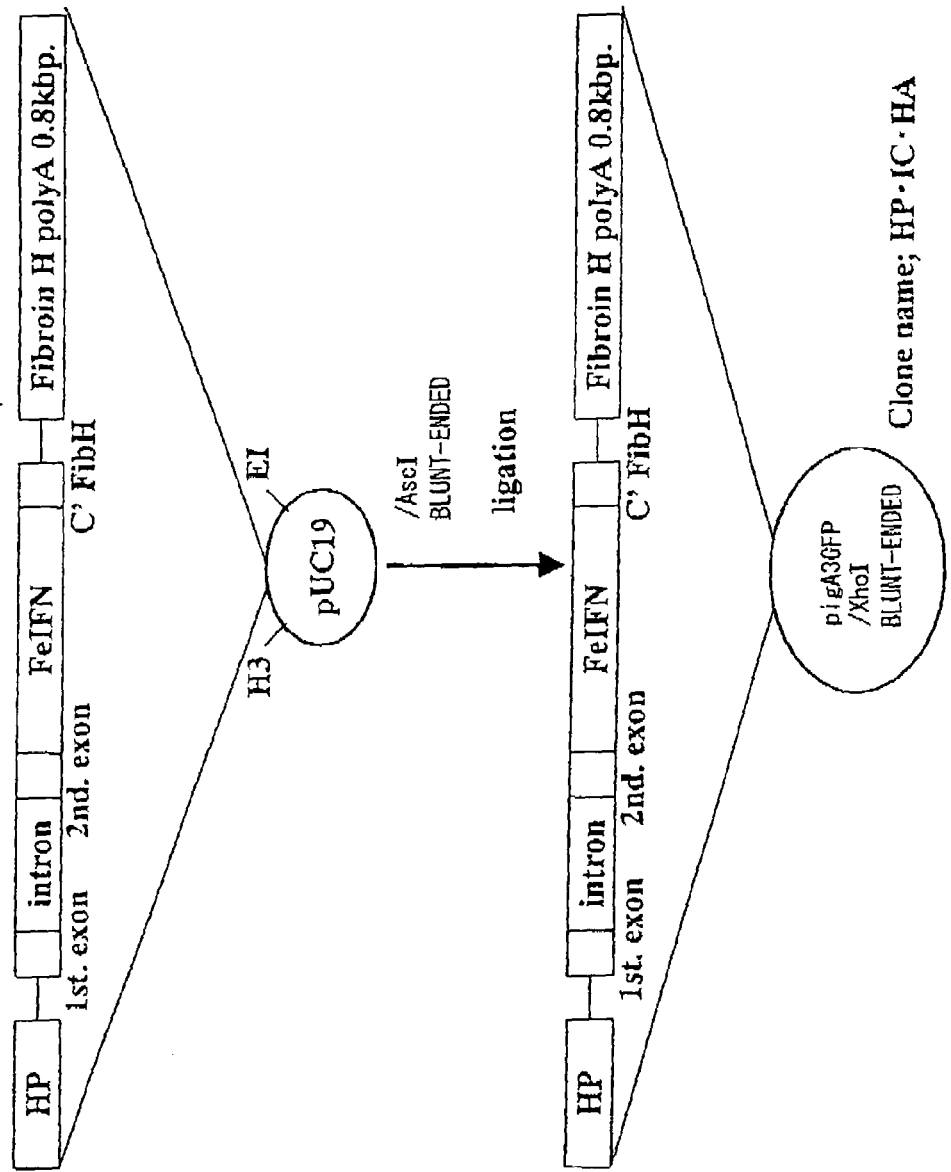
FIG. 12 is a drawing showing the procedure for producing a construct for gene insertion containing an HP-IC-HA gene cassette (second half).

The HP-IC-HA construct was produced in the following manner. The plasmid retaining feline interferon-ω (IC region) prepared in Example 13 was cleaved with SalI and HindIII followed by insertion therein of a roughly 1.4 kbp fragment (HP region) cleaved with SalI and HindIII from a plasmid retaining a fibroin H chain promoter-fibroin H chain gene first exon-first intron-second exon region. Moreover, this was cleaved with BamHI followed by insertion therein of a roughly 0.9 kbp fragment (region HA) cleaved with BamHI from a plasmid retaining fibroin H chain C terminal region-fibroin H chain poly A signal region. This plasmid retaining HP, IC and HA was cleaved with AscI and the cleaved roughly 2.9 kbp fragment was blunt ended with T4 DNA Polymerase (Takara Shuzo) and coupled to blunt ended and dephosphorylated pigA3GFP XhoI site to produce a construct for gene insertion containing the HP-IC-HA gene cassette. The procedure is shown in FIGS. 11 and 12.

Figure 13:
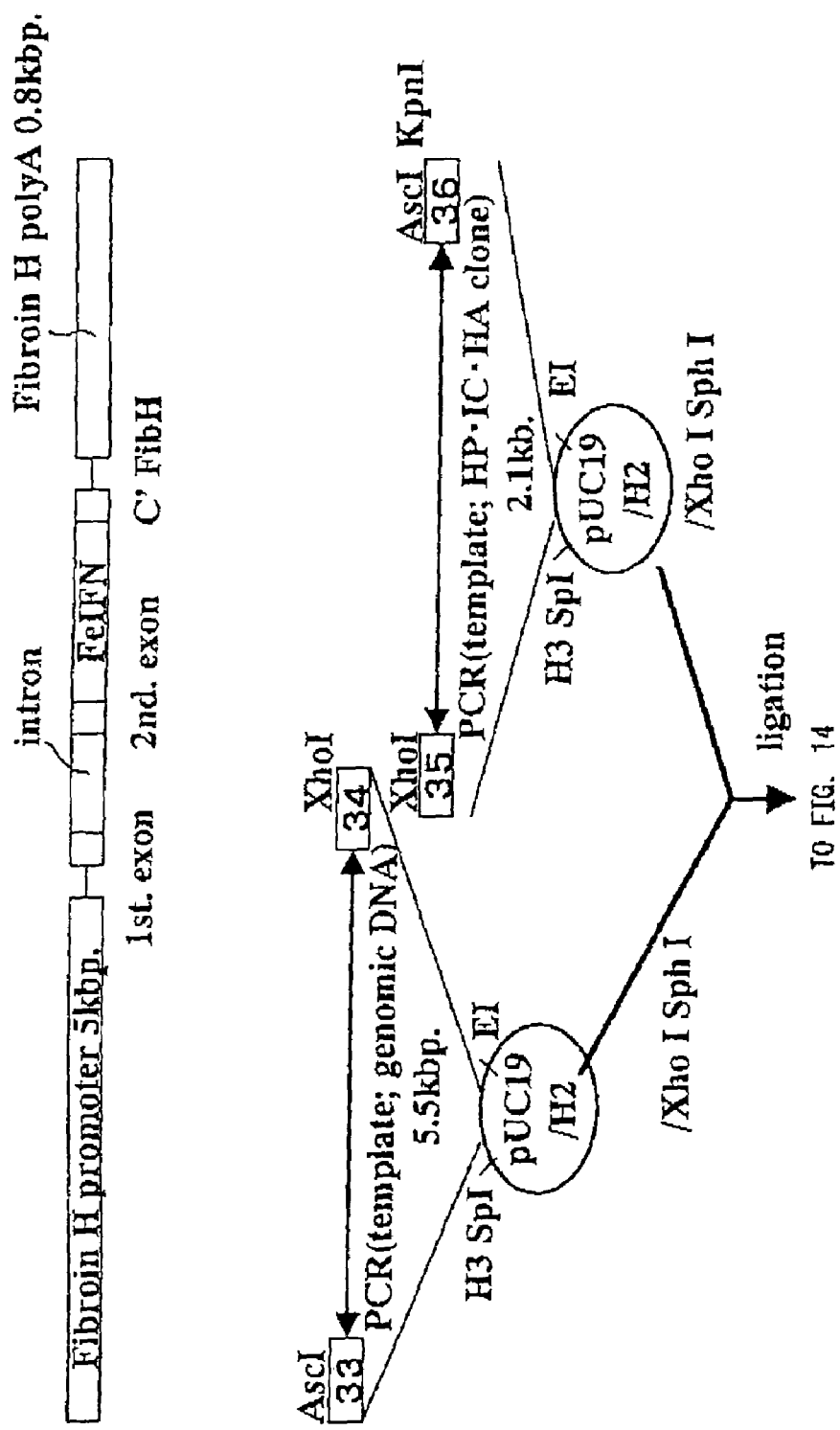
FIG. 13 is a drawing showing the procedure for producing a construct for gene insertion containing an HUP-IC-HA gene cassette (first half).
Figure 14:
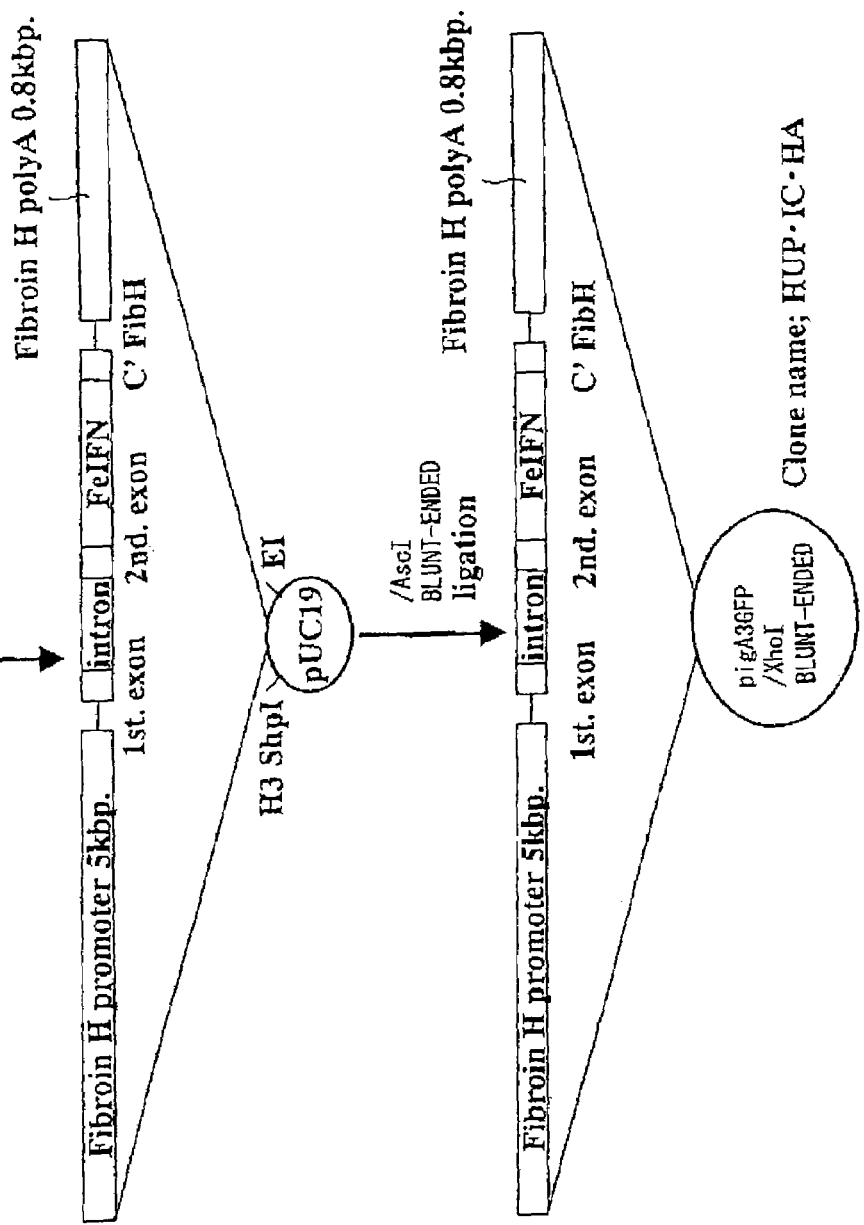
FIG. 14 is a drawing showing the procedure for producing a construct for gene insertion containing an HUP-IC-HA gene cassette (second half).

The HUP-IC-HA construct was produced according to the following procedure. A roughly 2.1 kbp fibroin H chain first intron-second exon region-feline interferon-ω-fibroin H chain C terminal region-fibroin B chain poly A signal region was acquired by PCR using two types of primers consisting of primer 35 (SEQ. ID No. 35) and primer 36 (SEQ. ID No. 36) and using 1 ng of HP-TC-HA construct for the template. This was then cleaved with XhoI and SphI followed by insertion therein of a roughly 5.5 kbp fragment (HUP region) cleaved with XhoI and SphI from a plasmid retaining fibroin H chain upstream promoter-fibroin H chain gene first exon-first intron. This plasmid retaining HUP, IC and HA was cleaved with AscI and the cleaved roughly 7.6 kbp fragment was blunt ended with T4 DNA Polymerase (Takara Shuzo) and coupled to blunt ended and dephosphorylated pigA3GFP XhoI site to produce a construct for gene insertion containing the HUP-IC-HA gene cassette. The procedure is shown in FIGS. 13 and 14.

Figure 15:
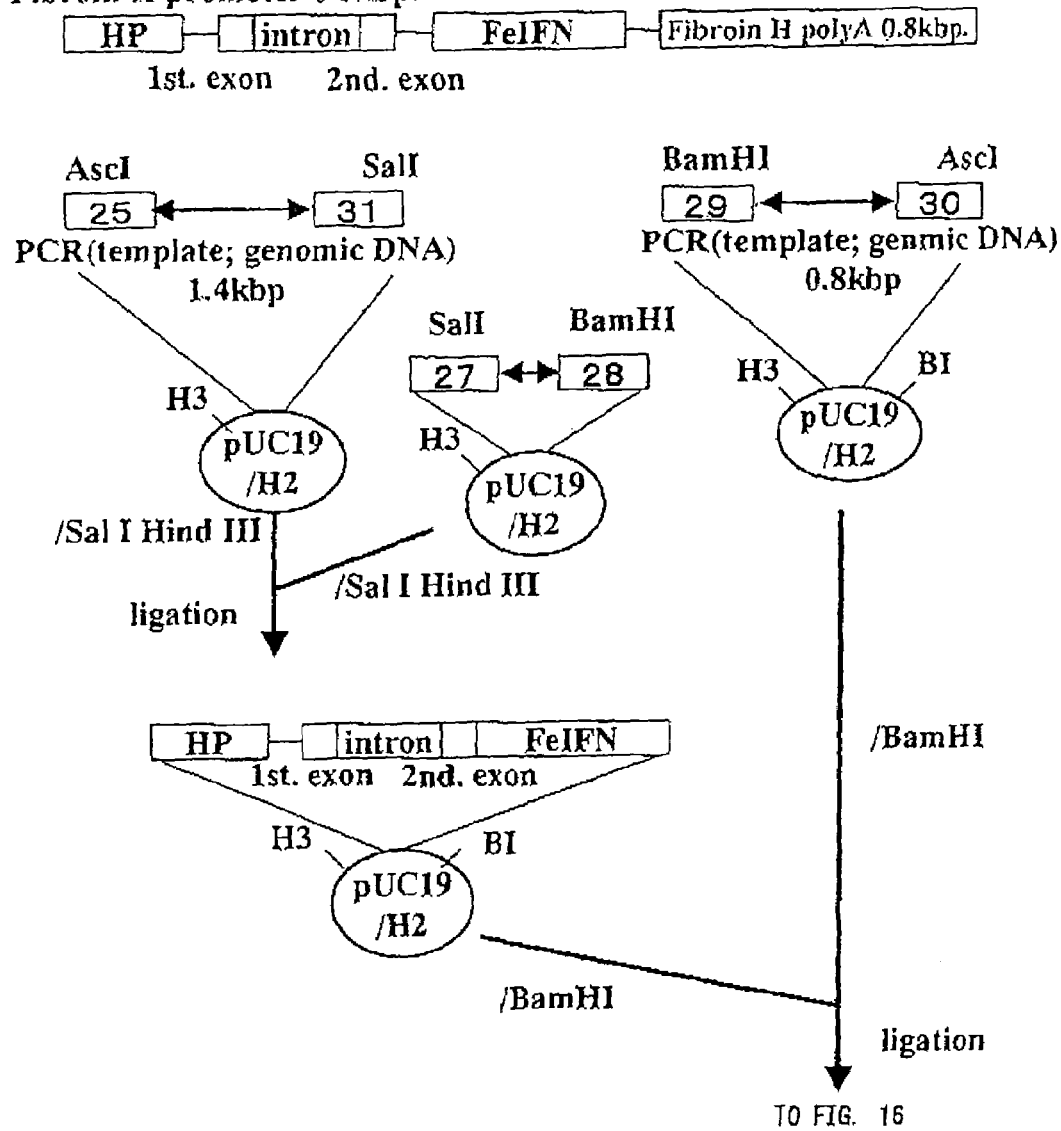
FIG. 15 is a drawing showing the procedure for producing a construct for gene insertion containing an HP-IC-A gene cassette (first half).
Figure 16:
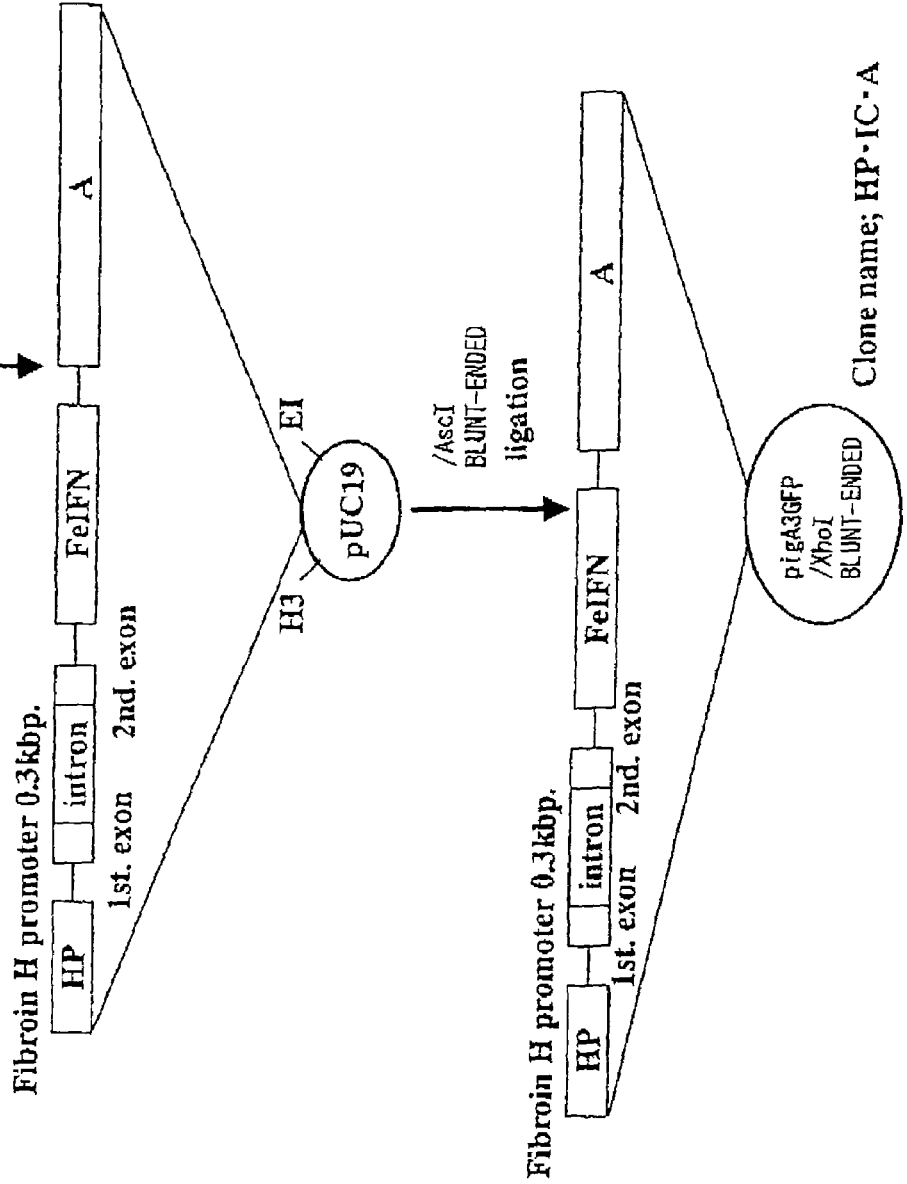
FIG. 16 is a drawing showing the procedure for producing a construct for gene insertion containing an HP-IC-A gene cassette (second half).

The HP-IC-A construct was produced according to the procedure described below. The plasmid retaining feline interferon-ω (IC region) prepared in Example 13 was cleaved with SalI and HindIII followed by insertion therein of a roughly 1.4 kbp fragment (HP region) cleaved with SalI and HindIII from a plasmid retaining fibroin H chain promoter-fibroin H chain first exon-first intron-second exon region. Moreover, this was cleaved with BamHI followed by insertion therein of a roughly 0.8 kbp fragment (region A) cleaved with BamHI from a plasmid retaining fibroin H chain poly A signal region. This plasmid retaining HP, IC and A was cleaved with AscI and the cleaved roughly 2.8 kbp fragment was blunt ended with T4 DNA Polymerase (Takara Shuzo) and coupled to blunt ended and dephosphorylated pigA3GFP XhoI site to produce a construct for gene insertion containing the HP-IC-A gene cassette. The procedure is shown in FIGS. 15 and 16.

The P-IC-A gene insertion construct, HP-IC-HA gene insertion construct, HUP-IC-HA gene insertion construct and HP-IC-A gene insertion construct were purified using the Qiagen Plasmid Maxi Kit in accordance with the protocol provided.

Example 16

Expression of β-Galactosidase in Silkworm Silk Gland

Gold Particles having a diameter of 1.6 μm were washed and sterilized with 100% ethanol and then suspended in sterilized distilled water (60 mg/ml). Incorporation of β-gal gene expression cassettes into silkworm silk glands was carried out using a gene gun. Namely, 50 μl (0.3 mg) of gold particles, 10 μg of expression plasmid pPgalA or pHPgalHA obtained in Example 14, 50 μl of 2.5 M calcium chloride and 20 μl of 0.1 M spermidine were successively mixed and after allowing to stand for 30 minutes at room temperature, the mixture was centrifuged to recover the gold particles coated with pHgalC. After washing the resulting metal particles twice with 70% ethanol, they were dispersed in 50 μl of 100% ethanol. 10 μl of the suspension of gold particles were placed on a microcarrier and dried. The Model PDS-1000/He (Bio-Rad) was used for the gene gun. The posterior silk glands excised from fifth instar third day silkworm larva were gently washed twice with PBS, placed on a 1% agar plate and sprayed with gold particles coated with DNA at a pressure of 1,100 psi. Following insertion of DNA, the silk glands were transferred to 20 ml of Grace's insect medium and cultured for 2 days at 25° C. After culturing, the culture supernatant and silk gland cells were recovered and confirmed for the expression of β-gal.

Expression was confirmed by Western analysis, The silk gland cells were homogenized in PBS to extract the cell contents. The culture supernatant and cell extract were both adjusted to a total protein concentration of 1.0 mg/ml, and these were then used as samples for SDS-PAGE. After blotting onto a membrane, β-gal protein was detected using the ECL Plus™ Western Blotting Kit (Amersham-Pharmacia) in accordance with the protocol provided. Namely, the blotted membrane was first blocked overnight at 4° C. in blocking solution (5% skim milk, 0.1% Tween20/PBS). The membrane was then washed twice with TPBS (0.1% Tween 20/PBS) and treated for 1 hour at room temperature with anti-β-gal protein antibody (Sigma) diluted 1000-fold with TPBS. The membrane was washed twice with TPBS and additionally washed three times with TPBS for 5 minutes each. After diluting 10000-fold with TPBS, the membrane was treated for 1 hour at room temperature with HRP-labeled anti-rabbit IgG antibody. After washing the membrane twice with TPBS and then three times with TPBS for 5 minutes each, the detection reagents of the ECL Plus™ Western Blotting Detection System (Amersham-Pharmacia) were added (Solution A+Solution B). Luminescence was then exposed onto HyperfilmTMECL™ and developed.

Figure 17:
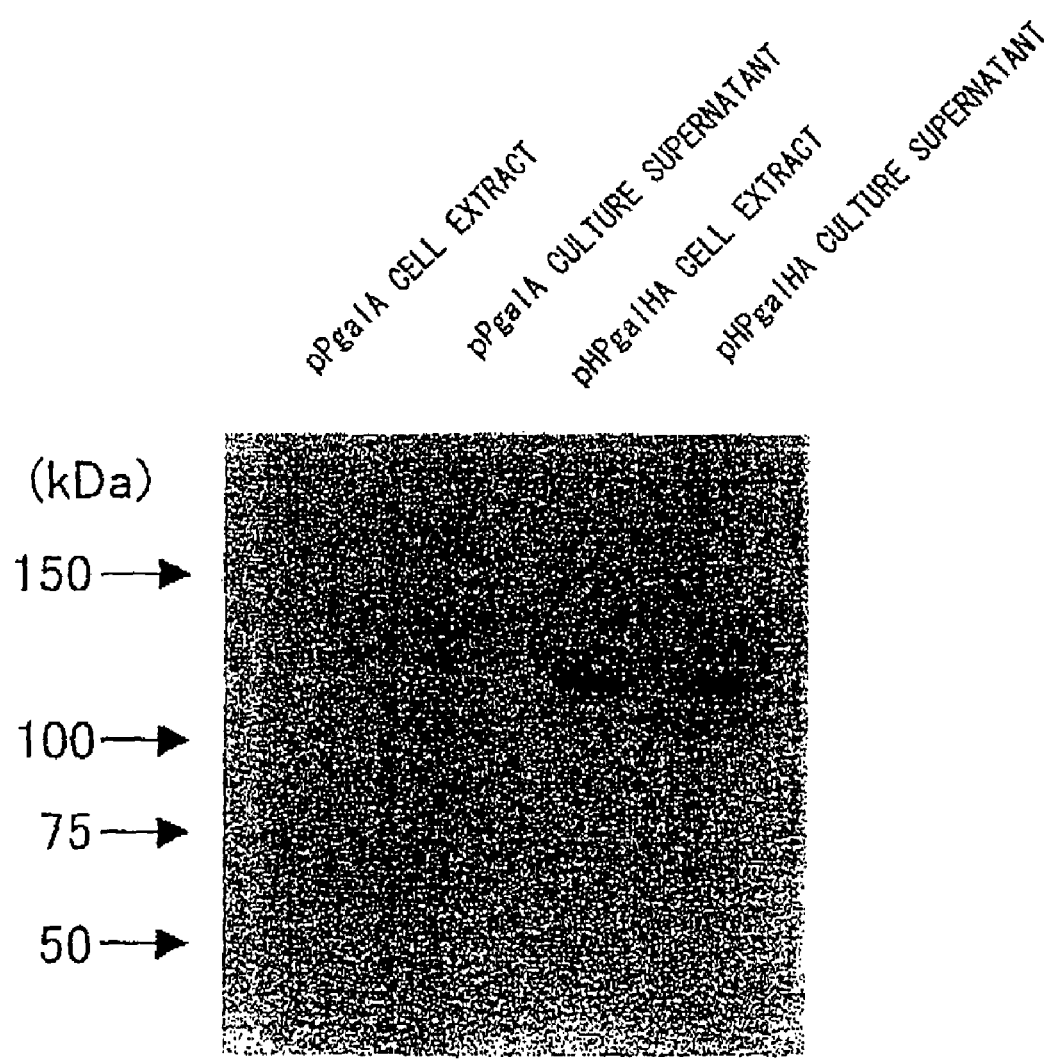
FIG. 17 is a drawing of the analysis of the expression of β-galactosidase in cultured silkworm silk glands by western analysis. The first exon, first intron and second exon regions of fibroin H chain gene were clearly determined to play an important role in synthesis or gene expression of proteins within cells. In addition, secretion outside the cells was also confirmed.

Since β-gal protein was only detected in the silk gland cells and culture supernatant containing pHPgalHA, it was clearly determined that a region other than fibroin H chain promoter, namely fibroin H chain gene first exon-first intron-second exon region, plays an important role in protein synthesis or gene expression within the cells. In addition, secretion outside the cells was also confirmed. Those results are shown in FIG. 17.

Example 17

Production of Recombinant Gene Silkworms

Each of the gene insertion plasmids described in Example 15 and DNA that produces piggyBac transposase protein (pHA3PIG) were adjusted to a concentration of 200 μg/ml each in 0.5 mM phosphate buffer (pH 7.0) and 5 mM KCl, after which 3 to 20 nl were micro-injected into silkworm eggs within 4 hours after being laid.

The larva that hatched from those silkworm eggs were raised, and the resulting adults (G0) were crossed within the same group. By observing the resulting first generation (G1) individuals for fluorescence of jellyfish green fluorescence protein, those silkworms that contained the jellyfish green fluorescence protein gene in their chromosomes were screened. As a result, gene recombinant silkworms were obtained that emitted fluorescent light due to the action of the jellyfish green fluorescence protein.

Example 18

Figure 18:
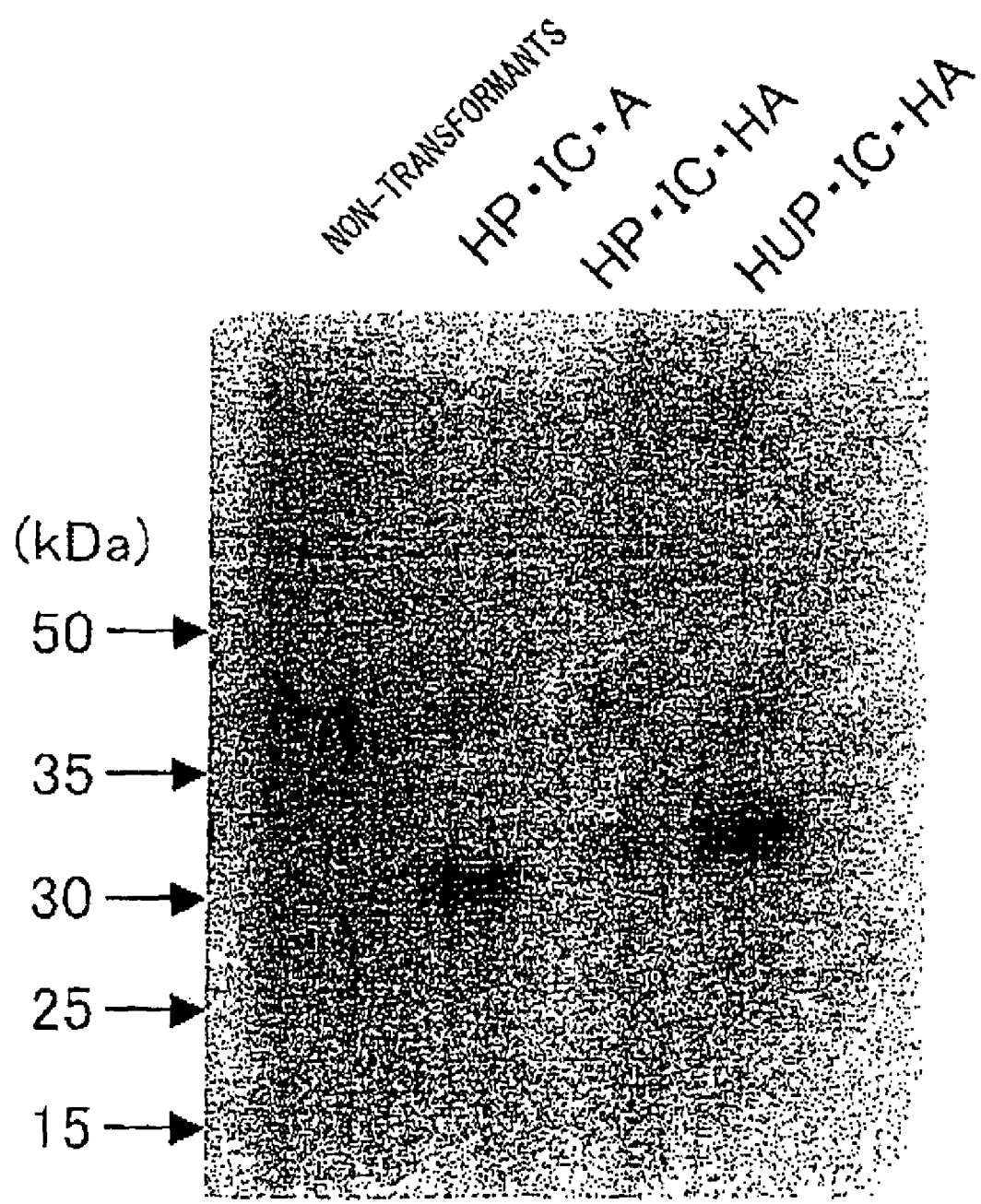
FIG. 18 is a drawing of the analysis of the expression of recombinant protein in silkworm silk gland tissue by Western analysis. The first exon, first intron and second exon regions of fibroin H chain gene were reconfirmed to play an important role in dramatically improving the expression of recombinant protein in silkworm posterior silk gland cells. In addition, a gene region that improves the amount of protein produced was found in a roughly 5.5 kbp upstream region from the fibroin promoter.

Expression Analysis of Recombinant Protein in Silk Gland Tissue by Western Analysis The expression of feline interferon-ω in tissue was investigated by Western analysis after recovering the posterior silk gland tissue from non-transformed silkworms and transformed silkworms (HP-IC-A transformed silkworms, HP-IC-EA transformed silkworms and HUP-IC-HA transformed silkworms). The silkworm posterior silk glands were homogenized in 100 mM sodium phosphate buffer (pH 7.0), and the supernatant was recovered following centrifugation for use as samples. Feline interferon was then detected using the ECL Plus™ Western Blotting Kit (Amersham-Pharmacia) in accordance with the protocol provided. Namely, the blotted membrane was blocked overnight at 4° C. in blocking solution (5% skim milk, 0.1% Tween20/PBS). The membrane was then washed twice with TPBS (0.1% Tween 20/PBS) and treated for 1 hour at room temperature with anti-feline interferon antibody diluted 1000-fold with TPBS. The membrane was washed twice with TBPS and additionally washed three times with TPBS for 5 minutes each. After diluting 10000-fold with TPBS, the membrane was treated for 1 hour at room temperature with HRP-labeled anti-rabbit IgG antibody. After washing the membrane twice with TPBS and then three times with TPBS for 5 minutes each, the detection reagents of the ECL Plus™ Western Blotting Detection System (Amersham-Pharmacia) were added (Solution A+Solution B). Luminescence was then exposed onto HyperfilmTMECL™ and developed. As a result, in contrast to signals not being detected from posterior silk gland tissue of the non-transformed silkworms and P-IC-A construct transformed silkworms, signals were detected from the posterior silk gland tissue of transformed silkworms containing the EP-IC-A construct, HP-IC-HA construct and HUP-IC-HA construct. Based on the results of this experiment, a region other than the fibroin H chain promoter, namely the fibroin H chain gene first exon-first intron-second exon region, was reconfirmed to play an important role in drastically improving protein synthesis or gene expression within silkworm posterior silk gland cells. These results are shown in FIG. 18. The accumulated amount of feline interferon in posterior silk gland tissue in the transformed silkworms containing the HUP-IC-HA gene cassette that contains the 5.5 kbp fibroin H chain 5' terminal region, feline interferon gene and fibroin H chain 3' terminal was higher than the accumulated amount of feline interferon in posterior silk gland tissue in transformed silkworms containing the HP-IC-HA gene cassette that contains the fibroin H chain 5' terminal promoter region, feline interferon gene and fibroin H chain 3' terminal. A gene region that improved the amount of protein produced is thought to be present in a region upstream from the E chain 5' terminal.

Example 19

Measurement of Recombinant Protein in Silk Thread by Western Analysis

Next, the secretion of exogenous protein, namely feline interferon-ω, in silk thread was investigated.

10 mg each of the cocoons from non-transformed silkworms and transformed silkworms (transformed silkworms containing the HP-IC-A gene, transformed silkworms containing the HP-IC-HA gene, and transformed silkworms containing the HUP-IC-HA gene) were weighed out, and after adding 4 ml of 60% LiSCN and stirring, the cocoons were dissolved by allowing to mix overnight at room temperature. The dissolved cocoons were then diluted 10-fold with 8 M urea, 2% SDS and 5% 2-mercaptoethanol to prepare samples. The levels of feline interferon in the samples were then detected using the ECL Plus™ Western Blotting Kit (Amersham-Pharmacia) in accordance with the protocol provided. Those results were then measured for signal intensity using a Molecular Imager (Bio-Rad) and the protein contents were measured by comparing with the signal intensities of known concentrations of feline interferon.

As a result, in contrast to signals not being detected from the cocoons of the non-transformed silkworms and transformed silkworms containing HP-IC-A gene, signals were detected from the cocoons of transformed silkworms containing HP-IC-HA gene and transformed silkworms containing HUP-IC-HA gene, thereby confirming that feline interferon protein is secreted into silk thread. In addition, the content was about 0.8 to 2.0% in HP-IC-HA transformed silkworms, and about 1.8 to 5.4% in HUP-IC-HA transformed silkworms. This is equivalent to 0.4 to 2 mg in terms of the weight per silkworm.

Figure 19:
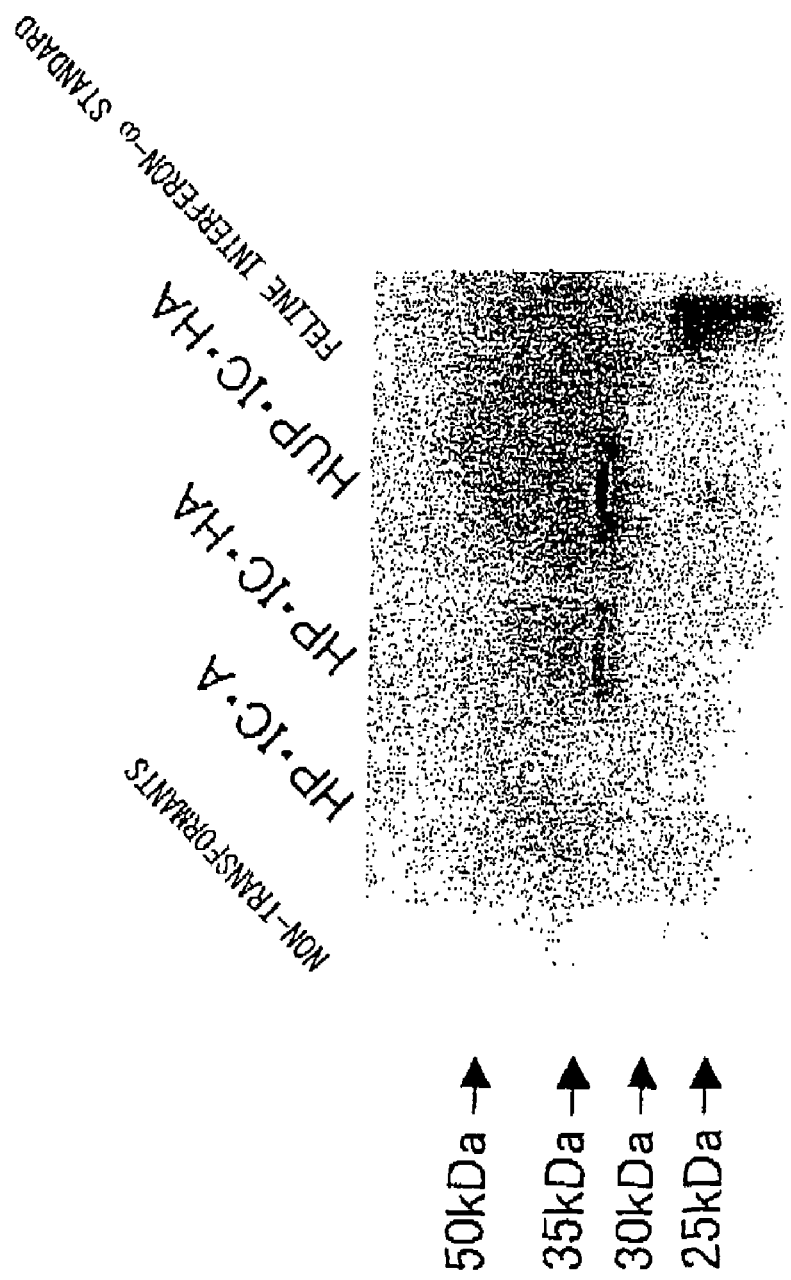
FIG. 19 is a drawing of the analysis of the production of recombinant protein in silk thread by western analysis. The 3' terminal portion of fibroin H chain gene was determined to play an important role in secretion of protein synthesized within silk gland cells to silk thread. In addition, a gene region that improves the amount of protein produced was reconfirmed in the roughly 5.5 kbp upstream region from the fibroin promoter.

On the basis of the results of this experiment, the 3' terminal portion of fibroin H chain gene was clearly demonstrated to play an important role in the secretion of protein synthesized in posterior silk gland cells into silk thread. These results are shown in FIG. 19. The amount of feline interferon produced in transformed silkworms containing the HUP-IC-HA gene cassette that contains a 5.5 kbp fibroin H chain 5' terminal promoter region, feline interferon gene and fibroin H chain 3' terminal was higher than the amount of feline interferon produced in transformed silkworms containing the HP-IC-HA gene cassette that contains fibroin H chain 5' terminal promoter region, feline interferon gene and fibroin H chain 3' terminal. A gene region that improves the amount of protein produced is considered to be present in a region upstream from the H chain 5' terminal.

Example 20

Measurement of Recombinant Protein in Silk Thread by ELISA

Quantitative determination of feline interferon-o in silk thread was carried out.

10 μg each of the cocoons from non-transformed silkworms and transformed silkworms (transformed silkworms containing the HP-IC-A gene, transformed silkworms containing the HP-IC-HA gene, and transformed silkworms containing the HUP-IC-HA gene) were weighed out, and after adding 4 ml of 60% LiSCN and stirring, the cocoons were dissolved by allowing them to mix overnight at room temperature. The dissolved cocoons were diluted 8-fold or 16-fold with PBS and applied to a microtiter plate. Known concentrations of feline interferon serially diluted with PBS were used for the standards.

As a result, feline interferon-ω was not detected in silk thread in transformed silkworms containing HP-IC-A gene, but was detected at about 1.1 to 2.2% in transformed silkworms containing HP-IC-HA gene, and at about 1.0 to 4.9% in transformed silkworms containing HUP-IC-HA gene.

INDUSTRIAL APPLICABILITY

A cytokine could be recovered in large volume while retaining its physiological activity from the silk glands or silk thread of gene recombinant silkworms obtained by producing a plasmid vector, in which a cytokine gene is coupled to a promoter that functions in silkworm silk glands, and then inserting those genes into silkworm chromosomes. In addition, the resulting cytokine extract has a low level of contaminating proteins, and can be purified easily as compared with methods of the prior art.

A large amount of exogenous protein could be produced within silk gland cells, outside silk gland cells and in silk thread by inserting an expression gene cassette, in which the DNA sequence of the 5' terminal portion and the DNA sequence of the 3' terminal portion of fibroin H chain gene were fused to an exogenous protein gene, into silk gland cells and so forth. The use of this novel technique led to the establishment of a technology for producing easily purified exogenous protein by producing exogenous protein using silk glands without the use of a recombinant baculovirus.

The invention claimed is:

1. A gene cassette for expressing an exogenous protein comprising in order:
   (1) an inverted repetitive sequence of a piggyBac transposon;
   (2) an approximately 5500 base pair sequence consisting of nucleotides 1-5484 of SEQ ID NO:23;
   (3) an exogenous protein gene coupled downstream from (2); and
   (4) an inverted repetitive sequence of a piggyBac transposon.

2. A gene cassette for expressing an exogenous protein comprising in order:
   (1) an inverted repetitive sequence of a piggyBac transposon;
   (2) an approximately 5500 base pair sequence consisting of nucleotides 1-5484 of SEQ ID NO:23;
   (3) an exogenous protein gene not containing a stop codon coupled downstream from (2);
   (4) a 3' terminal portion of the fibroin H chain gene fused to the 3' side of an exogenous protein structural gene; and
   (5) an inverted repetitive sequence of a piggyBac transposon.

3. The gene cassette according to claim 1 or claim 2, wherein the 5' terminal portion of the fibroin H chain gene contains a first exon, first intron and a portion of a second exon of the fibroin H chain gene.

4. The gene cassette according to claim 3, wherein the upstream region, the promoter and the 5' terminal portion together comprise the DNA as shown in SEQ ID NO: 23.

5. The gene cassette according to claim 2, wherein the 3' terminal portion of the fibroin H chain gene contains at least one codon that encodes cysteine.

6. The gene cassette according to claim 5, wherein the 3' terminal portion of the fibroin H chain gene consists of the DNA shown in SEQ ID NO: 24.

7. The gene cassette according to claims 1 or 2, wherein a poly A addition region of fibroin H chain gene is present downstream from the gene cassette.

8. A gene cassette for inserting a gene into chromosomes of insect cells comprising inverted repetitive sequences of a pair of piggyBac transposons present on both sides of the gene cassette according to claims 1 or 2.

9. An expression vector for insect cells that contains the gene cassette according to claims 1 or 2.

10. A gene insertion vector for insect cells that contains the gene cassette of claim 8 for inserting a gene into chromosomes of insect cells.

11. A process for producing an exogenous protein comprising inserting the vector for insect cells according to claim 9 into insect cells.

12. The process for producing an exogenous protein according to claim 11, wherein the insect cells originate in a lepidopteron.

13. The process for producing the exogenous protein according to claim 12, wherein the insect cells originate in *Bombyx mori*.

14. The process for producing an exogenous protein according to claim 13, wherein the insect cells are silk gland cells of *Bombyx mori*.

15. A process for producing an exogenous protein comprising producing a recombinant silkworm in which the gene cassette according to claims 1 or 2 is inserted into a chromosome using a gene insertion vector for insect cells and the DNA transfer activity of piggyBac transposase, producing exogenous protein in the silk glands or cocoon and silk thread of the resulting recombinant silkworm, recovering the exogenous protein from the silk glands or silk and cocoon thread in an aqeous solution.

16. The process for producing an exogenous protein according to claim 15, wherein the recombinant silkworm, in which the gene cassette for expressing an exogenous protein has been inserted into a chromosome, is produced by simultaneously micro-injecting the gene insertion vector for insect cells and DNA or RNA that produces the piggyBac transposase into silkworm eggs.

17. A process for producing an exogenous protein comprising inserting the vector for insect cells according to claim 10 into insect cells.

18. The process for producing an exogenous protein according to claim 17, wherein the insect cells originate in a lepidopteron.

19. The process for producing the exogenous protein according to claim 18, wherein the insect cells originate in *Bombyx mori*.

20. The process for producing an exogenous protein according to claim 19, wherein the insect cells are silk gland cells of *Bombyx mori*.

* * * * *

UNITED STATES PATENT AND TRADEMARK OFFICE
CERTIFICATE OF CORRECTION

PATENT NO. : 7,659,112 B2  Page 1 of 1
APPLICATION NO. : 10/506327
DATED : February 9, 2010
INVENTOR(S) : Shingo Hiramatsu et al.

It is certified that error appears in the above-identified patent and that said Letters Patent is hereby corrected as shown below:

On the front face of the patent:

The line reading "(73) Assignee: Toray Industries, Inc., Tokyo (JP)" should read
-- (73) Assignee: Toray Industries, Inc., Tokyo (JP) and National Institute of Agrobiological Sciences, Ibaraki (JP) --

Signed and Sealed this
Thirty-first Day of May, 2011

David J. Kappos
*Director of the United States Patent and Trademark Office*

SEQUENCE LISTING

```
<160> NUMBER OF SEQ ID NOS: 38

<210> SEQ ID NO 1
<211> LENGTH: 1910
<212> TYPE: DNA
<213> ORGANISM: Artificial Sequence
<220> FEATURE:
<223> OTHER INFORMATION: sericin-1 gene promoter-feline
      interferon-w-bovine growth hormone poly A addition sequence
<220> FEATURE:
<221> NAME/KEY: CDS
<222> LOCATION: (1071)...(1652)
<220> FEATURE:
<221> NAME/KEY: sig_peptide
<222> LOCATION: (1071)...(1139)
<220> FEATURE:
<221> NAME/KEY: mat_peptide
<222> LOCATION: (1140)...(1652)

<400> SEQUENCE: 1
ctcgagggtc agaaaccttg ttaaccaata gagccaaata tagttaacac aatagaaatt      60
tatccaaata ttattcgtgt attgtttata gcctttgtca agtcttttac aaggcaagat     120
aataagtaat attccgtgat tggacgtaac atttcccgga agatccttag ccgataagtc     180
gaagagccgc atgtggctag agagacgcgg gtttccgacc actggcttag gcgcttattc     240
cgccataata gatgtacgtg ttcacaatta gcacccgaaa ttcgtaatag ctacgagaag     300
tatcgaatat caaaaatcta tatattaata cgtgaagcaa aaactttgta tccctttta      360 cgaaaattgc gaggacggag gagtatgaaa tttcccacac ttatagagaa tacagagaag     420
aagtgcacaa tgctaatatt tttttaaaat aatgcataaa agatacttta aatcaataaa     480
gaaaacagca cacacactac ataccatgta tttgacgcac acacgcatgt atactattta     540
ttgtcaaact tttgttcttg acgtctgtgt tcaaactgag aatagattaa atattgtttg     600
tctttattaa tattttttaa tagtgtagtc ttggcgaaat ttgtgattat agaagtataa     660
aatacaatca taatagtgta caaacttaca attcccaatt aattatagtc gaatttcgac     720
tactgcggga cctctagtat taataattct ctttaaaaaa aaacagagca tcaaatactg     780
tcacaaatgt caagcgggtc tcaacgagcc atgaataaat tagaaatcaa ttaataacat     840
aaaataggca aacaaaataa aaccatttac atagagaacg tttgttgaac aaaaacaata     900
acttgtatac attgtttgca caaatgtttg aaccgaaaat ttattactct ctacgtaagc     960
ttgatcaaac ttcgttttcg tataaaacgc gttggcccaa ccactttggc atagtcgtct    1020
tatcatcggg tctctaagga tcaagcgatc caaagaccgc caacgtcgac atg gcg       1076
                                                         Met Ala
                                                          1 ctg ccc tct tcc ttc ttg gtg gcc ctg gtg gcg ctg ggc tgc aac tcc      1124
Leu Pro Ser Ser Phe Leu Val Ala Leu Val Ala Leu Gly Cys Asn Ser
```

```
                        5                  10                 15
gtc tgc gtg ctg ggc tgt gac ctg cct cag acc cac ggc ctg ctg aac        1172
Val Cys Val Leu Gly Cys Asp Leu Pro Gln Thr His Gly Leu Leu Asn
     20                  25                  30 agg agg gcc ttg acg ctc ctg gga caa atg agg aga ctc cct gcc agc        1220
Arg Arg Ala Leu Thr Leu Leu Gly Gln Met Arg Arg Leu Pro Ala Ser
 35                  40                  45                  50 tcc tgt cag aag gac aga aat gac ttc gcc ttc ccc cag gac gtg ttc        1268
Ser Cys Gln Lys Asp Arg Asn Asp Phe Ala Phe Pro Gln Asp Val Phe
                 55                  60                  65 ggt gga gac cag tcc cac aag gcc caa gcc ctc tcg gtg gtg cac gtg        1316
Gly Gly Asp Gln Ser His Lys Ala Gln Ala Leu Ser Val Val His Val
             70                  75                  80 acg aac cag aag atc ttc cac ttc ttc tgc aca gag gcg tcc tcg tct        1364
Thr Asn Gln Lys Ile Phe His Phe Phe Cys Thr Glu Ala Ser Ser Ser
         85                  90                  95 gct gct tgg aac acc acc ctc ctg gag gaa ttt tgc acg gga ctt gat        1412
Ala Ala Trp Asn Thr Thr Leu Leu Glu Glu Phe Cys Thr Gly Leu Asp
    100                 105                 110 cgg cag ctg acc cgc ctg gaa gcc tgt gtc ctg cag gag gtg gag gag        1460
Arg Gln Leu Thr Arg Leu Glu Ala Cys Val Leu Gln Glu Val Glu Glu
115                 120                 125                 130 gga gag gct ccc ctg acg aac gag gac att cat ccc gag gac tcc atc        1508
Gly Glu Ala Pro Leu Thr Asn Glu Asp Ile His Pro Glu Asp Ser Ile
                135                 140                 145 ctg agg aac tac ttc caa aga ctc tcc ctc tac ctg caa gag aag aaa        1556
Leu Arg Asn Tyr Phe Gln Arg Leu Ser Leu Tyr Leu Gln Glu Lys Lys
            150                 155                 160 tac agc cct tgt gcc tgg gag atc gtc aga gca gaa atc atg aga tcc        1604
Tyr Ser Pro Cys Ala Trp Glu Ile Val Arg Ala Glu Ile Met Arg Ser
        165                 170                 175 ttg tat tat tca tca aca gcc ttg cag aaa aga tta agg agc gag aaa        1652
Leu Tyr Tyr Ser Ser Thr Ala Leu Gln Lys Arg Leu Arg Ser Glu Lys
    180                 185                 190 tga tctagaccgc tgatcagcct cgactgtgcc ttctagttgc cagccatctg             1705
ttgtttgccc ctcccccgtg ccttccttga ccctggaagg tgccactccc actgtccttt      1765
cctaataaaa tgaggaaatt gcatcgcatt gtctgagtag gtgtcattct attctggggg      1825
gtggggtggg gcaggacagc aaggggagg attgggaaga caatagcagg catgctgggg       1885
atgcggtggg ctctatggcc tcgag                                            1910
```

<210> SEQ ID NO 2
<211> LENGTH: 1172
<212> TYPE: DNA
<213> ORGANISM: Artificial Sequence
<220> FEATURE:
<223> OTHER INFORMATION: fibroin H chain gene promoter-feline
      interferon-w-bovine growth hormone poly A addition sequence
<220> FEATURE:
<221> NAME/KEY: CDS
<222> LOCATION: (333)...(914)
<220> FEATURE:
<221> NAME/KEY: sig_peptide
<222> LOCATION: (333)...(401)
<220> FEATURE:
<221> NAME/KEY: mat_peptide
<222> LOCATION: (402)...(914)

<400> SEQUENCE: 2
ctcgagggga gaaagcatga agtaagttct ttaaatatta caaaaaaatt gaacgatatt        60
ataaaattct ttaaatatatt aaaagtaaga acaataagat caattaaatc ataattaatc      120

-continued

```
acattgttca tgatcacaat ttaatttact tcatacgttg tattgttatg ttaaataaaa    180
agattaattt ctatgtaatt gtatctgtac aatacaatgt gtagatgttt attctatcga    240
aagtaaatac gtcaaaactc gaaaattttc agtataaaaa ggttcaactt tttcaaatca    300
gcatcagttc ggttccaact ctcaaggtcg ac atg gcg ctg ccc tct tcc ttc     353
                                   Met Ala Leu Pro Ser Ser Phe
                                    1               5 ttg gtg gcc ctg gtg gcg ctg ggc tgc aac tcc gtc tgc gtg ctg ggc     401
Leu Val Ala Leu Val Ala Leu Gly Cys Asn Ser Val Cys Val Leu Gly
         10                  15                  20 tgt gac ctg cct cag acc cac ggc ctg ctg aac agg agg gcc ttg acg     449
Cys Asp Leu Pro Gln Thr His Gly Leu Leu Asn Arg Arg Ala Leu Thr
     25                  30                  35 ctc ctg gga caa atg agg aga ctc cct gcc agc tcc tgt cag aag gac     497
Leu Leu Gly Gln Met Arg Arg Leu Pro Ala Ser Ser Cys Gln Lys Asp
 40                  45                  50                  55 aga aat gac ttc gcc ttc ccc cag gac gtg ttc ggt gga gac cag tcc     545
Arg Asn Asp Phe Ala Phe Pro Gln Asp Val Phe Gly Gly Asp Gln Ser
                 60                  65                  70 cac aag gcc caa gcc ctc tcg gtg gtg cac gtg acg aac cag aag atc     593
His Lys Ala Gln Ala Leu Ser Val Val His Val Thr Asn Gln Lys Ile
             75                  80                  85 ttc cac ttc ttc tgc aca gag gcg tcc tcg tct gct gct tgg aac acc     641
Phe His Phe Phe Cys Thr Glu Ala Ser Ser Ser Ala Ala Trp Asn Thr
         90                  95                 100 acc ctc ctg gag gaa ttt tgc acg gga ctt gat cgg cag ctg acc cgc     689
Thr Leu Leu Glu Glu Phe Cys Thr Gly Leu Asp Arg Gln Leu Thr Arg
    105                 110                 115 ctg gaa gcc tgt gtc ctg cag gag gtg gag gag gga gag gct ccc ctg     737
Leu Glu Ala Cys Val Leu Gln Glu Val Glu Glu Gly Glu Ala Pro Leu
120                 125                 130                 135 acg aac gag gac att cat ccc gag gac tcc atc ctg agg aac tac ttc     785
Thr Asn Glu Asp Ile His Pro Glu Asp Ser Ile Leu Arg Asn Tyr Phe
                140                 145                 150 caa aga ctc tcc ctc tac ctg caa gag aag aaa tac agc cct tgt gcc     833
Gln Arg Leu Ser Leu Tyr Leu Gln Glu Lys Lys Tyr Ser Pro Cys Ala
            155                 160                 165 tgg gag atc gtc aga gca gaa atc atg aga tcc ttg tat tat tca tca     881
Trp Glu Ile Val Arg Ala Glu Ile Met Arg Ser Leu Tyr Tyr Ser Ser
        170                 175                 180 aca gcc ttg cag aaa aga tta agg agc gag aaa tga tctagaccgc          927
Thr Ala Leu Gln Lys Arg Leu Arg Ser Glu Lys
    185                 190 tgatcagcct cgactgtgcc ttctagttgc cagccatctg ttgtttgccc ctccccgtg    987 ccttccttga ccctggaagg tgccactccc actgtccttt cctaataaaa tgaggaaatt   1047
gcatcgcatt gtctgagtag gtgtcattct attctggggg gtggggtggg gcaggacagc   1107
aagggggagg attgggaaga caatagcagg catgctgggg atgcggtggg ctctatggcc   1167
tcgag                                                               1172
```

<210> SEQ ID NO 3
<211> LENGTH: 31
<212> TYPE: DNA
<213> ORGANISM: Artificial Sequence
<220> FEATURE:
<223> OTHER INFORMATION: Synthesized oligonucleotide used in PCR to acquire the feline interferon-w gene

<400> SEQUENCE: 3

```
acgcgtcgac atgggcgctg ccctcttcct t                                          31
```

<210> SEQ ID NO 4
<211> LENGTH: 30
<212> TYPE: DNA
<213> ORGANISM: Artificial Sequence
<220> FEATURE:
<223> OTHER INFORMATION: Synthesized oligonucleotide used in PCR to
      acquire the feline interferon-w gene

<400> SEQUENCE: 4

```
ctagtctaga tcatttctcg ctccttaatc                                            30
```

<210> SEQ ID NO 5
<211> LENGTH: 29
<212> TYPE: DNA
<213> ORGANISM: Artificial Sequence
<220> FEATURE:
<223> OTHER INFORMATION: Synthesized oligonucleotide used in PCR to
      acquire the sericin-1 gene promoter

<400> SEQUENCE: 5

```
ccggaattcg gtcagaaacc ttgttaacc                                             29
```

<210> SEQ ID NO 6
<211> LENGTH: 30
<212> TYPE: DNA
<213> ORGANISM: Artificial Sequence
<220> FEATURE:
<223> OTHER INFORMATION: Synthesized oligonucleotide used in PCR to
      acquire the sericin-1 gene promoter

<400> SEQUENCE: 6

```
acgcgtcgac gttggcggtc tttggatcgc                                            30
```

<210> SEQ ID NO 7
<211> LENGTH: 29
<212> TYPE: DNA
<213> ORGANISM: Artificial Sequence
<220> FEATURE:
<223> OTHER INFORMATION: Synthesized oligonucleotide used in PCR to
      acquire the fibroin H chain gene promoter

<400> SEQUENCE: 7

```
ccggaattcg ggagaaagca tgaagtaag                                             29
```

<210> SEQ ID NO 8
<211> LENGTH: 30
<212> TYPE: DNA
<213> ORGANISM: Artificial Sequence
<220> FEATURE:
<223> OTHER INFORMATION: Synthesized oligonucleotide used in PCR to
      acquire the fibroin H chain gene promoter

<400> SEQUENCE: 8

```
acgcgtcgac cttgagagtt ggaaccgaac                                            30
```

<210> SEQ ID NO 9
<211> LENGTH: 30
<212> TYPE: DNA
<213> ORGANISM: Artificial Sequence
<220> FEATURE:
<223> OTHER INFORMATION: Synthesized oligonucleotide used in PCR to
      acquire the bovine growth hormone gene poly A

<400> SEQUENCE: 9

```
ctagtctaga ccgctgatca gcctcgactg                                              30
```

<210> SEQ ID NO 10
<211> LENGTH: 30
<212> TYPE: DNA
<213> ORGANISM: Artificial Sequence
<220> FEATURE:
<223> OTHER INFORMATION: Synthesized oligonucleotide used in PCR to
      acquire the bovine growth hormone gene poly A

<400> SEQUENCE: 10

```
cgcggatccg ccatagagcc caccgcatcc                                              30
```

<210> SEQ ID NO 11
<211> LENGTH: 34
<212> TYPE: DNA
<213> ORGANISM: Artificial Sequence
<220> FEATURE:
<223> OTHER INFORMATION: Synthesized oligonucleotide used in PCR as a
      primer with a reaction solution of sericin-1 gene fragment, feline
      interferon-w gene fragment, and bovine growth hormone poly A

<400> SEQUENCE: 11

```
gacctcgagg gtcagaaacc ttgttaacca atag                                         34
```

<210> SEQ ID NO 12
<211> LENGTH: 30
<212> TYPE: DNA
<213> ORGANISM: Artificial Sequence
<220> FEATURE:
<223> OTHER INFORMATION: Synthesized oligonucleotide used in PCR as a
      primer with a reaction solution of sericin-1 gene fragment, feline
      interferon-w gene fragment, and bovine growth hormone poly A

<400> SEQUENCE: 12

```
gacctcgagg ccatagagcc caccgcatcc                                              30
```

<210> SEQ ID NO 13
<211> LENGTH: 29
<212> TYPE: DNA
<213> ORGANISM: Artificial Sequence
<220> FEATURE:
<223> OTHER INFORMATION: Synthesized oligonucleotide used in PCR as a
      primer with a reaction solution of fibroin H chain gene fragment,
      feline interferon-w gene fragment, and bovine growth hormone poly
      A

<400> SEQUENCE: 13

```
gacctcgagg ggagaaagca tgaagtaag                                               29
```

<210> SEQ ID NO 14
<211> LENGTH: 31
<212> TYPE: DNA
<213> ORGANISM: Artificial Sequence
<220> FEATURE:
<223> OTHER INFORMATION: Synthesized oligonucleotide used in PCR as a
      primer to obtain a human interferon-B gene fragment

<400> SEQUENCE: 14

```
acgcgtcgac atgaccaaca agtgtctcct c                                            31
```

<210> SEQ ID NO 15
<211> LENGTH: 30
<212> TYPE: DNA
<213> ORGANISM: Artificial Sequence
<220> FEATURE:
<223> OTHER INFORMATION: Synthesized oligonucleotide used in PCR as a
      primer to obtain a human interferon-B gene fragment -continued

<400> SEQUENCE: 15
ctagtctaga tcagtttcgg aggtaacctg                                              30

<210> SEQ ID NO 16
<211> LENGTH: 1151
<212> TYPE: DNA
<213> ORGANISM: Artificial Sequence
<220> FEATURE:
<223> OTHER INFORMATION: fibroin H chain promoter-human interferon-B
      gene-bovine growth hormone gene poly A signal (FhIB)
<220> FEATURE:
<221> NAME/KEY: CDS
<222> LOCATION: (333)...(893)
<220> FEATURE:
<221> NAME/KEY: sig_peptide
<222> LOCATION: (333)...(395)
<220> FEATURE:
<221> NAME/KEY: mat_peptide
<222> LOCATION: (396)...(893)

<400> SEQUENCE: 16
ctcgagggga gaaagcatga agtaagttct ttaaatatta caaaaaaatt gaacgatatt           60
ataaaattct ttaaaatatt aaaagtaaga acaataagat caattaaatc ataattaatc          120
acattgttca tgatcacaat ttaatttact tcatacgttg tattgttatg ttaaataaaa          180
agattaattt ctatgtaatt gtatctgtac aatacaatgt gtagatgttt attctatcga          240
aagtaaatac gtcaaaactc gaaaattttc agtataaaaa ggttcaactt tttcaaatca          300
gcatcagttc ggttccaact ctcaaggtcg ac                                       332 atg acc aac aag tgt ctc ctc caa att gct ctc ctg ttg tgc ttc tcc           380
Met Thr Asn Lys Cys Leu Leu Gln Ile Ala Leu Leu Leu Cys Phe Ser
 1               5                  10                  15 act aca gct ctt tcc atg agc tac aac ttg ctt gga ttc cta caa aga           428
Thr Thr Ala Leu Ser Met Ser Tyr Asn Leu Leu Gly Phe Leu Gln Arg
             20                  25                  30 agc agc aat ttt cag tgt cag aag ctc ctg tgg caa ttg aat ggg agg           476
Ser Ser Asn Phe Gln Cys Gln Lys Leu Leu Trp Gln Leu Asn Gly Arg
         35                  40                  45 ctt gaa tac tgc ctc aag gac agg atg aac ttt gac atc cct gag gag           524
Leu Glu Tyr Cys Leu Lys Asp Arg Met Asn Phe Asp Ile Pro Glu Glu
     50                  55                  60 att aag cag ctg cag cag ttc cag aag gag gac gcc gca ttg acc atc           572
Ile Lys Gln Leu Gln Gln Phe Gln Lys Glu Asp Ala Ala Leu Thr Ile
 65                  70                  75                  80 tat gag atg ctc cag aac atc ttt gct att ttc aga caa gat tca tct           620
Tyr Glu Met Leu Gln Asn Ile Phe Ala Ile Phe Arg Gln Asp Ser Ser
                 85                  90                  95 agc act ggc tgg aat gag act att gtt gag aac ctc ctg gct aat gtc           668
Ser Thr Gly Trp Asn Glu Thr Ile Val Glu Asn Leu Leu Ala Asn Val
            100                 105                 110 tat cat cag ata aac cat ctg aag aca gtc ctg gaa gaa aaa ctg gag           716
Tyr His Gln Ile Asn His Leu Lys Thr Val Leu Glu Glu Lys Leu Glu
        115                 120                 125 aaa gaa gat ttc acc agg gga aaa ctc atg agc agt ctg cac ctg aaa           764
Lys Glu Asp Phe Thr Arg Gly Lys Leu Met Ser Ser Leu His Leu Lys
    130                 135                 140 aga tat tat ggg agg att ctg cat tac ctg aag gcc aag gag tac agt           812
Arg Tyr Tyr Gly Arg Ile Leu His Tyr Leu Lys Ala Lys Glu Tyr Ser
145                 150                 155                 160 cac tgt gcc tgg acc ata gtc aga gtg gaa atc cta agg aac ttt tac           860
His Cys Ala Trp Thr Ile Val Arg Val Glu Ile Leu Arg Asn Phe Tyr -continued

```
                    165                 170                 175
ttc att aac aga ctt aca ggt tac ctc cga aac tga tctagaccgc          906
Phe Ile Asn Arg Leu Thr Gly Tyr Leu Arg Asn
                180                 185 tgatcagcct cgactgtgcc ttctagttgc cagccatctg ttgtttgccc ctccccgtg    966 ccttccttga ccctggaagg tgccactccc actgtccttt cctaataaaa tgaggaaatt   1026
gcatcgcatt gtctgagtag gtgtcattct attctggggg gtggggtggg gcaggacagc   1086 aaggggagg attgggaaga caatagcagg catgctgggg atgcggtggg ctctatggcc    1146
tcgag                                                               1151

<210> SEQ ID NO 17
<211> LENGTH: 1849
<212> TYPE: DNA
<213> ORGANISM: Artificial Sequence
<220> FEATURE:
<223> OTHER INFORMATION: sericin gene promoter-human interferon-B-bovine
      growth hormone gene poly A signal (ShIB)
<220> FEATURE:
<221> NAME/KEY: CDS
<222> LOCATION: (1071)...(1631)
<220> FEATURE:
<221> NAME/KEY: sig_peptide
<222> LOCATION: (1071)...(1133)
<220> FEATURE:
<221> NAME/KEY: mat_peptide
<222> LOCATION: (1134)...(1631)

<400> SEQUENCE: 17
ctcgagggtc agaaaccttg ttaaccaata gagccaaata tagttaacac aatagaaatt   60
tatccaaata ttattcgtgt attgtttata gcctttgtca agtcttttac aaggcaagat   120
aataagtaat attccgtgat tggacgtaac atttcccgga agatccttag ccgataagtc   180
gaagagccgc atgtggctag agagacgcgg gtttccgacc actggcttag gcgcttattc   240
cgccataata gatgtacgtg ttcacaatta gcacccgaaa ttcgtaatag ctacgagaag   300
tatcgaatat caaaaatcta tatattaata cgtgaagcaa aaactttgta tccctttta   360 cgaaaattgc gaggacggag gagtatgaaa tttcccacac ttatagagaa tacagagaag   420
aagtgcacaa tgctaatatt tttttaaaat aatgcataaa agatacttta aatcaataaa   480
gaaaacagca cacacactac ataccatgta tttgacgcac acacgcatgt atactattta   540
ttgtcaaact tttgttcttg acgtctgtgt tcaaactgag aatagattaa atattgtttg   600
tctttattaa tatttttttaa tagtgtagtc ttggcgaaat ttgtgattat agaagtataa   660
aatacaatca taatagtgta caaacttaca attcccaatt aattatagtc gaatttcgac   720
tactgcggga cctctagtat taataattct ctttaaaaaa aaacagagca tcaaatactg   780
tcacaaatgt caagcgggtc tcaacgagcc atgaataaat tagaaatcaa ttaataacat   840
aaaataggca aacaaaataa aaccatttac atagagaacg tttgttgaac aaaaacaata   900
acttgtatac attgtttgca caaatgtttg aaccgaaaat ttattactct ctacgtaagc   960
ttgatcaaac ttcgttttcg tataaaacgc gttggcccaa ccactttggc atagtcgtct   1020
tatcatcggg tctctaagga tcaagcgatc caaagaccgc caacgtcgac                1070 atg acc aac aag tgt ctc ctc caa att gct ctc ctg ttg tgc ttc tcc     1118
Met Thr Asn Lys Cys Leu Leu Gln Ile Ala Leu Leu Leu Cys Phe Ser
  1               5                  10                  15 act aca gct ctt tcc atg agc tac aac ttg ctt gga ttc cta caa aga     1166
Thr Thr Ala Leu Ser Met Ser Tyr Asn Leu Leu Gly Phe Leu Gln Arg
             20                  25                  30
```

```
agc agc aat ttt cag tgt cag aag ctc ctg tgg caa ttg aat ggg agg      1214
Ser Ser Asn Phe Gln Cys Gln Lys Leu Leu Trp Gln Leu Asn Gly Arg
        35                  40                  45 ctt gaa tac tgc ctc aag gac agg atg aac ttt gac atc cct gag gag      1262
Leu Glu Tyr Cys Leu Lys Asp Arg Met Asn Phe Asp Ile Pro Glu Glu
 50                  55                  60 att aag cag ctg cag cag ttc cag aag gag gac gcc gca ttg acc atc      1310
Ile Lys Gln Leu Gln Gln Phe Gln Lys Glu Asp Ala Ala Leu Thr Ile
 65                  70                  75                  80 tat gag atg ctc cag aac atc ttt gct att ttc aga caa gat tca tct      1358
Tyr Glu Met Leu Gln Asn Ile Phe Ala Ile Phe Arg Gln Asp Ser Ser
                 85                  90                  95 agc act ggc tgg aat gag act att gtt gag aac ctc ctg gct aat gtc      1406
Ser Thr Gly Trp Asn Glu Thr Ile Val Glu Asn Leu Leu Ala Asn Val
            100                 105                 110 tat cat cag ata aac cat ctg aag aca gtc ctg gaa gaa aaa ctg gag      1454
Tyr His Gln Ile Asn His Leu Lys Thr Val Leu Glu Glu Lys Leu Glu
        115                 120                 125 aaa gaa gat ttc acc agg gga aaa ctc atg agc agt ctg cac ctg aaa      1502
Lys Glu Asp Phe Thr Arg Gly Lys Leu Met Ser Ser Leu His Leu Lys
130                 135                 140 aga tat tat ggg agg att ctg cat tac ctg aag gcc aag gag tac agt      1550
Arg Tyr Tyr Gly Arg Ile Leu His Tyr Leu Lys Ala Lys Glu Tyr Ser
145                 150                 155                 160 cac tgt gcc tgg acc ata gtc aga gtg gaa atc cta agg aac ttt tac      1598
His Cys Ala Trp Thr Ile Val Arg Val Glu Ile Leu Arg Asn Phe Tyr
                165                 170                 175 ttc att aac aga ctt aca ggt tac ctc cga aac tga cagccatctg           1644
Phe Ile Asn Arg Leu Thr Gly Tyr Leu Arg Asn
            180                 185 ttgtttgccc ctccccgtg ccttccttga ccctggaagg tgccactccc actgtccttt     1704
cctaataaaa tgaggaaatt gcatcgcatt gtctgagtag gtgtcattct attctggggg    1764
gtggggtggg gcaggacagc aaggggagg attgggaaga caatagcagg catgctgggg     1824
atgcggtggg ctctatggcc tcgag                                          1849

<210> SEQ ID NO 18
<211> LENGTH: 28
<212> TYPE: DNA
<213> ORGANISM: Artificial Sequence
<220> FEATURE:
<223> OTHER INFORMATION: Synthesized oligonucleotide used in PCR as a
      primer to obtain feline granulocyte colony stimulating factor gene
      fragment

<400> SEQUENCE: 18
acgcgtcgac atgaagctga ccgccctg                                        28

<210> SEQ ID NO 19
<211> LENGTH: 28
<212> TYPE: DNA
<213> ORGANISM: Artificial Sequence
<220> FEATURE:
<223> OTHER INFORMATION: Synthesized oligonucleotide used in PCR as a
      primer to obtain feline granulocyte colony stimulating factor gene
      fragment

<400> SEQUENCE: 19
ctagtctaga tcagggcttg gtgaagtg                                        28

<210> SEQ ID NO 20
```

<211> LENGTH: 1175
<212> TYPE: DNA
<213> ORGANISM: Artificial Sequence
<220> FEATURE:
<223> OTHER INFORMATION: fibroin H chain promoter-feline granulocyte colony stimulating factor gene-bovine growth hormone gene poly A signal (FGB)
<220> FEATURE:
<221> NAME/KEY: CDS
<222> LOCATION: (333)...(917)
<220> FEATURE:
<221> NAME/KEY: sig_peptide
<222> LOCATION: (333)...(401)
<220> FEATURE:
<221> NAME/KEY: mat_peptide
<222> LOCATION: (402)...(917)

<400> SEQUENCE: 20

```
ctcgagggga gaaagcatga agtaagttct ttaaatatta caaaaaaatt gaacgatatt      60
ataaaattct ttaaaatatt aaaagtaaga acaataagat caattaaatc ataattaatc     120
acattgttca tgatcacaat ttaatttact tcatacgttg tattgttatg ttaaataaaa     180
agattaattt ctatgtaatt gtatctgtac aatacaatgt gtagatgttt attctatcga     240
aagtaaatac gtcaaaactc gaaaattttc agtataaaaa ggttcaactt tttcaaatca     300
gcatcagttc ggttccaact ctcaaggtcg ac                                   332 atg aag ctg acc gcc ctg cag ctg ctg ctg tgg cac agc gca ctc tgg       380
Met Lys Leu Thr Ala Leu Gln Leu Leu Leu Trp His Ser Ala Leu Trp
  1               5                  10                  15 atg gtg caa gaa gcc acc ccc ttg ggc cct acc agc tcc ctg ccc cag       428
Met Val Gln Glu Ala Thr Pro Leu Gly Pro Thr Ser Ser Leu Pro Gln
             20                  25                  30 agc ttc ctg ctc aag tgc tta gaa caa gtg agg aag gtc cag gct gat       476
Ser Phe Leu Leu Lys Cys Leu Glu Gln Val Arg Lys Val Gln Ala Asp
         35                  40                  45 ggc aca gcg ctg cag gag agg ctg tgc gcc gcc cac aag ctg tgc cac       524
Gly Thr Ala Leu Gln Glu Arg Leu Cys Ala Ala His Lys Leu Cys His
     50                  55                  60 cct gag gag ctg gtg ctg ctt ggg cac gct ctg ggc atc ccc cag gct       572
Pro Glu Glu Leu Val Leu Leu Gly His Ala Leu Gly Ile Pro Gln Ala
 65                  70                  75                  80 ccc ctg agc agc tgc tcc agc cag gcc ctg cag ctg acg ggc tgc ctg       620
Pro Leu Ser Ser Cys Ser Ser Gln Ala Leu Gln Leu Thr Gly Cys Leu
                 85                  90                  95 cgt caa ctc cac agt ggc ctc ttc ctc tac cag ggc ctc ctg cag gcc       668
Arg Gln Leu His Ser Gly Leu Phe Leu Tyr Gln Gly Leu Leu Gln Ala
            100                 105                 110 ctg gca ggg ata tcc ccc gag tta gcc ccc acc ctg gac atg ctg cag       716
Leu Ala Gly Ile Ser Pro Glu Leu Ala Pro Thr Leu Asp Met Leu Gln
        115                 120                 125 ctg gac atc acc gac ttt gct atc aac atc tgg cag cag atg gaa gac       764
Leu Asp Ile Thr Asp Phe Ala Ile Asn Ile Trp Gln Gln Met Glu Asp
    130                 135                 140 gtg ggg atg gcc cct gca gtg ccg ccc acc cag ggc acc atg cca acc       812
Val Gly Met Ala Pro Ala Val Pro Pro Thr Gln Gly Thr Met Pro Thr
145                 150                 155                 160 ttc acc tcg gcc ttc cag cgc cgg gca gga ggc acc ctg gtt gcc tcc       860
Phe Thr Ser Ala Phe Gln Arg Arg Ala Gly Gly Thr Leu Val Ala Ser
                165                 170                 175 aac ctg cag agc ttc ctg gag gtg gca tac cgt gct ctg cgc cac ttc       908
Asn Leu Gln Ser Phe Leu Glu Val Ala Tyr Arg Ala Leu Arg His Phe
            180                 185                 190
```

```
acc aag ccc tga tctagaccgc tgatcagcct cgactgtgcc ttctagttgc      960
Thr Lys Pro
      195 cagccatctg ttgtttgccc ctcccccgtg ccttccttga ccctggaagg tgccactccc    1020 actgtccttt cctaataaaa tgaggaaatt gcatcgcatt gtctgagtag gtgtcattct    1080 attctggggg gtgggtggg gcaggacagc aaggggagg attgggaaga caatagcagg      1140 catgctgggg atgcggtggg ctctatggcc tcgag                               1175

<210> SEQ ID NO 21
<211> LENGTH: 1873
<212> TYPE: DNA
<213> ORGANISM: Artificial Sequence
<220> FEATURE:
<223> OTHER INFORMATION: sericin gene promoter-feline granulocyte colony
      stimulating factor gene-bovine growth hormone gene poly A signal
      (SGB)
<220> FEATURE:
<221> NAME/KEY: CDS
<222> LOCATION: (1071)...(1655)
<220> FEATURE:
<221> NAME/KEY: sig_peptide
<222> LOCATION: (1071)...(1139)
<220> FEATURE:
<221> NAME/KEY: mat_peptide
<222> LOCATION: (1140)...(1655)

<400> SEQUENCE: 21
ctcgagggtc agaaaccttg ttaaccaata gagccaaata tagttaacac aatagaaatt     60
tatccaaata ttattcgtgt attgtttata gcctttgtca agtcttttac aaggcaagat    120
aataagtaat attccgtgat tggacgtaac atttcccgga agatccttag ccgataagtc    180
gaagagccgc atgtggctag agagacgcgg gtttccgacc actggcttag gcgcttattc    240
cgccataata gatgtacgtg ttcacaatta gcacccgaaa ttcgtaatag ctacgagaag    300
tatcgaatat caaaaatcta tatattaata cgtgaagcaa aaactttgta tcccttttta    360
cgaaaattgc gaggacggag gagtatgaaa tttcccacac ttatagagaa tacagagaag    420
aagtgcacaa tgctaatatt tttttaaaat aatgcataaa agatacttta aatcaataaa    480
gaaaacagca cacacactac ataccatgta tttgacgcac acacgcatgt atactattta    540
ttgtcaaact tttgttcttg acgtctgtgt tcaaactgag aatagattaa atattgtttg    600
tctttattaa tattttttaa tagtgtagtc ttggcgaaat ttgtgattat agaagtataa    660
aatacaatca taatagtgta caaacttaca attcccaatt aattatagtc gaatttcgac    720
tactgcggga cctctagtat taataattct ctttaaaaaa aaacagagca tcaaatactg    780
tcacaaatgt caagcgggtc tcaacgagcc atgaataaat tagaaatcaa ttaataacat    840
aaaataggca aacaaaataa aaccatttac atagagaacg tttgttgaac aaaaacaata    900
acttgtatac attgtttgca caaatgtttg aaccgaaaat ttattactct ctacgtaagc    960
ttgatcaaac ttcgttttcg tataaaacgc gttggcccaa ccactttggc atagtcgtct   1020
tatcatcggg tctctaagga tcaagcgatc caaagaccgc caacgtcgac                1070 atg aag ctg acc gcc ctg cag ctg ctg ctg tgg cac agc gca ctc tgg       1118
Met Lys Leu Thr Ala Leu Gln Leu Leu Leu Trp His Ser Ala Leu Trp
  1               5                  10                  15 atg gtg caa gaa gcc acc ccc ttg ggc cct acc agc tcc ctg ccc cag       1166
Met Val Gln Glu Ala Thr Pro Leu Gly Pro Thr Ser Ser Leu Pro Gln
             20                  25                  30 agc ttc ctg ctc aag tgc tta gaa caa gtg agg aag gtc cag gct gat       1214
Ser Phe Leu Leu Lys Cys Leu Glu Gln Val Arg Lys Val Gln Ala Asp
```

```
                     35                  40                    45
ggc aca gcg ctg cag gag agg ctg tgc gcc gcc cac aag ctg tgc cac    1262
Gly Thr Ala Leu Gln Glu Arg Leu Cys Ala Ala His Lys Leu Cys His
         50                  55                   60 cct gag gag ctg gtg ctg ctt ggg cac gct ctg ggc atc ccc cag gct    1310
Pro Glu Glu Leu Val Leu Leu Gly His Ala Leu Gly Ile Pro Gln Ala
 65                  70                  75                  80 ccc ctg agc agc tgc tcc agc cag gcc ctg cag ctg acg ggc tgc ctg    1358
Pro Leu Ser Ser Cys Ser Ser Gln Ala Leu Gln Leu Thr Gly Cys Leu
                 85                  90                  95 cgt caa ctc cac agt ggc ctc ttc ctc tac cag ggc ctc ctg cag gcc    1406
Arg Gln Leu His Ser Gly Leu Phe Leu Tyr Gln Gly Leu Leu Gln Ala
            100                 105                 110 ctg gca ggg ata tcc ccc gag tta gcc ccc acc ctg gac atg ctg cag    1454
Leu Ala Gly Ile Ser Pro Glu Leu Ala Pro Thr Leu Asp Met Leu Gln
        115                 120                 125 ctg gac atc acc gac ttt gct atc aac atc tgg cag cag atg gaa gac    1502
Leu Asp Ile Thr Asp Phe Ala Ile Asn Ile Trp Gln Gln Met Glu Asp
130                 135                 140 gtg ggg atg gcc cct gca gtg ccg ccc acc cag ggc acc atg cca acc    1550
Val Gly Met Ala Pro Ala Val Pro Pro Thr Gln Gly Thr Met Pro Thr
145                 150                 155                 160 ttc acc tcg gcc ttc cag cgc cgg gca gga ggc acc ctg gtt gcc tcc    1598
Phe Thr Ser Ala Phe Gln Arg Arg Ala Gly Gly Thr Leu Val Ala Ser
                165                 170                 175 aac ctg cag agc ttc ctg gag gtg gca tac cgt gct ctg cgc cac ttc    1646
Asn Leu Gln Ser Phe Leu Glu Val Ala Tyr Arg Ala Leu Arg His Phe
            180                 185                 190 acc aag ccc tga cagccatctg ttgtttgccc ctccccgtg ccttccttga        1698
Thr Lys Pro
        195 ccctggaagg tgccactccc actgtccttt cctaataaaa tgaggaaatt gcatcgcatt  1758 gtctgagtag gtgtcattct attctggggg gtggggtggg gcaggacagc aaggggagg   1818 attgggaaga caatagcagg catgctgggg atgcggtggg ctctatggcc tcgag      1873

<210> SEQ ID NO 22
<211> LENGTH: 1396
<212> TYPE: DNA
<213> ORGANISM: Bombyx mori

<400> SEQUENCE: 22
gggagaaagc atgaagtaag ttctttaaat attacaaaaa aattgaacga tattataaaa    60
ttctttaaaa tattaaaagt aagaacaata agatcaatta aatcataatt aatcacattg   120
ttcatgatca caatttaatt tacttcatac gttgtattgt tatgttaaat aaaaagatta   180
atttctatgt aattgtatct gtacaataca atgtgtagat gtttattcta tcgaaagtaa   240
atacgtcaaa actcgaaaat tttcagtata aaaaggttca acttttcaa atcagcatca    300 gttcggttcc aactctcaag atgagagtca aaacctttgt gatcttgtgc tgcgctctgc   360
aggtgagtta attattttac tattatttca gaaggtggcc agacgatatc acgggccacc   420
tgataataag tggtcgccaa aacgcacaga tatcgtaaat tgtgccattt gatttgtcac   480 gcccggggg gctacggaat aaactacatt tatttattta aaaatgaac cttagattat     540 gtaacttgtg atttatttgc gtcaaaagta ggcaagatga atctatgtaa atacctgggc   600
agacttgcaa tatcctattt caccggtaaa tcagcattgc aatatgcaat gcatattcaa   660
caatatgtaa aacaattcgt aaagcatcat tagaaaatag acgaaagaaa ttgcataaaa   720
```

```
ttataaccgc attattaatt tattatgata tctattaaca attgctattg cctttttttc      780
gcaaattata atcatttca taacctcgag gtagcattct gttacatttt aatacattgg      840
tatgtgatta taacacgagc tgcccactga gtttctcgcc agatcttctc agtgggtcgc     900
gttaccgatc acgtgataga ttctatgaag cactgctctt gttagggcta gtgttagcaa     960
attctttcag gttgagtctg agagctcacc tacccatcgg agcgtagctg aataggcta      1020 ccagctaata ggtagggaaa acaaagctcg aaacaagctc aagtaataac aacataatgt    1080
gaccataaaa tctcgtggtg tatgagatac aattatgtac tttcccacaa atgtttacat     1140
aattagaatg ttgttcaact tgcctaacgc cccagctaga acattcaatt attactatta    1200
ccactactaa ggcagtatgt cctaactcgt tccagatcag cgctaacttc gattgaatgt    1260
gcgaaattta tagctcaata ttttagcact tatcgtattg atttaagaaa aaattgttaa    1320 catttgttt cagtatgtcg cttatacaaa tgcaaacatc aatgattttg atgaggacta     1380
ttttgggagt gatgtc                                                     1396

<210> SEQ ID NO 23
<211> LENGTH: 6070
<212> TYPE: DNA
<213> ORGANISM: Bombyx mori

<400> SEQUENCE: 23
tcaagacatc cttgattaag gcagctgccg atattgacat ggacctcgtt cgtgctgcga     60
tagacgactg gccgcgcaga ttgaaggcct gtattcaaaa tcacggaggt cattttgaat   120
aaactttagt gtcataagaa tctatgtttt gttaagttca ttttggtata tgaatggtta   180
cataatgaat aaacttgttt caattatttt acattaaaca tgtgacagaa tttatgacct    240
gactaggtag gtacaaacag cctttttgat attagaaaac taagtaaaat agcctacggt    300
cacatctctt tccgtgggtg tcgttaaagg gcgactaga gaaccaccaa gaacgtagca     360
gaatcctcag agtgtcatac cagcatacag ccatcgctaa ctgctattta ctggtaatag   420
ggcacattgt aatctcactt aaccatactg tcgggccacc atctagccta tttctgccac    480
gaatcaatcg tgagtgatgg acatagagaa actattagtt gagaagaaaa caagagcact    540
aaaggtttga tattgacaaa aatctacttc gccgtcactc cataggttta ttgtctctca    600
ttagtccaga acagcagtta cagacgtaag cttttacgca caaactacag ggttgctctt    660
tattgtatcg aaaatatggg acctgaataa gggcgatttt gacgcgtcct gcccgcccat    720
tcccgatcct acggacagaa tggcaagcag tcgacgtcgc cccaaacacg tcatttcgga    780
tcctcacgat ccactaacgg tgcttttaggt acctcaagca ccggtcatcg ttctcgtcgg    840
acccgtcgct tgcgacgaag ggctcgacga gcaaattaac cctcagacac agcccactga    900
gtttctcgcc ggatcttctc agcgggtcgc gtttccgatc cggtggtaga ttctgcgaag    960
cacggctctt gctaggattc gtgttagcaa cgtcgtcagg tttgagcccc gtgagctcac    1020
ttactagtta aggttacgct gaaatagcct ctcaaggctc tcagctaggt aggaaacaaa    1080 aaaaaagtc ctgcccttaa caccgttgcg atggcttgtc ttctgcagcg tactgtcgtg    1140
gcagggcggt accgcaccat cttttttcgac gccaccttgt gatctgaagg cgaagatact   1200
cgaccttaat gattgaggca agagcgtaat acctcgcgct ccctagacga gtagatctcg    1260
tggaagattc ggcacacggc acacaaaaat agcttttgag atagccttca atgtaattat     1320 gttttttatat atatttacta gctgacccgg caaacgttgt gttgccttaa ataagatttc    1380
```

-continued

```
tagggaaatt ctagtgtaga aaaataacct cattcaacca cataatacct cattataacc    1440
aaaaaaaaat aatatccaaa aaataaaaat ataaaataaa tgtttggggt ggacaaccct    1500
tatcacatag gggtatgaaa attagatagt agccgattct cagacctact gaacatacta    1560
ttgatacaca aataaaacca aaaaaacatg gctgaaaaat gtatagtagg tattgtatta    1620
ttaagtgtat aatctatgat gtatatgagt aagtaagaca ggagaccggc ttcgtcctca    1680
tccgtcataa aaaccgtcat aaaaatcaaa cccgcaaaat tataatttgc gtaattactg    1740
gtggctggtg gtaggacctt cttgtgagtc cgcgcgggta ggtaccacca tctgactatt    1800
ctgccgtgaa gcagtaatgg gtttcggttt gaagggcggg acagccgttg taactatact    1860
tgagacctta gaacttatat ctcaatgtgg gtggcgcatt ttttttacggt aggcagcggc    1920
ttggctctgc ccctggcatt gctgaagtcc ataggcgacg gttaccactc accatcaggt    1980
gggccgtatg gccgtctgcc tacaaaatca ataaaaaaaa aataaaaaat ttacgttgta    2040
gatgtctatg ggctccagta accacttaac accaggcggg ctgtgagctc gtccacccat    2100
ctaagcaata aaaataaata aatagatagt tgatcagtag tggaccggcg agggcgggag    2160
atcaaattga atttaaaata aaacataatt aaaggaattt gaaactataa actctgaata    2220
ataatttatc gtactacaat tataatattt gattgccatc ttgcaaccct attgcggatc    2280
tgtgaataga aaaaaaaaaa aaatcgggat ggaaaaatag gggttgatcg tataagagtg    2340
aaaattgaga gtaatatgga atttttttat tttaagtcat gacaaaataa aaataagatc    2400
ttgccaaaaa aatttaagtt tattattaaa ttaagtttaa caaataaaaa attgggggttg    2460
atcgcagagg ggtgaaaatt tagggtttta tgtatttttg tatgctgtat cataaaaaaa    2520
taaaacaaa aaataaaaat agggggatga aaaataaatg ttgttcgatt ctcaaccctg    2580
gccgatatgc acgctaagat tcacaaaaat cggtcgagcc gtttcggagg agttcaatca    2640
cgcaccccgt cacacgagaa ttttatttat tagatttaga agagctgaaa gataaatcga    2700
tatttaatt tgtaagttgt cttgatgata cattttttcg tttgtcattc tttcctgcag    2760
ttagaacata atataaaatg caaatgaaaa atagaaatat aataaataat aataaataaa    2820
taataaatat ttactaacaa tcacgctacg ttaactggtc ccgtgataag ttcgtaaaga    2880
acttgtgtta caggtaccag ataacggata taaatgtaag atttttatta tacacataca    2940
tatatttcat atacattcat aaccctggaa aatacattta tatttatcat acaaatatct    3000
tcccttggcg ggattcgaac ccgcgacccc cttgtgtagt gacaatgtca cttaccacta    3060
cacccctctgg cattgctggg cgacggtaac cacccaccat taggtgggcc atatgctcgt    3120
ctgcctacaa gggaaataaa aaaaatatcc taatataaat tgcattaatt tttttaaacc    3180
gactttcaat cacaatgaag acagattctc gtcgaagttt gttttttgaaa ctatatcaat    3240
aactttcat tatccgttct tcgtcttttg tctttttttc gcaaacaaaa cgaacaaaac    3300
gttctaattc gaaagatgtt ttgtacggaa agtttgaata agtgcttaat tgcaagtaac    3360
gtaacaatgt tttagggttc ggtcctcaat aaattcgacc aataaaccat acaaattctt    3420
taacattttt ttaatcttat actagctgac ccggcagact tcgtggtgcc tcaatcgata    3480
aataaaatac ctatgcttct gtataaaata aacataaaac aaacaaaagg aatccgtccg    3540
acgggagaca catcaaagga aaaacatctt ttttattttt ttacctttta aaccttctct    3600
ggacttccac aaataattta agaccaaaat tagccaaatc ggtctagcat tttcgagttt    3660
tagcgagact aacgaacagc aattcatttt tatatacaca gatttatgtt accggggtct    3720
agtgacctaa acgacttcag ctctaacact aggctaactc aggcttagta gcctggtcct    3780
```

-continued

```
agtgttagat tgaagtcgt ctaatgcaaa gattattgga tctgatggat ccgtaaggac    3840
gtgtctagag cgtcgacggt gactagctcc tgcgtgatca ggaaaaatgt ggaaagctta    3900
acgattttgt cacattttac ttatcacaac ttgtttttat aataattcgc ttaaatgagc    3960
agctattact taatctcgta gtggtttttg acaaaatcag cttctttaga actaaaatat    4020
catttttttc gtaattttt taatgaaaaa tgctctagtg ttataccttt ccaaaatcac    4080
cattaattag gtagtgttta agcttgttgt acaaaactgc cacacgcatt tttttctcca    4140
ctgtaggttg tagttacgcg aaaacaaaat cgttctgtga aaattcaaac aaaaatattt    4200
tttcgtaaaa acacttatca atgagtaaag taacaattca tgaataattt catgtaaaaa    4260
aaaaatacta gaaaggaat ttttcattac gagatgctta aaaatctgtt tcaaggtaga    4320
gattttcga tatttcggaa aattttgtaa aactgtaaat ccgtaaaatt ttgctaaaca    4380
tatattgtgt tgttttggta agtattgacc caagctatca cctcctgcag tatgtcgtgc    4440
taattactgg acacattgta taacagttcc actgtattga caataataaa acctcttcat    4500
tgacttgaga atgtctggac agatttggct ttgtattttt gatttacaaa tgttttttg    4560
gtgatttacc catccaaggc attctccagg atggttgtgg catcacgccg attggcaaac    4620
aaaaactaaa atgaaactaa aagaaacag tttccgctgt cccgttcctc tagtgggaga    4680
aagcatgaag taagttcttt aaatattaca aaaaaattga acgatattat aaaattcttt    4740
aaaatattaa agtaagaac aataagatca attaaatcat aattaatcac attgttcatg    4800
atcacaattt aatttacttc atacgttgta ttgttatgtt aaataaaaag attaatttct    4860
atgtaattgt atctgtacaa tacaatgtgt agatgtttat tctatcgaaa gtaaatacgt    4920
caaaactcga aaattttcag tataaaaagg ttcaactttt tcaaatcagc atcagttcgg    4980
ttccaactct caagatgaga gtcaaaacct ttgtgatctt gtgctgcgct ctgcaggtga    5040
gttaattatt ttactattat ttcagaaggt ggccagacga tatcacgggc cacctgataa    5100
taagtggtcg ccaaaacgca cagatatcgt aaattgtgcc atttgatttg tcacgcccgg    5160
gggggctacg gaataaacta catttattta tttaaaaaat gaaccttaga ttatgtaact    5220
tgtgatttat ttgcgtcaaa agtaggcaag atgaatctat gtaaatacct gggcagactt    5280
gcaatatcct atttcaccgg taaatcagca ttgcaatatg caatgcatat tcaacaatat    5340
gtaaaacaat tcgtaaagca tcattagaaa atagacgaaa gaaattgcat aaaattataa    5400
ccgcattatt aatttattat gatatctatt aacaattgct attgcctttt tttcgcaaat    5460
tataatcatt ttcataacct cgaggtagca ttctgttaca ttttaataca ttggtatgtg    5520
attataacac gagctgccca ctgagtttct cgccagatct tctcagtggg tcgcgttacc    5580
gatcacgtga tagattctat gaagcactgc tcttgttagg gctagtgtta gcaaattctt    5640
tcaggttgag tctgagagct cacctaccca tcggagcgta gctggaatag gctaccagct    5700
aataggtagg gaaaacaaag ctcgaaacaa gctcaagtaa taacaacata atgtgaccat    5760
aaaatctcgt ggtgtatgag atacaattat gtactttccc acaaatgttt acataattag    5820
aatgttgttc aacttgccta acgccccagc tagaacattc aattattact attaccacta    5880
ctaaggcagt atgtcctaac tcgttccaga tcagcgctaa cttcgattga atgtgcgaaa    5940
tttatagctc aatattttag cacttatcgt attgatttaa gaaaaaattg ttaacatttt    6000
gtttcagtat gtcgcttata caaatgcaaa catcaatgat tttgatgagg actattttgg    6060
gagtgatgtc                                                            6070
```

```
<210> SEQ ID NO 24
<211> LENGTH: 99
<212> TYPE: DNA
<213> ORGANISM: Bombyx mori

<400> SEQUENCE: 24
cgcagttacg actattctcg tcgtaacgtc cgcaaaaact gtggaattcc tagaagacaa      60
ctagttgtta aattcagagc actgccttgt gtgaattgc                            99

<210> SEQ ID NO 25
<211> LENGTH: 28
<212> TYPE: DNA
<213> ORGANISM: Artificial Sequence
<220> FEATURE:
<223> OTHER INFORMATION: Primer used in PCR to acquire the Fibroin H
      chain promoter

<400> SEQUENCE: 25
ggcgcgccgg gagaaagcat gaagtaag                                        28

<210> SEQ ID NO 26
<211> LENGTH: 26
<212> TYPE: DNA
<213> ORGANISM: Artificial Sequence
<220> FEATURE:
<223> OTHER INFORMATION: Primer used in PCR to acquire the Fibroin H
      chain promoter

<400> SEQUENCE: 26
gtcgaccttg agagttggaa ccgaac                                          26

<210> SEQ ID NO 27
<211> LENGTH: 24
<212> TYPE: DNA
<213> ORGANISM: Artificial Sequence
<220> FEATURE:
<223> OTHER INFORMATION: Primer used in PCR to acquire the Feline
      interferon-w gene

<400> SEQUENCE: 27
gtcgacatgg cgctgccctc ttcc                                            24

<210> SEQ ID NO 28
<211> LENGTH: 26
<212> TYPE: DNA
<213> ORGANISM: Artificial Sequence
<220> FEATURE:
<223> OTHER INFORMATION: Primer used in PCR to acquire the Feline
      interferon-w gene

<400> SEQUENCE: 28
tgtggatcct ttctcgctcc ttaatc                                          26

<210> SEQ ID NO 29
<211> LENGTH: 32
<212> TYPE: DNA
<213> ORGANISM: Artificial Sequence
<220> FEATURE:
<223> OTHER INFORMATION: Primer used in PCR to acquire the Fibroin H
      chain poly A signal region

<400> SEQUENCE: 29
ggatcctaat ttttaatata aaataaccct tg                                   32

<210> SEQ ID NO 30
```

```
<211> LENGTH: 35
<212> TYPE: DNA
<213> ORGANISM: Artificial Sequence
<220> FEATURE:
<223> OTHER INFORMATION: Primer used in PCR to acquire the Fibroin H
      chain poly A signal region

<400> SEQUENCE: 30
cttggcgcgc cacgacgtag acgtatagcc atcgg                              35

<210> SEQ ID NO 31
<211> LENGTH: 31
<212> TYPE: DNA
<213> ORGANISM: Artificial Sequence
<220> FEATURE:
<223> OTHER INFORMATION: Primer used in PCR to acquire the Fibroin H
      chain promoter-fibroin H chain gene first exon-first intron-second
      exon region

<400> SEQUENCE: 31
cttgtcgacg acatcactcc caaaatagtc c                                  31

<210> SEQ ID NO 32
<211> LENGTH: 33
<212> TYPE: DNA
<213> ORGANISM: Artificial Sequence
<220> FEATURE:
<223> OTHER INFORMATION: Primer used in PCR to acquire the Fibroin H
      chain C terminal region gene-fibroin H chain poly A signal region

<400> SEQUENCE: 32
gtcggatccc gcagttacga ctattctcgt cgt                                33

<210> SEQ ID NO 33
<211> LENGTH: 31
<212> TYPE: DNA
<213> ORGANISM: Artificial Sequence
<220> FEATURE:
<223> OTHER INFORMATION: Primer used in PCR to acquire the Fibroin H
      chain upstream promoter-fibroin H chain gene first exon-first
      intron region

<400> SEQUENCE: 33
cccaatttgg cgcgcctcaa gacatccttg a                                  31

<210> SEQ ID NO 34
<211> LENGTH: 27
<212> TYPE: DNA
<213> ORGANISM: Artificial Sequence
<220> FEATURE:
<223> OTHER INFORMATION: Primer used in PCR to acquire the Fibroin H
      chain upstream promoter-fibroin H chain gene first exon-first
      intron region

<400> SEQUENCE: 34
gaatgctacc tcgaggttat gaaaatg                                       27

<210> SEQ ID NO 35
<211> LENGTH: 24
<212> TYPE: DNA
<213> ORGANISM: Artificial Sequence
<220> FEATURE:
<223> OTHER INFORMATION: Primer used in PCR to acquire the fibroin H
      chain first intron-second exon region-feline interferon-w-fibroin
      H chain C terminal region-fibroin H chain poly A signal region

<400> SEQUENCE: 35
aacctcgagg tagcattctg ttac                                          24
```

```
<210> SEQ ID NO 36
<211> LENGTH: 26
<212> TYPE: DNA
<213> ORGANISM: Artificial Sequence
<220> FEATURE:
<223> OTHER INFORMATION: Primer used in PCR to acquire the fibroin H
      chain first intron-second exon region-feline interferon-w-fibroin
      H chain C terminal region-fibroin H chain poly A signal region

<400> SEQUENCE: 36
ggtaccggcg cgccacgacg tagacg                                              26

<210> SEQ ID NO 37
<211> LENGTH: 30
<212> TYPE: DNA
<213> ORGANISM: Artificial Sequence
<220> FEATURE:
<223> OTHER INFORMATION: Primer used in PCR to acquire the
      B-galactosidase (B-gal) gene

<400> SEQUENCE: 37
gtcgacatgt cgtttacttt gaccaacaag                                          30

<210> SEQ ID NO 38
<211> LENGTH: 30
<212> TYPE: DNA
<213> ORGANISM: Artificial Sequence
<220> FEATURE:
<223> OTHER INFORMATION: Primer used in PCR to acquire the
      B-galactosidase (B-gal) gene

<400> SEQUENCE: 38
ggatcctttt tgacaccaga ccaactggta                                          30
```